US012735458B2

(12) United States Patent
Bourgault et al.

(10) Patent No.: US 12,735,458 B2
(45) Date of Patent: Sep. 15, 2026

(54) SELF-ASSEMBLED PEPTIDE NANORODS AND USES THEREOF

(71) Applicant: DÉVELOPPEMENT MONDIAL NANOTECH INC., Saint-Hyacinthe (CA)

(72) Inventors: Steve Bourgault, Montreal (CA); Denis Archambault, Longueuil (CA); Ximena Zottig, Montreal (CA); Soultan Al-Halifa, Quebec (CA)

(73) Assignee: DÉVELOPPEMENT MONDIAL NANOTECH INC., Saint-Hyacinthe (CA)

( * ) Notice: Subject to any disclaimer, the term of this patent is extended or adjusted under 35 U.S.C. 154(b) by 835 days.

(21) Appl. No.: 18/003,621

(22) PCT Filed: Jun. 29, 2020

(86) PCT No.: PCT/CA2020/050900
§ 371 (c)(1),
(2) Date: Dec. 28, 2022

(87) PCT Pub. No.: WO2022/000066
PCT Pub. Date: Jan. 6, 2022

(65) Prior Publication Data

US 2023/0234991 A1 Jul. 27, 2023

(51) Int. Cl.

*C07K 14/005* (2006.01)
*A61K 39/12* (2006.01)
*A61P 31/16* (2006.01)
*A61P 35/00* (2006.01)
*C07K 14/47* (2006.01)

(52) U.S. Cl.

CPC ............ *C07K 14/005* (2013.01); *A61K 39/12* (2013.01); *A61P 31/16* (2018.01); *A61P 35/00* (2018.01); *C07K 14/4711* (2013.01)

(58) Field of Classification Search

None
See application file for complete search history.

(56) References Cited

PUBLICATIONS

Bode. Cancer prevention research—then and now. Nat Rev; 9:508-516. (Year: 2009).*

Umar. Future directions in cancer prevention. Nat Rev; 12:835-848. (Year: 2012).*

Zottig. Nanomaterials; 10:1008. (Year: 2020).*

Sarfati. Preventing cancer: the only way forward. Lancet; 400:540-541. (Year: 2022).*

Kaczmarek. Cancer Vaccine Therapeutics: Limitations and Effectiveness—A Literature Review. Cells; 12:1-27. (Year: 2023).*

Babych. Engineering and evaluation of amyloid assemblies as a nanovaccine against the Chikungunya virus. Nanoscale; 10:19547. (Year: 2018).*

Zottig. Guiding the Morphology of Amyloid Assemblies by Electrostatic Capping: from Polymorphic Twisted Fibrils to Uniform Nanorods. Small; 15(33):e1901806. (Year: 2019).*

Al-Halifa, S.; Gauthier, L.; Arpin, D.; Bourgault, S.; Archambault, D., Nanoparticle-Based Vaccines Against Respiratory Viruses. Frontiers in immunology 2019, 10, 22.

Soultan Al-Halifa, Margaryta Babych, Ximena Zottig, Denis Archambault, Steve Bourgault. Amyloid self-assembling peptides: Potential applications in nanovaccine engineering and biosensing. Peptide Science. 2019;111:e24095.

Margaryta Babych, Geneviéve Bertheau-Mailhot, Ximena Zottig, Jessica Dion, Laurie Gauthier, Denis Archambault, and Steve Bourgault. Engineering and evaluation of amyloid assemblies as a nanovaccine against the Chikungunya virus. Nanoscale, 2018, 10, 19547-19556.

Jai S. Rudra, Ye F. Tiana, Jangwook P. Jung, and Joel H. Collier. A self-assembling peptide acting as an immune adjuvant. PNAS, Jan. 12, 2010, vol. 107 No. 2, 622-627.

Sharareh Eskandaria, Thalia Guerina, Istvan Totha, Rachel J. Stephenson. Recent advances in self-assembled peptides: Implications for targeted drug delivery and vaccine engineering. Advanced Drug Delivery Reviews 110-111 (2017) 169-187.

Jai S. Rudra, Satish Mishrac, Anita S. Chonga , Robert A. Mitchelld , Elizabeth H. Nardind, Victor Nussenzweigc , Joel H. CollierSelf-assembled peptide nanofibers raising durable antibody responses against a malaria epitope. Biomaterials, vol. 33, Issue 27, Sep. 2012, pp. 6476-6484.

Fazren Azmi, Abdullah Al Hadi Ahmad Fuaad, Mariusz Skwarczynski & Istvan Toth (2014) Recent progress in adjuvant discovery for peptide-based subunit vaccines, Human Vaccines & Immunotherapeutics, 10:3, 778-796.

Yi Wen and Joel H. Collier. Supramolecular peptide vaccines: tuning adaptive immunity. Current Opinion in Immunology 2015, 35:73-79.

(Continued)

*Primary Examiner* — Samira J Jean-Louis
*Assistant Examiner* — Maureen Varina Driscoll
(74) *Attorney, Agent, or Firm* — Alain Dumont; Lavery, de Billy, L.L.P.

(57) ABSTRACT

Self-assembling, cytocompatible peptides having the ability to form uniform nanorod assemblies are described. These peptides comprise a self-assembling β-sheet peptide and an amino terminal positively charged amino acid or amino acid analog, such as a lysine residue. Constructs comprising an antigen covalently attached to the self-assembling peptide are also disclosed, as well as the use of such constructs as vaccines for inducing an immune response against the antigen.

20 Claims, 22 Drawing Sheets

Specification includes a Sequence Listing.

(56) References Cited

PUBLICATIONS

Ximena Zottig, Soultan Al-Halifa, Margaryta Babych, Noé Quittot, Denis Archambault, and Steve Bourgault. Guiding the Morphology of Amyloid Assemblies by Electrostatic Capping: from Polymorphic Twisted Fibrils to Uniform Nanorods. Small 2019, 1901806. DOI: 10.1002/smll.201901806.

Ximena Zottig, Mélanie Côte-Cyr, Dominic Arpin, Denis Archambault, and Steve Bourgault. Protein Supramolecular Structures: From Self-Assembly to Nanovaccine Design. Nanomaterials 2020, 10, 1008; doi:10.3390/nano10051008.

International Search Report and Written Opinion in respect of PCT application No. PCT/CA2020/050900.

* cited by examiner

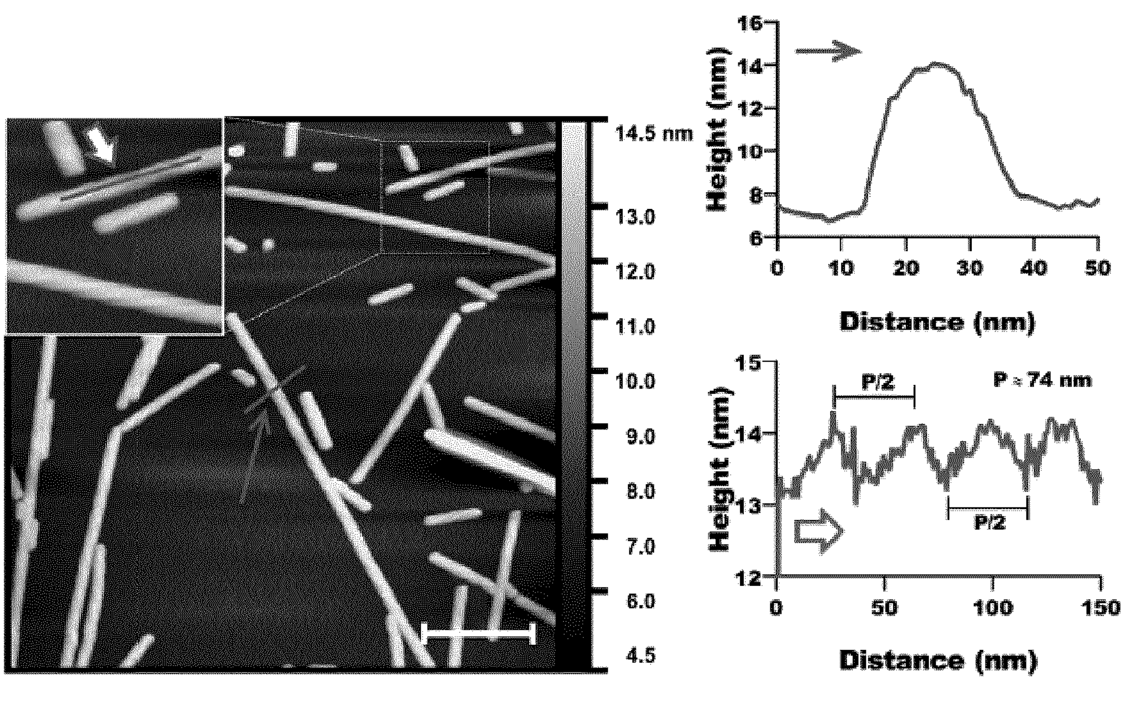
FIG. 3D
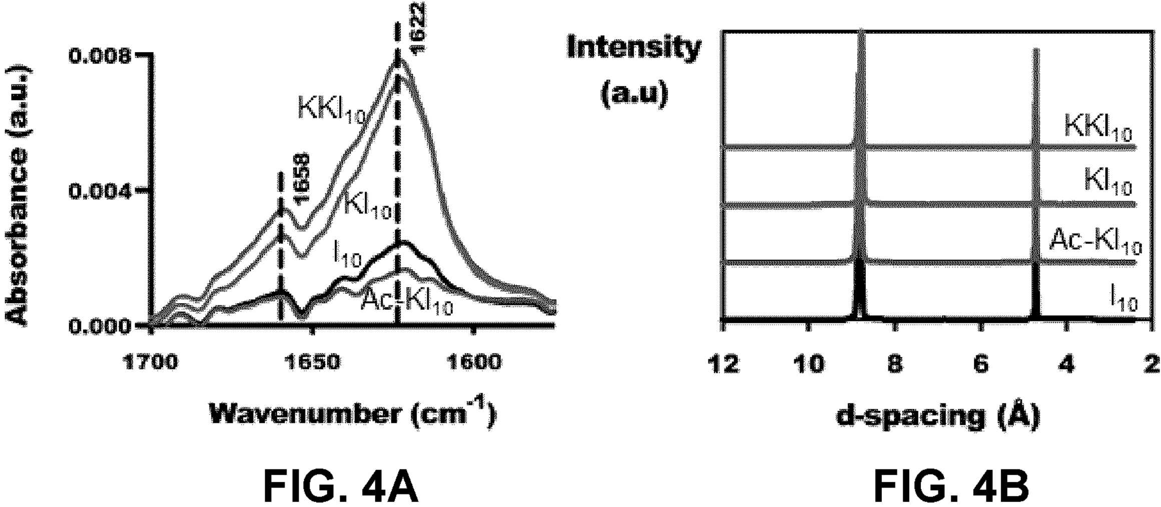
FIG. 4A
FIG. 4B

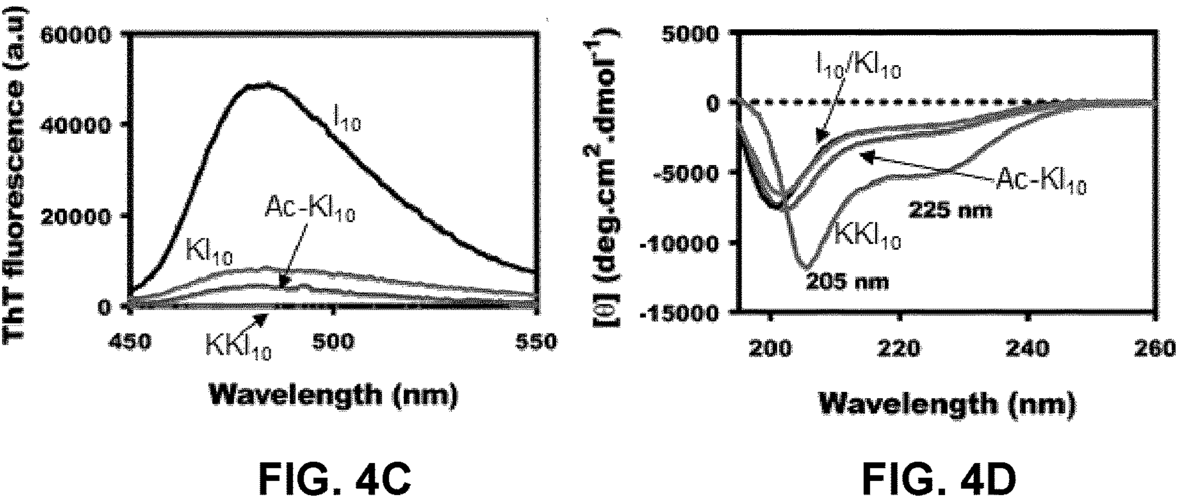
FIG. 4C
FIG. 4D
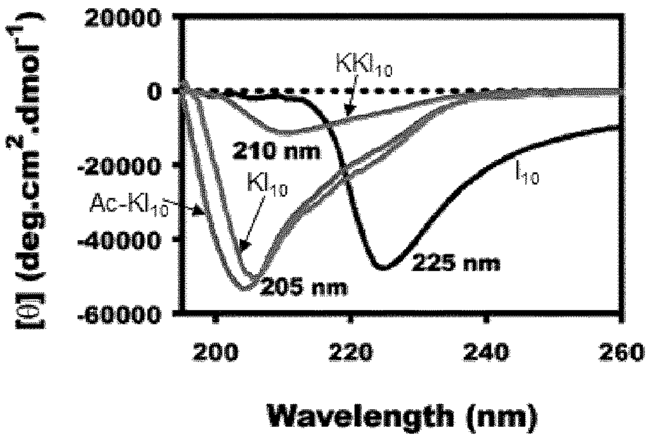
FIG. 4E
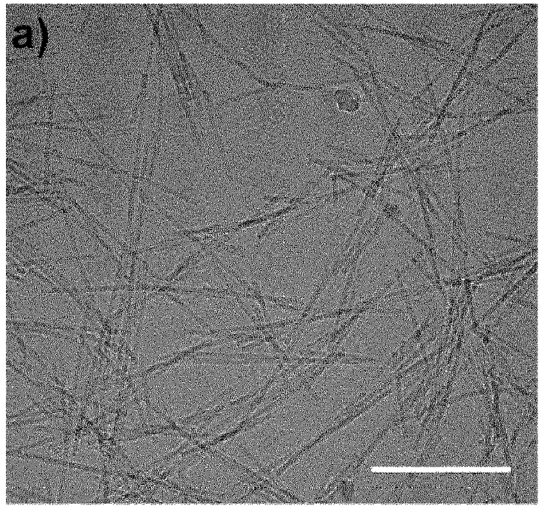
FIG. 5A

Turbidity (AU)
0.6
0.4
0.2
0.0
M2e-NRs
400 nm
600 nm

Pyrene $I_{373}/I_{384}$ ratio
2.0
1.9
1.8
1.7
1.6
1.5
CAC
352.7 μM
1
2
3
4
M2e-NRs concentration (Log *C*)

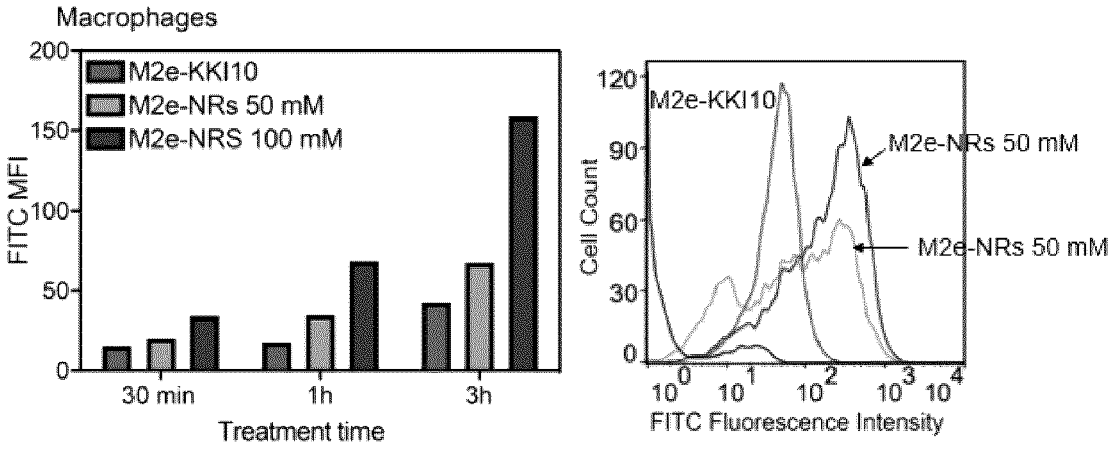
FIG. 11E
FIG. 11F
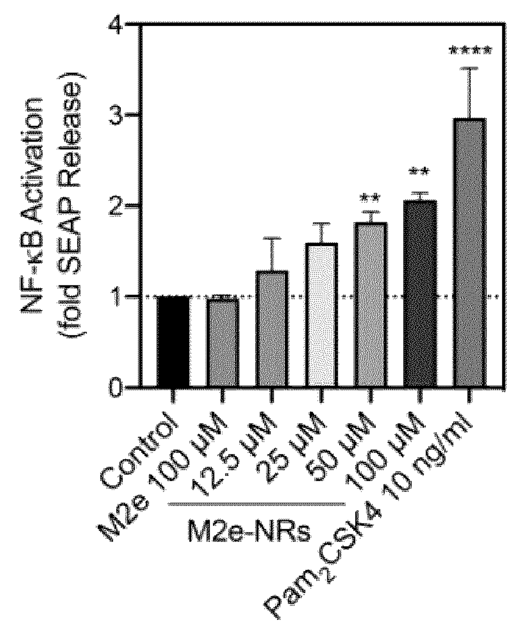
FIG. 11G
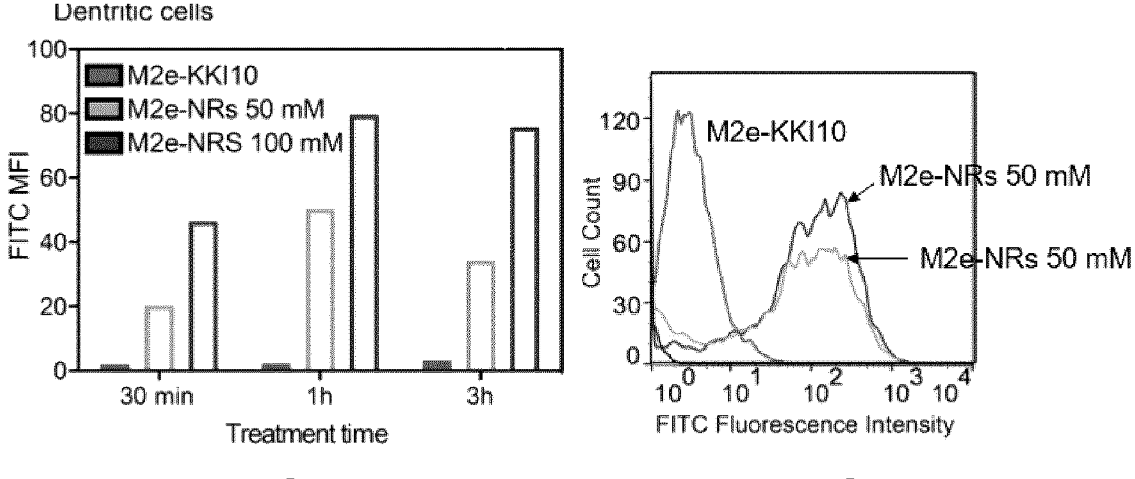
FIG. 11H
FIG. 11I

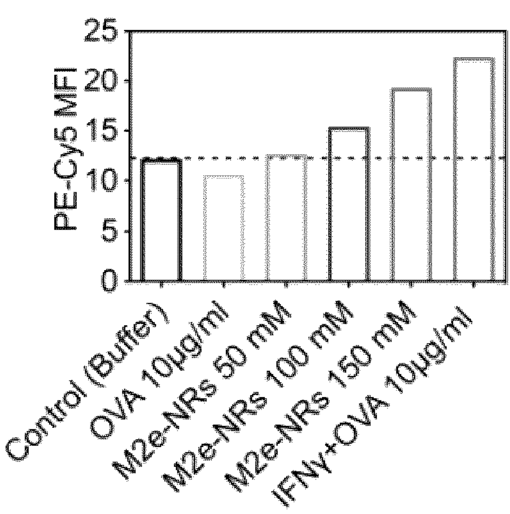
FIG. 11J
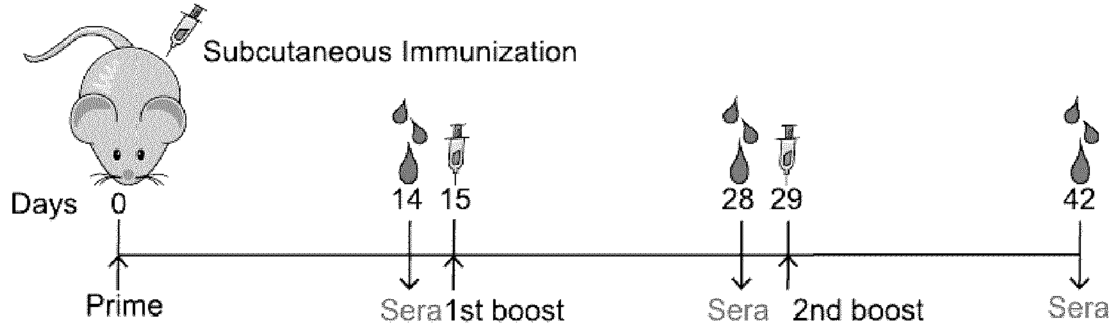
FIG. 12A
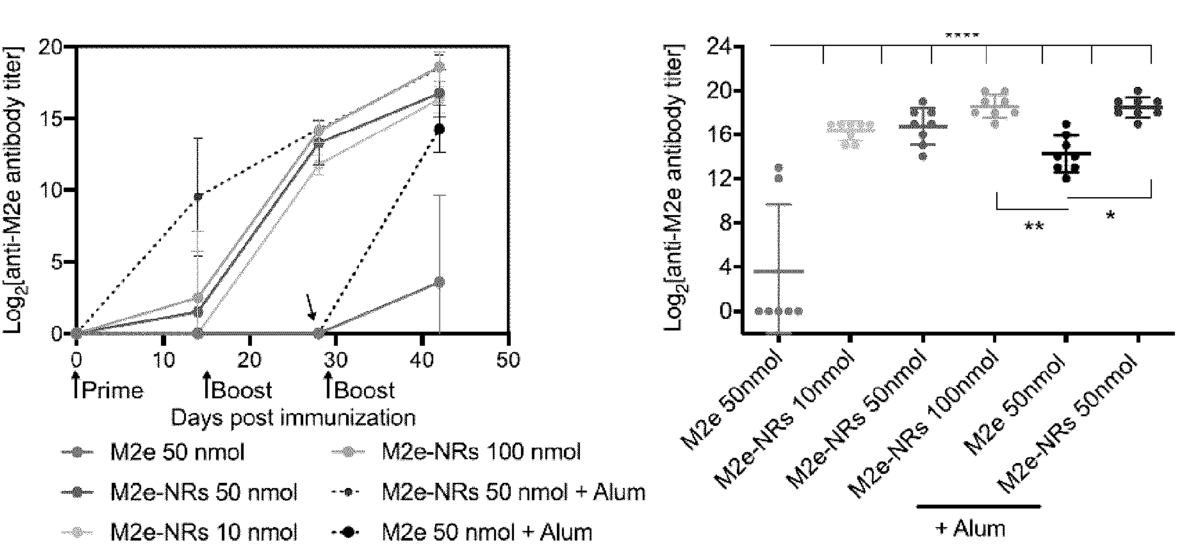
FIG. 12B
FIG. 12C

SELF-ASSEMBLED PEPTIDE NANORODS AND USES THEREOF

CROSS-REFERENCE TO RELATED APPLICATIONS

This application is a National Entry Application of PCT application No. PCT/CA2020/050900 filed on Jun. 29, 2020, which is incorporated herein by reference in its entirety.

TECHNICAL FIELD

The present invention generally relates to vaccines, and more particularly to delivery vehicles and adjuvants for molecules such as antigens.

SEQUENCE LISTING

A sequence listing is submitted herewith as an ASCII plain text file named 16135_8-seq listing_ST25.txt, that was created on Aug. 8, 2025, and having a size of ~3,338 bytes. The content of the aforementioned file is hereby incorporated by reference in its entirety.

BACKGROUND ART

Vaccination plays a central role in the fight against numerous infectious diseases and constitutes a key element of public health.[1] Historically, vaccine formulations have consisted of live-attenuated or inactivated microorganism.[2] Nonetheless, the aforementioned vaccination approaches are associated with safety concerns, such as risks of reversion to the pathogenic form and side reactions in host. To overcome these issues, subunit vaccines, which consist of specific purified antigens instead of whole microorganisms, have emerged as alternatives to conventional vaccines. However, these vaccine formulations are usually poorly immunogenic and require the co-administration of immunostimulating agents, known as adjuvants. Moreover, usage of subunit vaccines has been hampered by their low stability as well as by challenges associated with their production, including impurities resulting from their recombinant expression in prokaryotic and eukaryotic cells.[4] For instance, the use of recombinantly expressed protein subunits as antigens may induce an undesired autoimmune response due to traces of contaminantss.[5] In contrast to protein-based subunit vaccines, synthetic peptide vaccines present exceptional autoimmune tolerance, as they contain specific and highly pure epitope(s). Unfortunately, peptide-based subunit vaccines are poorly immunogenic, have low metabolic stability and poor pharmacokinetic parameters for a vaccine formulation.[6] To overcome these issues, synthetic peptide vaccines based on proteinaceous self-assembled nanoparticles have been developed.[7] These organized assemblies not only allow the enhancement of the immunogenicity and stabilization of the peptide antigen, but are also associated with multivalency, leading to efficient delivery, presentation and processing of antigenic determinants.[8] Lately, the interest of using peptides that self-assemble into defined supramolecular nanostructures for vaccine design has considerably increased.[9]

Short peptide sequences that self-assemble into long and linear cross-β fibrillar nanostructures bearing B- or T-cell epitopes, have been studied as vaccination nanoplatforms and were shown to boost the production of epitope-specific antibodies.[10-11] Whereas the formation of a depot at the injection site and protection of the antigen from proteolytic digestion are potential mechanisms of the adjuvant effect of fibrillar nanovaccines, the cross-β supramolecular architecture suggests that the particles could activate the innate immune responses. In addition, cross-β assemblies are biocompatible, have a robust physical and metabolic stability. However, considering the importance of the morphology and physicochemical properties of the nanovaccine, such as size, shape and surface charge, for the stimulation and polarization of the immune responses, the usage of cross-β fibrillar assemblies in vaccination remains limited by several issues.[14-15] Firstly, the difficulty of precisely controlling the self-assembly process and the intrinsic polymorphism in terms of length and mesoscopic structure, i.e. twisted filaments vs. flat ribbons, of the resulting assemblies precludes precise biophysical and immunological characterization. Secondly, the length in the micrometer scale of these linear cross-β fibrils likely polarizes the immune response towards T helper 2 (Th2) response, whereas the T helper 1 (Th1)-mediated response remains limited.[16] Not only a fine balance between the humoral and cellular responses is often required for protective immunity[4], polarization toward Th1 is usually needed to generate effective antiviral response. Thirdly, the cross-β-sheet assembly motif, which is characterized by stacks of β-sheets oriented perpendicularly to the fibril axis, is closely related to amyloid structures, whose tissue deposition and accumulation are associated with several diseases, including the Alzheimer's disease, Parkinson's disease and systemic amyloidoses.[17] Although recent studies have shown that amyloid fibrils are inert thermodynamic products of aggregation and that cytotoxicity is mainly associated with transient oligomers, concerns remain regarding their usage as nanomaterials for biomedical applications.[18-19] Particularly, it has been reported that different sequences under the amyloid fold can cross-interact with endogenous proteins and promote their amyloid aggregation. Thus, cross-seeding, equivalent to the prion-like effect, needs to be considered when using cross-β-sheet assembling motifs in the design of amyloid-like nanovaccines.[20]

There is thus a need for safer cross-β self-assembled peptides that may be used for antigen delivery in vaccines.

The present description refers to a number of documents, the content of which is herein incorporated by reference in their entirety.

SUMMARY OF THE INVENTION

The present disclosure provides the following items 1 to 44:

1. A construct comprising:
   i) a self-assembling domain of the formula: $X^1$-$X^2$-$L^1$-Z
   wherein $X^1$ is a lysine residue or an analog thereof comprising a primary amine in its side chain, or is absent; $X^2$ is a lysine residue or an analog thereof comprising a primary amine in its side chain; $L^1$ is a peptide linker of 2 to 8 amino acids; Z is a self-assembling β-sheet peptide; and ii) a molecule conjugated to the self-assembling domain.
2. The construct of item 1, wherein Z is a peptide of 15 amino acids or less comprising the sequence SNNFGAIL (SEQ ID NO:2) or a variant thereof having at least 80% identity with the sequence SNNFGAIL (SEQ ID NO:2).
3. The construct of item 2, wherein Z is a peptide of 15 amino acids or less comprising the sequence SNNF- GAILS (SEQ ID NO:3) or a variant thereof having at least 80% identity with the sequence SNNFGAILS (SEQ ID NO:3).

4. The construct of item 3, wherein Z is a peptide of 15 amino acids or less comprising the sequence SNNFGAILSS (SEQ ID NO:1) or a variant thereof having at least 80% identity with the sequence SNNFGAILSS (SEQ ID NO:1).

5. The construct of item 4, wherein Z is a peptide of the sequence SNNFGAILSS (SEQ ID NO:1).

6. The construct of any one of items 1 to 5, wherein $X^2$ is a lysine residue.

7. The construct of any one of items 1 to 6, wherein $X^1$ is a lysine residue or an analog thereof comprising a primary amine in its side chain.

8. The construct of item 7, wherein $X^1$ is a lysine residue.

9. The construct of any one of items 1 to 8, wherein $L^1$ is a peptide linker of 2 to 6 amino acids.

10. The construct of item 9, wherein L1 is a peptide linker of 4 amino acids.

11. The construct of any one of items 1 to 8, wherein peptide linker $L^1$ comprises glycine residues, serine residues, or a mixture thereof.

12. The construct of item 11, wherein peptide linker $L^1$ comprises a mixture of glycine and serine residues.

13. The construct of item 12, wherein peptide linker $L^1$ comprises or consists of the sequence GSGS (SEQ ID NO:4).

14. The construct of any one of items 1 to 13, wherein the self-assembling domain comprises or consists of the sequence KKGSGSSNNFGAILSS (SEQ ID NO: 5).

15. The construct of any one of items 1 to 14, wherein the molecule is conjugated to the self-assembling domain through a peptide linker $L^2$.

16. The construct of item 15, wherein $L^2$ is a peptide linker of 2 to 6 amino acids.

17. The construct of item 16, wherein $L^2$ is a peptide linker of 3 amino acids.

18. The construct of any one of items 15 to 17, wherein peptide linker $L^2$ comprises glycine residues, serine residues, or a mixture thereof.

19. The construct of item 18, wherein peptide linker $L^2$ comprises a mixture of glycine and serine residues.

20. The construct of item 19, wherein peptide linker $L^2$ comprises or consists of the sequence GSG.

21. The construct of any one of items 1 to 20, wherein the molecule is an antigen, preferably a protein from a microorganism or a peptide fragment thereof comprising at least 10 amino acids.

22. The construct of item 21, wherein the antigen is a viral protein, a bacterial protein or a fungal protein, or a peptide fragment thereof.

23. The construct of item 22, wherein the is a viral protein or a peptide fragment thereof.

24. The construct of item 23, wherein the viral protein or peptide fragment thereof is a protein from influenza virus or a peptide fragment thereof.

25. The construct of item 24, wherein the antigen is a peptide fragment derived from the extracellular domain of the influenza M2 protein (M2e).

26. The construct of any one of items 1 to 20, wherein the antigen is a tumor-specific antigen.

27. The construct of any one of items 21 to 26, wherein the antigen is a peptide fragment of 10 to 50 amino acids.

28. The construct of item 27, wherein the antigen comprises the sequence SLLTEVETPIRNEWGSRSNGSSD (SEQ ID NO:6).

29. A nanorod comprising the construct of any one of items 1 to 28.

30. The nanorod of item 29, wherein the nanorod has a length of between about 100 to about 200 nm.

31. The nanorod of item 30, wherein the nanorod has a length of between about 120 to about 160 nm.

32. A composition comprising a plurality of nanorods according to any one of items 29 to 31, wherein the plurality of nanorods have an average length of about 100 to about 200 nm±30-50 nm.

33. The composition of item 32, wherein the plurality of nanorods have an average length of about 120 to about 160 nm±30-50 nm.

34. The composition of item 33, wherein the plurality of nanorods have an average length of about 130 to about 150 nm±35-45 nm.

35. A vaccine comprising (i) the construct of any one of items 1 to 28, the nanorod of any one of items 29 to 31, or the composition of any one of items 32-34, and (ii) a vaccine adjuvant.

36. The vaccine of item 35, further comprising a pharmaceutically acceptable excipient.

37. A method for inducing an immune response against an antigen in a subject comprising administering to the subject an effective amount of: (i) the construct of any one of items 1 to 28, (ii) the nanorod of any one of items 29 to 31, (iii) the composition of any one of items 32-34; or (iv) the vaccine of item 35 or 36.

38. A method for preventing and/or treating a microbial infection or cancer in a subject comprising administering to the subject an effective amount of: (i) the construct of any one of items 1 to 28, (ii) the nanorod of any one of items 29 to 31, (iii) the composition of any one of items 32-34; or (iv) the vaccine of item 35 or 36.

39. Use of (i) the construct of any one of items 1 to 28, (ii) the nanorod of any one of items 29 to 31, (iii) the composition of any one of items 32-34; or (iv) the vaccine of item 35 or 36, for the manufacture of a medicament for inducing an immune response against an antigen in a subject.

40. Use of (i) the construct of any one of items 1 to 28, (ii) the nanorod of any one of items 29 to 31, (iii) the composition of any one of items 32-34; or (iv) the vaccine of item 35 or 36, for the manufacture of a medicament for preventing and/or treating a microbial infection or cancer in a subject.

41. Use of (i) the construct of any one of items 1 to 28, (ii) the nanorod of any one of items 29 to 31, (iii) the composition of any one of items 32-34; or (iv) the vaccine of item 35 or 36, for inducing an immune response against an antigen in a subject.

42. Use of (i) the construct of any one of items 1 to 28, (ii) the nanorod of any one of items 29 to 31, (iii) the composition of any one of items 32-34; or (iv) the vaccine of item 35 or 36, for preventing and/or treating a microbial infection or cancer in a subject.

43. The (i) construct of any one of items 1 to 28, (ii) nanorod of any one of items 29 to 31, (iii) composition of any one of items 32-34; or (iv) vaccine of item 35 or 36, for use in inducing an immune response against an antigen in a subject.

44. The (i) construct of any one of items 1 to 28, (ii) nanorod of any one of items 29 to 31, (iii) composition of any one of items 32-34; or (iv) vaccine of item 35 or 36, for use in preventing and/or treating a microbial infection or cancer in a subject.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIGS. 2A-1 show the effect of electrostatic N-terminal capping on the morphology of amyloid assemblies observed by transmission electron microscopy (TEM) and atomic force microscopy (AFM). FIG. 2A: $I_{10}$, FIG. 2B: Ac-$KI_{10}$, FIG. 2C: $KI_{10}$, FIG. 2D: $KKI_{10}$, FIGS. 2A, C and D: Magnified image; scale bar: 100 nm.

FIGS. 3A-D show the effect of positively charged capping units on the morphology of amyloid assemblies. AFM images and topography analysis of $KKI_{10}$ (FIG. 3A), $KI_{10}$ (FIG. 3B), Ac-$KI_{10}$ (FIG. 3C), and $1_{10}$ (FIG. 3D). Scale bar: 200 nm. Peptides were assembled in $50\times10^{-3}$ m Tris buffer, pH 7.4, under continuous rotary agitation for 48 h at a concentration of $500\times10^{-6}$ m (FIG. 3A) or $150\times10^{-6}$ m (FIGS. 3B-D).

FIGS. 4A-E show that positively capped assemblies have a cross-β-sheet structure. FIG. 4A: ATR-FTIR absorbance spectra showing parallel β-sheet secondary structure. FIG. 4B: X-ray diffraction (XRD) spectra revealing a periodic packing for all assemblies. FIG. 4C: Thioflavin T (ThT) fluorescence spectra of $I_{10}$ assemblies. ThT concentration is $40\times10^{-6}$ m. CD spectra at time 0 h (before assembly) (FIG. 4D) and after 48 h (FIG. 4E) incubation revealing the conformational transition associated with supramolecular self-assembly. Self-assembly occurred in $50\times10^{-3}$ m Tris, pH 7.4, for 48 h at a concentration of $150\times10^{-6}$ m ($KI_{10}$, Ac-$KI_{10}$, $1_{10}$) or $500\times10^{-6}$ m ($KKI_{10}$).

FIGS. 5A-F show cryo-TEM analysis and structural model of $KI_{10}$ nanorods. FIGS. 5A-C: Micrographs of vitrified $KI_{10}$ nanorods assembled in Tris-HCl ($50\times10^{-3}$ m, pH 7.4) with continuous agitation for 24 h at $400\times10^{-6}$ m. Scale bars correspond to 200 nm, 100 nm and 50 nm in FIGS. 5A-C, respectively. FIG. 5D: Quantification of cryo-TEM images. FIG. 5E: Reconstruction model of supramolecular arrangement of $KI_{10}$ nanorods inferred from Cryo-TEM analysis. FIG. 5F: Cross-β-sheet organization and distances packing from XRD measurements.

FIG. 6A: TEM images of $KI_{10}$ assemblies showing morphological stability over incubation time. $KI_{10}$ was assembled under circular agitation at $150\times10^{-6}$ m for 10 days. Scale bars: 500 nm (left) and 100 nm (right). FIG. 6B: TEM images of $KI_{10}$ assembled at $1.5\times10^{-3}$ m for 45 mins. Scale bars: 500 nm (left) and 200 nm (right). FIG. 6C: Thermal denaturation of $KI_{10}$ and $I_{10}$ amyloid-like assemblies monitored by CD spectroscopy. FIG. 6D: Critical aggregation concentration of $KI_{10}$ by pyrene fluorescence. Peptide solutions were prepared in $50\times10^{-3}$ m Tris, pH 7.4, and pyrene concentration was $2\times10^{-6}$ m.

FIG. 7A: HEKT293 and INS-1E cells were incubated for 24 h with $50\times10^{-6}$ m $I_{10}$ assemblies or soluble hIAPP and cell viability was evaluated by staining with calcein AM (live cells) and ethidium homodimer (dead cells). Scale bar: 20 μm. FIG. 7B: HEK 293T and INS-1E cells were incubated for 24 h with $50\times10^{-6}$ m of assemblies, or monomeric peptides, and metabolic activity was measured. Data represent mean±SD of at least three experiments performed in triplicate. Results were analyzed using the student's t-test and statistical difference (between control cells and treated cells) was established at *P<0.01.

FIG. 8C: morphological characterization of M2e-NRs relative to a classical amyloid fibril by TEM (left and center panel) and AFM (right panel) and corresponding size distribution of the assemblies. AFM scale bar: 500 nm. Rods were assembled in LPS-free Tris buffer (50 mM, pH 7.4) under continuous rotary agitation for 72 hours at a concentration of $1.5\times10^{-3}$ M.

FIG. 10A: cytocompatibility of M2e-$KKI_{10}$ (monomers) and M2e-NRs was determined by metabolic activity measurements in macrophage (J774A.1) and dendritic-like cells (DC2.4). Data represent mean±SD of at least three experiments performed in triplicate. Results were analyzed using the student's t-test and statistical difference (between control cells and treated cells) was established at (*) 0.01; () 0.001; (*) 0.0001; (**)<0.0001. FIG. 10**B: M2e-NRs cross-seeding capacity of a classical amyloid peptide (IAPP) evaluated by ThT fluorescence kinetic. Rods were assembled in LPS-free Tris buffer (50 mM, pH 7.4) under continuous rotary agitation for 72 hours at a concentration of $1.5\times10^{-3}$ M. Amyloid fibrils (IAPP) were assembled under quiescent conditions in Tris buffer (20 mM, pH 7.4) for 48 h at $50\times10^{-6}$ M.

FIGS. 11A-J show that M2e-NRs are efficiently internalized and activate APCs. Uptake by macrophages (J774.1) (FIG. 11A) and dendritic-like cells (DC2.4) (FIG. 11B) evaluated by confocal microscopy. Cells were treated for 3 h with FITC-labeled M2e-NRs. Corresponding orthogonal views are presented in FIG. 11B and FIG. 11D. Kinetics of internalization of M2e-NRs in J774.1 (FIG. 11E) and DC2.4 cells (FIG. 11G) monitored by FACS using Trypan blue (1 mg/ml) to quench membrane fluorescence. Representative FACS histogram of internalization at optimal incubation time (FIGS. 11F and 11H) and comparison between assemblies and monomers. FITC-labeled M2e-KKI10 was co-assembled with unlabeled $KKI_{10}$ peptide in 1:5 and 1:7 molar ratios (LPS-free Tris buffer, 50 mM, pH 7.4) under continuous rotary agitation for 72 hours at a concentration of $1.5\times10^{-3}$ M. FIG. 11I: Activation of TLR-2 by M2e-NRs determined by SEAP activity measurement in HEK-Blue mTLR2 cells. FIG. 11J: Dendritic-like cells (DC2.4) activation and T helper (Th) cells stimulation potential determined by MHCII upregulation measured in FACS with anti-MHCII PE-Cyanine5. Non-fluorescent rods were assembled in LPS-free Tris buffer (50 mM, pH 7.4) under continuous rotary agitation for 72 hours at a concentration of $1.5\times10^{-3}$ M. The significance of the differences observed compared to the control was evaluated according to the one-way ANOVA Tukey's multiple-comparison test (*) 0.01; () 0.001; (*) 0.0001; (****)<0.0001.

FIGS. 12A-D show that M2e-NRs subcutaneous vaccination induced a specific IgG immune response against M2e. FIG. 12A: Immunization timeline. BALB/c mice were immunized s.c. and received two boosts at 2-week intervals. M2e-specific serum IgG antibody kinetics (FIG. 12B) and final titers (FIG. 12C). FIG. 12D: Levels of IgG isotypes in sera from immunized mice. Rods were assembled in LPS-free Tris buffer (50 mM, pH 7.4) under continuous rotary agitation for 72 hours at a concentration of $1.5\times10^{-3}$ M. Mice were immunized with M2e epitope (50 nmol) and different concentrations (10, 50 and 100 nmol) of rods with or without Alum, as indicated. The significance of the differences observed between each curve was evaluated according to the one-way ANOVA Tukey's multiple-comparison test (*) 0.01; () 0.001; (*) 0.0001; (****) <0.0001.

FIG. 13A: Immunization and challenge timeline. BALB/c mice were immunized by the intra-nasal (i.n.) route and received two boosts at 2-week intervals. Two weeks after the last boost immunization, mice were lightly anesthetized and inoculated i.n. with $5\times10^4$ PFU of PR8 virus. FIG. 13B: Clinical scores of infected mice rated from 0 to 3 as described in Materials and Methods (left panel); mean weight curves of infected mice values expressed as a percentage of initial weight at day of inoculation (100%) (middle panel); survival percentage curves of infected mice in each immunization group (n=8) (right panel). Plotted data are means±SEM (FIGS. 13B and D). FIG. 13C: Viral load in bronchoalveolar lavages. FIG. 13D: Levels of IgA (left) and IgG (right) subclasses in bronchoalveolar lavages from immunized mice before and after infection. Rods were assembled in LPS-free Tris buffer (50 mM, pH 7.4) under continuous rotary agitation for 72 hours at a concentration of $1.5\times10^{-3}$ M. Mice were immunized with M2e epitope (50 nmol) and different concentrations (10, 50 and 100 nmol) of rods with or without 5% of montanide gel (MG), as indicated. The significance of the differences observed compared to the control was evaluated according to the one-way ANOVA Tukey's multiple-comparison test (*) 0.01; () 0.001; (*) 0.0001; (**)<0.0001. The log rank Mantel-Cox test was used to compare survival curves (n=4 to 8 per experimental group), (**) P<0.0001.

FIG. 14C: Levels of IgG isotypes in sera from immunized mice. Rods were assembled in LPS-free Tris buffer (50 mM, pH 7.4) under continuous rotary agitation for 72 hours at a concentration of $1.5\times10^{-3}$ M. Mice were immunized with M2e epitope (50 nmol) and different concentrations (10, 50 and 100 nmol) of rods with or without 5% of montanide gel (MG), as indicated. The significance of the differences observed between M2e-NRs curves and each of the other curves was evaluated according to the one-way ANOVA Tukey's multiple-comparison test (*) 0.01; () 0.001; (*) 0.0001; (****)<0.0001.

DISCLOSURE OF INVENTION

Figure 1:
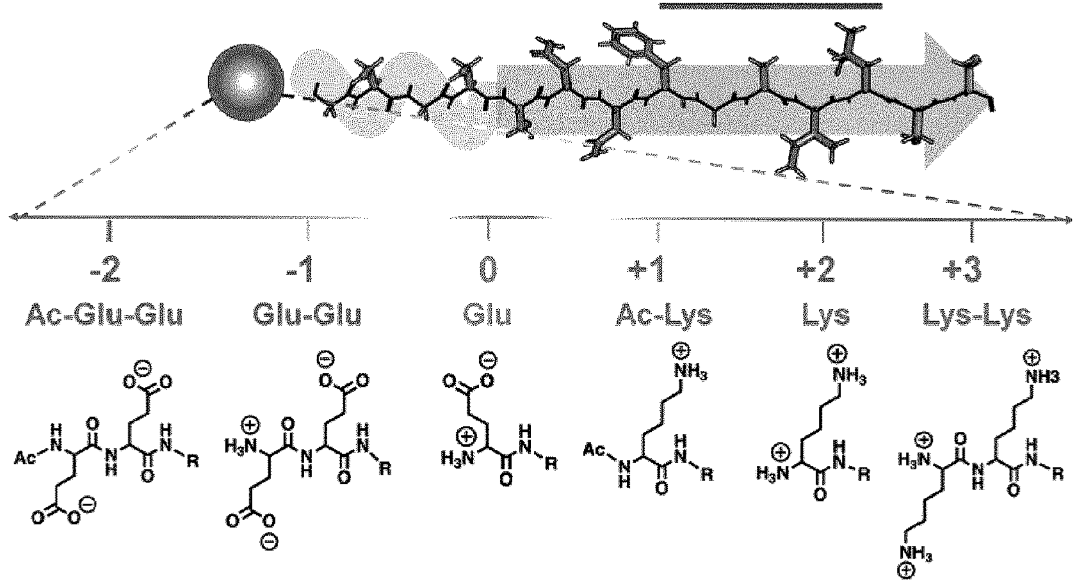
FIG. 1 shows the design of N-capped peptides. Peptide sequence GSGSSNNFGAILSS (SEQ ID NO:12) with the $I_{10}$ amyloid core (SNNFGAILSS, (SEQ ID NO:1)) and the flexible linker (GSGS, SEQ ID NO:4). The amyloidogenic FGAIL (SEQ ID NO:7) sequence is underlined. All peptides have a C-terminal amidation.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

The use of any and all examples, or exemplary language (e.g., "such as") provided herein, is intended merely to better illustrate the invention and does not pose a limitation on the scope of the invention unless otherwise claimed.

No language in the specification should be construed as indicating any non-claimed element as essential to the practice of the invention.

Herein, the term "about" has its ordinary meaning. The term "about" is used to indicate that a value includes an inherent variation of error for the device or the method being employed to determine the value, or encompass values close to the recited values, for example within 10% or 5% of the recited values (or range of values).

Unless otherwise defined, all technical and scientific terms used herein have the same meaning as commonly understood by one of ordinary skill in the art to which this invention belongs.

In the studies described herein, the present inventors have shown that the addition of positive capping units made of lysine residues at the N-terminal end of the β-sheet-forming sequence derived from the 20-29 segment of islet amyloid polypeptide (IAPP) leads to the formation of uniform nanorod-like assemblies. The positively-capped assemblies present an advantageous safety profile due to non-amyloid properties, and were shown to be cytocompatible. Fusion of these positively-capped self-assembling domain to a model peptide antigen (the M2e epitope of the influenza A virus) did not affect the formation and morphology of nanorods.

This construct, which presents morphological characteristics suitable for vaccination (short length that should allow a greater draining to the lymph nodes and high morphological uniformity that should facilitate biological and immunological characterizations), was shown to induce a protective anti-M2e immune response in animal models of influenza infection.

Accordingly, the present disclosure provides a self-assembling of the formula: $X^1$-$X^2$-$L^1$-Z, wherein $X^1$ is a lysine residue or an analog thereof comprising a primary amine in its side chain, or is absent; $X^2$ is a lysine residue or an analog thereof comprising a primary amine in its side chain; $L^1$ is a linker, preferably a peptide of 2 to 8 amino acids; Z is a self-assembling amyloid peptide.

The present disclosure also provides a construct, such as an immunogenic construct, comprising:

i) a self-assembling domain of the formula: $X^1$-$X^2$-$L^1$-Z wherein
  - $X^1$ is an amino acid or analog thereof having a side chain with a positive charge, preferably a lysine residue or an analog thereof comprising a primary amine in its side chain, or is absent;
  - $X^2$ is an amino acid or analog thereof having a side chain with a positive charge, preferably a lysine residue or an analog thereof comprising a primary amine in its side chain;
  - $L^1$ is a peptide linker of 2 to 8 amino acids;
  - Z is a self-assembling amyloid (β-sheet) peptide; and ii) a molecule, such as an antigen, conjugated to the self-assembling domain, wherein the construct is not a naturally-occurring protein or polypeptide.

The term self-assembling amyloid peptide as used herein refers to peptides whose chemical properties are such that they spontaneously aggregate in vitro or in vivo, assuming parallel or antiparallel beta sheet configurations. Example of self-assembling amyloid peptide include fragments of the islet amyloid polypeptide (IAPP) such as the 20-29 fragment (SNNFGAILSS, SEQ ID NO:1), In an embodiment, the self-assembling amyloid peptide adopts a cross-β-sheet assembly configuration, which is characterized by stack of β-sheets oriented perpendicularly to the fibril axis. In an embodiment, the self-assembling amyloid peptide adopts a parallel β-sheet configuration.

The self-assembling amyloid peptide has preferably a length of 3, 4 or 5 to 50, 40 or 30 amino acids, for example a length of 5 to 30, 5 to 25, 5 to 20 or 5 to 15 amino acids.

In an embodiment, the self-assembling amyloid peptide comprises or consists of the sequence SNNFGAIL (SEQ ID NO:2) or a variant thereof having at least 70% identity with the sequence SNNFGAIL (SEQ ID NO:2), i.e. having no more than 2 mutations/substitutions relative to the sequence SNNFGAIL (SEQ ID NO:2). In another embodiment, the self-assembling amyloid peptide comprises or consists of the sequence SNNFGAIL (SEQ ID NO:2) or a variant thereof having at least 85% identity with the sequence SNNFGAIL (SEQ ID NO:2), i.e. having 1 mutation/substitution relative to the sequence SNNFGAIL (SEQ ID NO:2). In another embodiment, the self-assembling amyloid peptide comprises or consists of the sequence SNNFGAIL (SEQ ID NO:2).

In another embodiment, the self-assembling amyloid peptide comprises or consists of the sequence SNNFGAILS (SEQ ID NO:3) or a variant thereof having at least 70% identity with the sequence SNNFGAILS (SEQ ID NO:3), i.e. having no more than 2 mutations/substitutions relative to the sequence SNNFGAILS. In another embodiment, the self-assembling amyloid peptide comprises or consists of the sequence SNNFGAILS (SEQ ID NO:3) or a variant thereof having at least 85% identity with the sequence SNNFGAILS (SEQ ID NO:3), i.e. having 1 mutation/substitution relative to the sequence SNNFGAILS (SEQ ID NO:3). In another embodiment, the self-assembling amyloid peptide comprises or consists of the sequence SNNFGAILS (SEQ ID NO:3)

In another embodiment, the self-assembling amyloid peptide comprises or consists of the sequence SNNFGAILSS (SEQ ID NO:1) or a variant thereof having at least 70% identity with the sequence SNNFGAILSS (SEQ ID NO:1), i.e. having no more than 3 mutations/substitutions relative to the sequence SNNFGAILSS (SEQ ID NO:1). In another embodiment, the self-assembling amyloid peptide comprises or consists of the sequence SNNFGAILSS (SEQ ID NO:1) or a variant thereof having at least 80% identity with the sequence SNNFGAILSS (SEQ ID NO:1), i.e. having no more than 2 mutations/substitutions relative to the sequence SNNFGAILSS (SEQ ID NO:1). In another embodiment, the self-assembling amyloid peptide comprises or consists of the sequence SNNFGAILSS (SEQ ID NO:1) or a variant thereof having at least 90% identity with the sequence SNNFGAILSS (SEQ ID NO:1), i.e. having 1 mutation/substitution relative to the sequence SNNFGAILSS (SEQ ID NO:1). In another embodiment, the self-assembling amyloid peptide comprises or consists of the sequence SNNFGAILSS (SEQ ID NO:1).

The self-assembling domain may comprise L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of peptides. Examples of naturally-occurring amino acids are glycine, alanine, valine, leucine, isoleucine, serine, threonine, etc. Other amino acids include for example non-genetically encoded forms of amino acids, as well as a conservative substitution of an L-amino acid. Naturally-occurring non-genetically encoded amino acids include, for example, beta-alanine, 3-amino-propionic acid, 2,3-diamino propionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (Hoarg), N-acetyl lysine, 2-amino butyric acid, 2-amino butyric acid, 2,4,-diaminobutyric acid (D- or L-), p-aminophenylalanine, N-methylvaline, homocysteine, homoserine (HoSer), cysteic acid, epsilon-amino hexanoic acid, delta-amino valeric acid, or 2,3-diaminobutyric acid (D- or L-), etc. These amino acids are well known in the art of biochemistry/peptide chemistry.

The above-noted self-assembling domain may comprise all L-amino acids, all D-amino acids or a mixture of L- and D-amino acids. As such, the single-letter code for designing amino acids in the above-noted formula encompass both the L- and D-isomers of the recited amino acids (for those having a chiral center). For example, the letter "N" refers to L-asparagine and D-asparagine. In an embodiment, the self-assembling domain comprises only L-amino acids.

"Identity" refers to sequence similarity/identity between two polypeptide molecules. The identity can be determined by comparing each position in the aligned sequences. A degree of identity between amino acid sequences is a function of the number of identical amino acids at positions shared by the sequences. As used herein, a given percentage of identity between sequences denotes the degree of sequence identity in optimally aligned sequences.

Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, WI, U.S.A.). Sequence similarity or identity may also be determined using the BLAST algorithm, described in Altschul et al., 1990, *J. Mol. Biol.* 215: 403-10 (using the published default settings). Software for performing BLAST analysis may be available through the National Center for Biotechnology Information web site. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance.

“Variant” as used herein refers to a self-assembling peptide in which one or more of the amino acids of the native sequence has/have been modified, but which retains adjuvant, immunostimulatory and/or immunopotentiating activity. The modification may be, for example, a deletion of one or more consecutive or non-consecutive amino acids, a substitution of amino acids, one or more substitution(s) of a naturally occurring amino acid (L-amino acid) by a corresponding D-amino acid, an extension of the sequence by e.g., one, two, three or more amino acids. In an embodiment, the above-mentioned substitution(s) are conserved amino acid substitutions. As used herein, the term “conserved amino acid substitutions” (or sometimes “conservative amino acid substitutions”) refers to the substitution of one amino acid for another at a given location in the self-assembling peptide, where the substitution can be made without substantial loss of the relevant structure/function (e.g., ability to self-aggregate). In making such changes, substitutions of like amino acid residues can be made on the basis of relative similarity of side-chain substituents, for example, their size, charge, hydrophobicity, hydrophilicity, and the like, and such substitutions may be assayed for their effect on the structure/function of the self-assembling peptide by routine testing.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6) are assigned to amino acid residues (as detailed in U.S. Pat. No. 4,554,101): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In other embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In other embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In other embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Biol.* 179: 125-142, 1984). Genetically encoded hydrophobic amino acids include Gly, Ala, Phe, Val, Leu, lie, Pro, Met and Trp, and genetically, encoded hydrophilic amino acids include Thr, His, Glu, Gln, Asp, Arg, Ser, and Lys.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents.

An apolar amino acid is a hydrophobic amino acid with a side chain that is uncharged at physiological pH and which has bonds in which a pair of electrons shared in common by two atoms is generally held, equally by each of the two atoms (i.e., the side chain is not polar). Genetically encoded apolar amino acids include Gly, Leu, Val, lie, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and lie.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

The above classifications are not absolute, and an amino acid may be classified in more than one category. In addition, amino acids can be classified based on known behavior and or characteristic chemical, physical, or biological properties based on specified assays or as compared with previously identified amino acids. Amino acids can also include bifunctional moieties having amino acid-like side chains.

Conservative changes can also include the substitution of a chemically-derivatized moiety for a non-derivatized residue, by for example, reaction of a functional side group of an amino acid.

In addition to the substitutions outlined above, synthetic amino acids providing similar side chain functionality can also be introduced into the self-assembling peptide. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-p-cyano-phenylalanine, D- or L-(4-isopropyl)-phenylglycine, D- or L-(trifluoromethyl)-phenylglycine, D- or L-(trifluoromethyl)-phenylalanine, D- or L-p-fluorophenylalanine, D- or L-p-biphenylalanine, D- or L-p-methoxybiphenylalanine, D- or L-2-indole(alkyl)alanines, and D- or L-alkylalanines wherein the alkyl group is selected from the group consisting of substituted or unsubstituted methyl, ethyl, propyl, hexyl, butyl, pentyl, isopropyl, iso-butyl, and iso-pentyl.

In an embodiment, the phenylalanine residue(s) present in the self-assembling peptide/domain may be replaced a phenylalanine analog. Analogs of phenylalanine include, for example, β-methyl-phenylalanine, β-hydroxyphenylalanine, α-methyl-3-methoxy-DL-phenylalanine, α-methyl-D-phenylalanine, α-methyl-L-phenylalanine, 2,4-dichloro-phenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2,4,5-trihydroxy-phenylalanine, 3,4,5-trifluoro-d-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-cyano-D-phenylalanine, 3-cyano-L-phenylalanine, 3-fluoro-D-phenylalanine, 3-fluoro-L-phenylalanine, 3-iodo-D-phenylalanine, 3-iodo-L-phenylalanine, 3-methyl-D-phenylalanine, 3-methyl-L-phenylalanine, 3-nitro-D-phenylalanine, 3-nitro-L-phenylalanine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-D-phenylalanine, 4-iodo-D-phenylalanine, 4-iodo-L-phenylalanine, homophenylalanine, 1,2,3,4-tetrahydroisoquinoline-3-carboxylic acid (Tic), and 3,3-diphenylalanine. Also, phenylalanine residues may be substituted with tyrosine residues and vice versa.

Analogs of lysine comprising a primary amine in their side chain include ornithine, homolysine, 2,3-diaminoprorionic acid (Dap), and 2,4-diaminobutyric acid (Dab).

In an embodiment, $X^1$ and/or $X^2$ is/are independently a lysine residue. In another embodiment, $X^1$ and/or $X^2$ is/are independently a lysine analog comprising a primary amine in its side chain, such as Dab. In an embodiment, $X^1$ is a lysine residue. In another embodiment, X2 is a lysine residue.

Other modifications are also included within the definition of variant of the self-assembling peptide of the present disclosure. For example, the size of the self-assembling peptide can be reduced by deleting one or more amino acids, and/or amino acid mimetics or dipeptide mimics containing non-peptide bonds may be used. Examples of using molecular scaffolds such as benzodiazepine, azepine, substituted gamma lactam rings, keto-methylene pseudopeptides, β-turn dipeptide cores and p-aminoalcohols for these purposes are known to peptide chemists and are described in for example *Peptidomimetic protocols* (Methods in molecular medicine Vol. 23) W. M. Kazmierski (ed.), Humana Press and *Advances in Amino Acid Mimetics and Peptidomimetics, Vols.* 1 & 2, A. Abell (Ed).

By "molecule" is meant any chemical compound (synthetic or natural), biomolecule (e.g., peptide, polypeptide, protein, sugar, polysaccharide, lipid, glycolipid, phospholipid, nucleic acid, antibody, etc.), polymer, etc. that may be conjugated to the self-assembling amyloid peptide to mediate a desired effect. In an embodiment, the molecule is an antigen or an immunostimulatory molecule such as a TLR agonist, an adjuvant, a cytokine, or a chemokine.

By "antigen" is meant a molecule that is capable of stimulating a host's immune system to make a cellular antigen-specific immune response and/or a humoral antibody response when the antigen is presented/administered. It refers to any natural or synthetic compound or chemical entity (lipids, phospholipids, glycolipids, saccharides, nucleic acids, etc.) capable of stimulating a immune response in a host. In an embodiment, the antigen is a polypeptide (e.g., a protein or peptide derived from a pathogen or a tumor cell). A polypeptide antigen may contain one or more epitope(s). Normally, an epitope will include between about 3-15, generally about 5-15, amino acids. Epitopes of a given protein can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N. J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance (NMR). See, e.g., Epitope Mapping Protocols, supra. "Antigen" also refers to any natural or synthetic compound or chemical entity (lipids, phospholipids, glycolipids, saccharides, nucleic acids, etc.) capable of stimulating an immune response in a host. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide that expresses an immunogenic protein, or antigenic determinant in vivo, such as in nucleic acid immunization applications, is also included in the definition of antigen herein. The antigenic polynucleotide can be delivered through two major routes, either using a viral or bacterial host as gene delivery vehicle (live vaccine vector) or administering the gene in a free form, e.g., inserted into a plasmid (DNA vaccine). Viral and bacterial vaccine vectors are well known in the art (see New Generation Vaccines, 3rd edition, 2004 and Vaccine Protocols, 2nd edition, Humana Press, 2003) and include, for example, Poxvirus, adenovirus, Measles virus, alphavirus, Yellow Fever virus, Semliki Forest virus, poliovirus, herpex simplex virus, vesicular stomatitis virus, *Listeria monocytogenes, Salmonella* and *Shigella*. The vaccine vector contains a polynucleotide antigen that is placed under the control of elements required for expression.

The antigen may be derived from a microorganism or pathogen affecting non-human animals such as pets (cats, dogs) or farm animals (pig, cow, horse, poultry, etc.), or humans. In an embodiment, the antigen is derived from a human pathogen (e.g., a bacteria or a virus affecting humans), or is from human origin (such as a human polypeptide or a fragment thereof).

Further, for purposes of the present disclosure, antigens (e.g., polypeptides or other biomolecules) can be derived from any of several known pathogens, such as viruses, bacteria, parasites and fungi, as well as any of the various tumor antigens. The antigen may also be an antigen involved in diseases or conditions for which vaccination may be useful, e.g., certain allergies and/or immune/inflammation disorders.

The immunogenic construct or composition of the present disclosure contains an antigen capable of eliciting an immune response against a pathogen, such as an animal or human pathogen, which antigen may be derived from Human Immunodeficiency virus (HIV), such as Tat, Nef, Gag, Pol, gp120 or gp160, human herpes viruses, such as gD or derivatives thereof or Immediate Early protein such as ICP27 from HSV1 or HSV2, cytomegalovirus (such as gB or derivatives thereof), Rotavirus, Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g. Yellow Fever Virus, Dengue Virus, Tick-borne encephalitis virus, Japanese Encephalitis Virus), Influenza virus (e.g., HA, NP, NA, or M proteins, or fragments thereof, or combinations thereof), or coronaviruses (e.g., a SARS-CoV-2 antigen, such as the spike (S) glycoprotein or fragments thereof).

Antigens can also be derived from bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi; Moraxella* spp, including *M catarrhalis*, also known as Branhamella *catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, —B or —C, Th Ra12, Tb H9, Tb Ra35, Tb38-1, Erd 14, DPV, MTI, MSL, mTTC2 and hTCC1), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp., including *H. pylori* (for example urease, catalase, vacuolating toxin); *Pseudomonas* spp., including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphthe-*

*riae* (for example diphtheria toxin and derivatives thereof); *Borrelia* spp., including *B. burgdorferi* (for example OspA, OspC, DbpA, DbpB), *B. garinii* (for example OspA, OspC. DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp. including *C. trachomatis* (for example MOMP, heparin-binding proteins), *C. pneumoniae* (for example MOMP, heparin-binding proteins), *C. psittaci*; Leptospira spp., including L. interrogans; *Treponema* spp., including *T. pallidum* (for example the rare outer membrane proteins), *T. denticola, T. hyodysenteriae*; or derived from parasites such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leishmania* spp., including *L. major, Pneumocystis* spp., including *P. carinii; Trichomonas* spp., including *T. vaginalis; Schisostoma* spp., including *S. mansoni*, or derived from yeast such as *Candida* spp., including *C. albicans; Cryptococcus* spp., including *C. neoformans, Streptococcus* spp., including *S. pneumoniae* (for example capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25: 337-342), and mutant detoxified derivatives thereof (WO 90/06951; WO 99/03884), antigens derived from *Haemophilus* spp., including *H. influenzae* type B (for example PRP and conjugates thereof), non-typeable *H. influenzae*, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

The immunogenic construct or composition of the present disclosure may also comprise a tumor antigen and be useful for the prevention or immunotherapeutic treatment of cancers. For example, the immunogenic construct or composition may include tumor rejection antigens such as those for prostate, breast, colorectal, lung, pancreatic, renal or melanoma cancers. Exemplary antigens include MAGE 1, 3 and MAGE 4 or other MAGE antigens, PRAME, BAGE, LAGE (also known as NY-Eos-1) SAGE and HAGE or GAGE. Such antigens are expressed in a wide range of tumor types such as melanoma, lung carcinoma, sarcoma and bladder carcinoma. Other tumor-specific antigens that may be included in the immunogenic construct or composition of the present disclosure include, but are not restricted to tumor-specific gangliosides such as GM2, and GM3 or conjugates thereof to carrier proteins; or said antigen may be a self-peptide hormone such as whole length Gonadotrophin hormone releasing hormone, a short 10 amino acid long peptide, useful in the treatment of many cancers. Prostate antigens can also be included, such as Prostate specific antigen (PSA), PAP, STEAP, PSCA, PCA3, PSMA or Prostase. Other tumor-associated antigens (TAA) useful in the context of the present disclosure include: Carcinoembryonic antigen (CEA), KSA (also known as EpCAM), gp100, Plu-1, HASH-1, HasH-2, Cripto, Criptin. Additionally, antigens particularly relevant for vaccines in the therapy of cancer also comprise tyrosinase and survivin. Other antigens include Mucin-derived peptides such as Muc1, for example Muc1-derived peptides that comprise at least one repeat unit of the Muc1 peptide, preferably at least two such repeats and which is recognized by the SM3 antibody. Other mucin-derived peptides include peptides from Muc5.

The immunogenic construct or composition may comprise antigens associated with tumor-support mechanisms (e.g., angiogenesis, tumor invasion), for example Angiopoietin (Ang)-1 and -2, tyrosine kinase with immunoglobulin and epidermal growth factor homology domains (Tie)-2 as well as vascular endothelial growth factor (VEGF).

The immunogenic construct or composition of the present disclosure may be used for the prophylaxis or therapy of allergy. Such immunogenic construct or composition would comprise allergen-specific (for example Der p1 and Der p5) and allergen non-specific antigens (for example peptides derived from human IgE, including but not restricted to the Stanworth decapeptide). Other antigens include for example antigens derived from *Aspergillus fumigatus.*

In an embodiment, the antigen is a peptide or a polypeptide, preferably a peptide or a polypeptide of 500 amino acids or less. In an embodiment, the antigen is a peptide or polypeptide of 400, 350, 300, 250, 200, 150, 100, 90. 80, 70, or 60 amino acids or less. In another embodiment, the antigen is a peptide of 50, 45, 40, 35 or 30 amino acids or less. In an embodiment, the antigen is a peptide or polypeptide comprising at least 5, 6, 7, 8, 9, or 10 amino acids. In a further embodiment, the antigen is a peptide of 10 to 50 amino acids, 15 to 40 amino acids or 15 to 30 amino acids.

The molecule (e.g., antigen) may be conjugated to the self-assembling domain directly or indirectly through a linker $L^2$. For example, the antigen may be fused directly to the N-terminal end of the self-assembling domain, i.e. to the N-terminal lysine residue. In another embodiment, a peptide/polypeptide linker may be inserted between the antigen and the N-terminal end of the self-assembling domain. When the antigen is fused directly to the N-terminal end of the self-assembling domain or indirectly through a peptide/polypeptide linker, the immunogenic construct may be synthesized as a fusion polypeptide. The molecule (e.g., antigen) may alternatively be chemically conjugated to the self-assembling domain after synthesis of the self-assembling domain, e.g. before or after self-assembly into a nanostructure (e.g., nanorod).

In another embodiment, the antigen may be conjugated/attached to the side chain of one the amino acids of the self-assembling domain. Methods for conjugating moieties to side-chains of amino acids are well known in the art. For example, chemical groups that react with primary amines ($—NH_2$) present in the side-chain of lysine residues such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters may be used to conjugate the antigen to the self-assembling domain. Most of these groups conjugate to amines by either acylation or alkylation. Cysteine residues present in the self-assembling domain may also be used to attach the antigen.

The linkers $L^1$ and/or $L^2$ of the construct may independently be a peptide/polypeptide linker comprising one or more amino acids or another type of chemical linker (e.g., a carbohydrate linker, a lipid linker, a fatty acid linker, a polyether linker, PEG, etc. having suitable flexibility and stability to allow the immunogenic construct to adopt a proper conformation, e.g., a nanorod structure. In an embodiment, the linker is a peptide/polypeptide linker. In an embodiment, the peptide/polypeptide linker comprises at least 2 amino acids, and preferably comprises at least 3 or 4 amino acids. The linker may comprise about 100, 90, 80, 70, 60 or 50 amino acids or less, and preferably 20, 15 or 10 amino acids or less. In a further embodiment, the peptide/polypeptide linker $L^1$ and/or $L^2$ comprises about 2 to about 10 amino acids, for example about 2 to about 8 amino acids or about 2 to about 7 amino acids, for example about 2 to about 6 or 5 amino acids. In a further embodiment, the linker $L^1$ and/or $L^2$ comprises from 3 to 5 amino acids, preferably 3 or 4 amino acids. In an embodiment, the peptide/polypeptide linker $L^1$ and/or $L^2$ is enriched in glycine residues that are known to favor linker flexibility. In an embodiment, the peptide/polypeptide linker $L^1$ and/or $L^2$ comprises one or more serine (Ser or S) and/or threonine (Thr or T) residues, preferably serine residues, which are known to favor linker solubility. In another embodiment, the peptide/polypeptide linker $L^1$ and/or $L^2$ comprises the sequence GSG. In another embodiment, the peptide/polypeptide linker $L^1$ and/or $L^2$ comprises the sequence GSGS (SEQ ID NO:4).

In embodiments, the above-mentioned self-assembling domain may comprise, further to the domain defined above, one more amino acids (naturally occurring or synthetic) covalently linked to the amino- and/or carboxy-termini of said domain. In an embodiment, the above-mentioned cyclic peptide comprises up to 5 additional amino acids at the N- and/or C-termini to the domain defined above. In further embodiments, the above-mentioned self-assembling domain comprises up to 5, 4, 3, 2, or 1 additional amino acids at the N- and/or C-termini of the domain defined above. In an embodiment, the above-mentioned self-assembling domain consists of the domain defined above.

The self-assembling domain or construct described herein may further comprise one or more modifications that confer additional biological properties to the immunogenic construct such as protease resistance, plasma protein binding, increased plasma half-life, intracellular penetration, etc. Such modifications include, for example, covalent attachment of molecules/moiety to the immunogenic construct such as fatty acids (e.g., $C_6$-$C_{18}$), attachment of proteins such as albumin (see, e.g., U.S. Pat. No. 7,268,113); sugars/polysaccharides (glycosylation), biotinylation or PEGylation (see, e.g., U.S. Pat. Nos. 7,256,258 and 6,528,485). The immunogenic construct may also be conjugated to a molecule that increases its immunogenicity, including carrier proteins such as keyhole limpet hemocyanin (KLH), bovine serum albumin (BSA), human serum albumin (HSA) and ovalbumin (OVA), and/or polysaccharides. In an embodiment, the immunogenic construct is conjugated to a carrier protein. In an embodiment, the carrier protein is conjugated via a disulfide bond to immunogenic construct. The above description of modification of the immunogenic construct does not limit the scope of the approaches nor the possible modifications that can be engineered.

The self-assembling domain or construct described herein may be in the form of a salt, e.g., a pharmaceutically acceptable salt. As used herein the term "pharmaceutically acceptable salt" refers to salts of compounds that retain the biological activity of the parent compound, and which are not biologically or otherwise undesirable. Such salts can be prepared in situ during the final isolation and purification of the compound, or may be prepared separately by reacting a free base function with a suitable acid. Many of the self-assembling domains or immunogenic constructs disclosed herein are capable of forming acid and/or base salts by virtue of the presence of amino and/or carboxyl groups or groups similar thereto. Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, decanoate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, octanoate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid. benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid. Basic addition salts also can be prepared by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like. Salts derived from organic bases include, but are not limited to, salts of primary, secondary and tertiary amines.

The self-assembling domain or construct of the disclosure may be produced by expression in a host cell comprising a nucleic acid encoding the self-assembling domain or immunogenic construct (recombinant expression) or by chemical synthesis (e.g., solid-phase peptide synthesis). Peptides can be readily synthesized by manual and automated solid phase procedures well known in the art. Suitable syntheses can be performed for example by utilizing "t-Boc" or "Fmoc" procedures. Techniques and procedures for solid phase synthesis are described in for example Solid Phase Peptide Synthesis: A Practical Approach, by E. Atherton and R. C. Sheppard, published by IRL, Oxford University Press, 1989. Alternatively, the peptides may be prepared by way of segment condensation, as described, for example, in Liu et al., Tetrahedron Lett. 37: 933-936, 1996; Baca et al., J. Am. Chem. Soc. 117: 1881-1887, 1995; Tarn et al., Int. J. Peptide Protein Res. 45: 209-216, 1995; Schnolzer and Kent, Science 256: 221-225, 1992; Liu and Tarn, J. Am. Chem. Soc. 116: 4149-4153, 1994; Liu and Tarn, Proc. Natl. Acad. Sci. USA 91: 6584-6588, 1994; and Yamashiro and Li, Int. J. Peptide Protein Res. 31: 322-334, 1988). Other methods useful for synthesizing the peptides are described in Nakagawa et al., J. Am. Chem. Soc. 107: 7087-7092, 1985.

Self-assembling domains or constructs comprising only naturally occurring amino acids encoded by the genetic code may also be prepared using recombinant DNA technology using standard methods. Peptides produced by recombinant technology may be modified (e.g., N-terminal acylation [e.g., acetylation], C-terminal amidation), using methods well known in the art. Therefore, in embodiments, in cases where a self-assembling domain or immunogenic construct described herein contains naturally occurring amino acids encoded by the genetic code, the peptide may be produced using recombinant methods, and may in embodiments be subjected to for example the just-noted modifications (e.g., acylation, amidation). Accordingly, in another aspect, the disclosure further provides a nucleic acid encoding the above-mentioned self-assembling domain or immunogenic construct. The disclosure also provides a vector comprising the above-mentioned nucleic acid. In yet another aspect, the present disclosure provides a cell (e.g., a host cell) comprising the above-mentioned nucleic acid and/or vector. The disclosure further provides a recombinant expression system, vectors and host cells, such as those described above, for the expression/production of a self-assembling domain or construct of the disclosure, using for example culture media, production, isolation and purification methods well known in the art.

The self-assembling domain or construct of the disclosure can be purified by many techniques of peptide/polypeptide purification well known in the art, such as reverse phase chromatography, high performance liquid chromatography (HPLC), ion exchange chromatography, size exclusion chromatography, affinity chromatography, gel electrophoresis, and the like. The actual conditions used to purify a particular peptide or polypeptide will depend, in part, on synthesis strategy and on factors such as net charge, hydrophobicity, hydrophilicity, and the like, and will be apparent to those of ordinary skill in the art. For affinity chromatography purification, any antibody that specifically binds the peptide/polypeptide may for example be used.

As described in the examples below, the self-assembling domain or construct according to the present disclosure have the ability to self-assemble into rod-like structures (nanorods) when put under suitable conditions. Accordingly, in another aspect, the present disclosure provides a nanorods or plurality of nanorods comprising the self-assembling domain or immunogenic construct described herein. In an embodiment, the nanorods have a length of between about 100, 110 or 120 nm to about 160, 170, 180, 190 or 200 nm. In an embodiment, the plurality of nanorods have an average length of about 100 to about 200 nm±30-50 or 35-45 nm, for example about 120 to about 180 nm±30-50 or 35-45 nm, about 120±30-50 or 35-45 nm, about 130±30-50 or 35-45 nm, about 140±30-50 or 35-45 nm, about 150±30-50 or 35-45 nm, about 160±30-50 or 35-45 nm, about 170±30-50 or 35-45 nm, or about 180±30-50 or 35-45 nm.

The present disclosure also provides compositions, such as pharmaceutical compositions and vaccines, comprising the self-assembling domain, construct, nanorods or plurality of nanorods described herein. In an embodiment, the composition further comprises one or more pharmaceutically acceptable carriers, excipient, and/or diluents. In an embodiment, the composition (e.g., vaccine) further comprises a pharmaceutically acceptable vaccine adjuvant.

As used herein, "pharmaceutically acceptable" (or "biologically acceptable") refers to materials characterized by the absence of (or limited) toxic or adverse biological effects in vivo. It refers to those compounds, compositions, and/or dosage forms which are, within the scope of sound medical judgment, suitable for use in contact with the biological fluids and/or tissues and/or organs of a subject (e.g., human, animal) without excessive toxicity, irritation, allergic response, or other problem or complication, commensurate with a reasonable benefit/risk ratio.

The term "vaccine adjuvant" refers to a substance which, when added to an immunogenic agent such as an antigen (e.g., the immunogenic construct, nanorods or composition defined herein), non-specifically enhances or potentiates an immune response to the agent in the host upon exposure to the mixture. Suitable vaccine adjuvants are well known in the art and include, for example: (1) mineral salts (aluminum salts such as aluminum phosphate and aluminum hydroxide, calcium phosphate gels), squalene, (2) oil-based adjuvants such as oil emulsions and surfactant based formulations, e.g., incomplete or complete Freud's adjuvant, MF59 (microfluidised detergent stabilised oil-in-water emulsion), QS21 (purified saponin), AS02 [SBAS2](oil-in-water emulsion+MPL+QS-21), (3) particulate adjuvants, e.g., virosomes (unilamellar liposomal vehicles incorporating influenza haemagglutinin), AS04 ([SBAS4] aluminum salt with MPL), ISCOMS (structured complex of saponins and lipids), polylactide co-glycolide (PLG), (4) microbial derivatives (natural and synthetic), e.g., monophosphoryl lipid A (MPL), Detox (MPL+*M. Phlei* cell wall skeleton), AGP [RC-529](synthetic acylated monosaccharide), DC_Chol (lipoidal immunostimulators able to self-organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects), complete Freud's adjuvant (comprising inactivated and dried mycobacteria) (5) endogenous human immunomodulators, e.g., hGM-CSF or hIL-12 (cytokines that can be administered either as protein or plasmid encoded), Immudaptin (C3d tandem array) and/or (6) inert vehicles, such as gold particles.

An "excipient" as used herein has its normal meaning in the art and is any ingredient that is not an active ingredient (drug) itself. Excipients include for example binders, lubricants, diluents, fillers, thickening agents, disintegrants, plasticizers, coatings, barrier layer formulations, lubricants, stabilizing agent, release-delaying agents and other components. "Pharmaceutically acceptable excipient" as used herein refers to any excipient that does not interfere with effectiveness of the biological activity of the active ingredients and that is not toxic to the subject, i.e., is a type of excipient and/or is for use in an amount which is not toxic to the subject. Excipients are well known in the art, and the present disclosure is not limited in these respects. In certain embodiments, the composition of the present disclosure include excipients, including for example and without limitation, one or more binders (binding agents), thickening agents, surfactants, diluents, release-delaying agents, colorants, flavoring agents, fillers, disintegrants/dissolution promoting agents, lubricants, plasticizers, silica flow conditioners, glidants, anti-caking agents, anti-tacking agents, stabilizing agents, anti-static agents, swelling agents and any combinations thereof. As those of skill would recognize, a single excipient can fulfill more than two functions at once, e.g., can act as both a binding agent and a thickening agent. As those of skill will also recognize, these terms are not necessarily mutually exclusive. Examples of commonly used excipient include water, saline, phosphate buffered saline, dextrose, glycerol, ethanol, and the like, as well as combinations thereof. In many cases, it will be preferable to include isotonic agents, for example, sugars, polyalcohols, such as mannitol, sorbitol, or sodium chloride in the composition. Additional examples of pharmaceutically acceptable substances are wetting agents or auxiliary substances, such as emulsifying agents, preservatives, or buffers, which increase the shelf life or effectiveness.

The composition of the present disclosure may be formulated for administration via any conventional route, such as intravenous, oral, transdermal, intraperitoneal, subcutaneous, mucosal, intramuscular, intranasal, intrapulmonary, parenteral or topical administration. The preparation of such formulations is well known in the art (see, e.g., Remington: The Science and Practice of Pharmacy, Lippincott Williams & Wilkins; 21$^{st}$ edition, 2005). In an embodiment, the composition of the present disclosure is formulated for administration by injection, for example intravenous, subcutaneous or intramuscular administration.

The construct and nanorods, composition or vaccine defined herein may be used in biomedical applications.

In another aspect, the present disclosure also provides a method for delivering a molecule of interest (e.g., an antigen such as one or more of the antigens defined above) in a subject comprising administering to the subject an effective amount of the construct, nanorods, composition or vaccine defined herein.

In another aspect, the present disclosure also provides a method for inducing an immune response against an antigen (e.g., one or more of the antigens defined above) in a subject comprising administering to the subject an effective amount of the immunogenic construct, nanorods, composition or vaccine defined herein. The present disclosure also provides the use of the immunogenic construct, nanorods, composition or vaccine defined herein for inducing an immune response against an antigen (e.g., one or more of the antigens defined above) in a subject. The present disclosure also provides the use of the immunogenic construct, nanorods, composition or vaccine defined herein for the manufacture of a medicament for inducing an immune response against an antigen (e.g., one or more of the antigens defined above) in a subject. The present disclosure also provides the immunogenic construct, nanorods, composition or vaccine defined herein for inducing an immune response against an antigen (e.g., one or more of the antigens defined above) in a subject. The present disclosure also provides the immunogenic construct, nanorods, composition or vaccine defined herein for use as a medicament.

In another aspect, the present disclosure also provides a method for preventing and/or treating a microbial infection or cancer in a subject comprising administering to the subject an effective amount of the immunogenic construct, nanorods, composition or vaccine defined herein. The present disclosure also provides the use of the immunogenic construct, nanorods, composition or vaccine defined herein for preventing and/or treating a microbial infection or cancer in a subject. The present disclosure also provides the use of the immunogenic construct, nanorods, composition or vaccine defined herein for the manufacture of a medicament for preventing and/or treating a microbial infection or cancer in a subject. The present disclosure also provides the immunogenic construct, nanorods, composition or vaccine defined herein for use in preventing and/or treating a microbial infection or cancer in a subject.

Any suitable amount of the immunogenic construct, nanorods, composition or vaccine defined herein may be administered to a subject. The dosages will depend on many factors including the mode of administration. Typically, the amount of immunogenic construct, nanorods, composition or vaccine defined herein contained within a single dose will be an amount that effectively induces an immune response against an antigen, and/or prevent, delay or treat a microbial infection or cancer without inducing significant toxicity. For the prevention, treatment or reduction in the severity of a given disease or condition, the appropriate dosage of the compound/composition will depend on the type of disease or condition to be treated, the severity and course of the disease or condition, whether the compound/composition is administered for preventive or therapeutic purposes, previous therapy, the patient's clinical history and response to the compound/composition, and the discretion of the attending physician. The compound/composition is suitably administered to the patient at one time or over a series of treatments. Preferably, it is desirable to determine the dose-response curve in vitro, and then in useful animal models prior to testing in humans. The present disclosure provides dosages for the immunogenic construct and nanorods, and compositions/vaccines comprising same. For example, depending on the type and severity of the disease, about 1 μg/kg to to 1000 mg per kg (mg/kg) of body weight per day. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg, or may range between any two of the foregoing values. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The administration/use may be performed prophylactically, i.e., prior to the development of the infection or disease, or therapeutically in a subject suffering from a disease or infected with a pathogen.

MODE(S) FOR CARRYING OUT THE INVENTION

The present invention is illustrated in further details by the following non-limiting examples.

Example 1: Materials and Methods

Peptide Synthesis, Purification and Characterization. Peptides were synthesized on a Rink amide solid support using Fmoc chemistry, as previously described, leading to C-α-amidated peptides.[41] Pseudoproline dipeptide derivatives (EMD Millipore) were incorporated to facilitate the synthesis of chimeric peptides.[42-43] For fluorescein labeling, Fmoc-6-Ahx-OH was first coupled at the N-terminus peptide-resin using standard coupling conditions. After Fmoc removal by standard procedure in 20% piperidine, a solution containing fluorescein isothiocyanate (FITC, 1:1 eq.) in pyridine/DMF/DCM (12:7:5) was added and the mixture reacted overnight. Crude peptides were purified by reverse-phase high performance liquid chromatography. To increase solubility, peptides were dissolved in 10% acetic acid (v/v) before being injected on a preparative C18 column using a linear gradient of acetonitrile in $H_2O$/TFA (0.6% v/v). Collected fractions were analyzed and characterized by liquid chromatography coupled with high-resolution mass spectrometry. Fractions corresponding to the desired peptide with purity higher than 95% were pooled and lyophilized.

Peptide Self-Assembly. Freshly lyophilized peptides were solubilized at $1.5\times10^{-3}$ M, unless otherwise specified, in endotoxin-free Tris-HCl (50 mM, pH 7.4) and sonicated for 5 min. Self-assembly was performed for 72 h at room temperature (RT) under rotary agitation at 40 rpm. Fluorescent nanorods were prepared at $1.5\times10^{-3}$ M with a molar ratio of 1:7 (FITC-M2e-NRs: NRs) in endotoxin-free Tris-HCl (50 mM, pH 7.4), 1% DMSO under the same conditions. LPS quantification was performed using a Limulus amebocyte lysate detection assay[36] (Associates of Cape Cod, Inc.) and all preparations contained <0.03 EU/mL. According to FDA recommendation (threshold of 0.5 EU/mL for vaccination in humans), these solutions were considered LPS-free and used for in vitro and in vivo experiments.[44]

Transmission Electron Microscopy. Peptide solutions were diluted at $0.5\times10^{-6}$ M in Tris-HCl before being applied to glow-discharged carbon films on 400 mesh copper grids. After adsorption, samples were negatively stained with 1.5% uranyl formate for 1 min and air dried for 15 min. Images were recorded using a FEI Tecnai G2 Spirit Twin microscope operating at 120 kV and equipped with a Gatan Ultrascan 4000 4 k×4 k CCD Camera. For quantification, the length and width of at least 300 individual fibrils (Fiji Image J software) per experiment were plotted as a frequency distribution.

Nanorod Cryotransmission Electron Microscopy. 3.6 μL of peptide solution ($400\times10^{-6}$ m) was applied to a holey carbon film supported on a TEM copper grid within a vitrification system (FEI Vitrobot). Sample was immersed in liquid ethane cooled by liquid nitrogen. Imaging was performed using a FEI Tecnai G2 F20 200 kV Cryo-STEM. During analysis, the cryoholder temperature was maintained below −170° C. to prevent sublimation of vitreous water. Images were recorded digitally with a CCD camera.

Atomic Force Microscopy. Peptide assemblies were diluted at $0.5\times10^{-6}$ M in 1% acetic acid and immediately applied to freshly cleaved mica. The mica was washed twice with deionized water and air-dried for 24 h. Samples were analyzed using a Veeco/Bruker Multimode AFM using scan assist with a silicon tip (2-12 nm tip radius, 0.4 N $m^{-1}$ force constant) on a nitride lever. Images were taken at 0.5 Hz and 1024 line $min^{-1}$. For quantification, the length of at least 300 individual fibrils per experiment were plotted as a frequency distribution.

Absorbance and Dynamic Light Scattering. Absorbance was measured at 400 and 600 nm using a NanoDrop™ 2000/2000c Spectrophotometer. Hydrodynamic radius was measured using a Malvern ZetaPlus instrument with 1 cm length disposable acrylic cells at room temperature. The refractive index (RI) value used for the solvent was 1.33 at 589 nm and the viscosity of the sample was assumed to be 4.0 cp. For each experiment, 3 measurements were recorded, and each measurement corresponds to 10 runs of 10 seconds.

Zeta Potential. Measurements were carried out using a ZetaPlus zeta potential analyzer (Brookhaven instruments corporation) operated at room temperature. Each measurement corresponded to a triplicate of 10 runs per analysis.

Critical Aggregation Concentration. Pyrene was solubilized in ethanol at $1\times10^{-3}$ M and then diluted in Tris-HCl $50\times10^{-3}$ M, pH 7.4. Peptides were solubilized into pyrene solution, keeping the pyrene concentration at $2\times10^{-6}$ M. The excitation wavelength was set at 335 nm and the emission spectra from 350 to 450 nm were recorded. CAC was determined by plotting the ratio of fluorescence intensity (373 nm/384 nm) as function of the concentration. Intersection of the two linear fits was used to determine the CAC. Pyrene fluorescence was measured in an ultra-micro 10 mm length cell using a PTI QuantaMaster spectrofluorometer.[45]

Circular Dichroism Spectroscopy. Peptide assemblies were diluted at $1.5\times10^{-6}$ M and transferred into a 1 mm path length quartz cell. Far-UV CD spectra were recorded from 190 to 260 nm using a Jasco J-815 CD spectrometer at room temperature. The wavelength step was set at 0.5 nm with a scan rate of 20 nm $min^{-1}$. Each collected spectrum was background subtracted with peptide-free buffer. The raw data was converted to mean residue ellipticity (MRE). Thermal unfolding transitions were monitored by the variation of CD signal at 222, 212, and 205 nm between 22 and 104° C. with a heating rate of 0.8° C. $min^{-1}$. Transitions were evaluated using a nonlinear least square fit assuming a two-state model (assembled and unassembled). Thermal unfolding curves were fitted to a two-state mode.[46]

Thioflavin T Fluorescence Spectroscopy. ThT fluorescence was measured in an ultramicro 10 mm length cell using a PTI QuantaMaster spectrofluorometer. The excitation wavelength was set at 440 nm and the emission spectra from 450 to 550 nm was recorded in presence of $40\times10^{-6}$ m ThT.

Attenuated Total Reflectance-Fourier Transform Infrared Spectroscopy. ATR-FTIR Spectra were recorded using a Nicolet Magna 560 spectrometer equipped with a nitrogen-cooled MCT detector. Each spectrum was an average of 128 scans recorded at a resolution of 2 $cm^{-1}$ using a Happ-Genzel apodization. Data analysis was performed using Grams/Al 8.0 software, as previously described[58].

PowderX-Ray diffraction. Solutions were deposited on an X-ray diffraction lamella and dried overnight. Powder XRD was performed using a Bruker D8 Advance X-ray diffractometer. The current and the voltage were 40 mA and 40 mV respectively, with a step size of 0.112° $s^{-1}$ in the 2θ range of 5-50°. Diffractograms were analyzed using X'pert data software. Interplanar distances were determined from powder raw pattern (20), satisfying Bragg's condition.

Fluorescence Spectroscopy. All spectra were recorded using an ultramicro 10 mm length cell and a PTI QuantaMaster spectrofluorometer. ANS and ThT were used as fluorogenic probes to follow aggregation and/or the formation of amyloid fibrils. ThT or ANS was added to the sample at a final concentration 450 and 40 μM, respectively. ThT emission was measured with excitation at 440 nm and the emission was measured between 50 and 550 nm, while ANS emission was measured between 385 and 585 nm after excitation at 370 nm. All spectra were blank-subtracted with the corresponding peptide-free solution and normalized.

Cell viability assays. For metabolic assays, J774A.1 or INS-1E cells were seeded in black-wall clear bottom 96-well plates (TC treated) at a density of 25,000 (J774A.1) or 30,000 (INS-1E) cells/well in complete Dulbecco's Modified Eagle's medium supplemented with 10% (v/v) fetal bovine serum, 100 U/mL penicillin and 100 μg/mL streptomycin (J774A.1), or RPMI-1640 (INS-1E) medium. DC2.4 or HEK-293T cells were seeded at a density of 25,000 (DC2.4) or 5,000 (HEK-293T) cells/well in RPMI-1640, supplemented with 10% FBS, 1×L-Glutamine, 1× non-essential amino acids, 1×HEPES Buffer Solution and 0.0054× β-Mercaptoethanol (DC2.4), or DMEM high glucose medium supplemented with 10% (v/v) fetal bovine serum, 100 U mL-1 penicillin and 100 μg $mL^{-1}$ streptomycin (HEK-293T). After 24 h incubation at 37° C. in 5% $CO_2$, cells were treated by the direct addition of peptide solutions diluted in order to reach a final concentration of 150 μM (in term of monomer). Cells were incubated for 24 h and cellular assays were performed. Cellular viability was measured by the resazurin reduction assay. Cell viability (in %) was calculated from the ratio of the fluorescence of the treated cells to the buffer-treated cells. Data of at least four experiments were averaged and expressed as the mean±S.D. Results were analyzed using the Student's t test. For live/dead assays, cells were seeded in 24-well plates at a density of 180,000 cells per well and 30,000 cells per well for INS-1E and HEK-293T, respectively. After 48 h incubation at 37° C. in 5% $CO_2$, cells were treated by the direct addition of peptide solutions ($50\times10^{-3}$ m Tris, pH 7.4) to reach a final concentration of $50\times10^{-6}$ m. Cells were incubated for 24 h. Viability was measured by the resazurin metabolic assay and was calculated (in %) from the ratio of the fluorescence of the treated sample to the vehicle control ($50\times10^{-3}$ m Tris, pH 7.4). Data of at least three independent experiments were averaged and expressed as the mean±standard deviation (SD). Statistical analysis was performed with Prism 6.0 software using the Student's t-test and statistical difference (between control and treated cells) was established at $P<0.01$. Live/Dead assays were performed by the addition of the reagent solution ($4\times10^{-6}$ mM ethidium homodimer-1; $2\times10^{-6}$ mM calcein-AM). After 45 min incubation, plates were imaged using a fluorescent microscope.

Kinetics of Amyloid Seeding. Peptide solutions were prepared by dissolving the lyophilized and monomeric peptides at a concentration of 50 μM in 20 mM Tris, pH 7.4 containing 40 μM thioflavin T (ThT). Assays were performed at 25° C. without stirring in sealed black-wall, clear-bottom 96-well non-binding surface plates (Corning) with a total volume of 100 μL per well. Final peptide concentrations varied between 12.5 and 25 μM, and ThT concentration was constant at 40 μM. hIAPP fibrils and NRs were sonicated for 5 minutes and added to the monomers-ThT solution. Fluorescence was measured every 10 min over the course of 20 h, using an Infinite M1000pro fluorescence plate reader (TECAN). The fluorescence, with excitation at 440 nm and emission at 485 nm, was measured from the bottom of the well. For each experiment, control reactions (without IAPP) were carried. Data was corrected by subtracting the corresponding control reaction and plotted as fluorescence vs. time.

Confocal microscopy and flow cytometry. J774A.1 and DC2.4 were cultured on coverslips for 48 h, as described above, at a density of 15,000 cells/well. Cells were treated by the direct addition of fluorescent labeled peptides and nanorods (50 μM in terms of monomers) for 30 min, 1 h and 3 h. Cells were then washed three times with PBS, fixed with 4% paraformaldehyde (Santa Cruz) and stained with 1 μg/mL DAPI (4',6-Diamidino-2-phenylindole dihydrochloride) and 1 units/mL Texas Red-X Phalloidin. Cover glass were mounted, and fluorescence was analyzed using a Ti inverted microscope with a Nikon A1R confocal using a 60× oil immersion lens. All images were analyzed using Fiji Image J software. For flow cytometry analysis, cells were seeded in 6-well plates at a density of 250,000 cells/well overnight. After removing the media, cells were treated with fluorescent labeled NRs (150, 100 and 50 μM in terms of monomers) at 37° C. for 30 min, 1 h and 3 h. in complete culture media. After incubation, cells were washed 3 times with cooled PBS buffer and harvested. Cells were suspended in cooled PBS buffer prior to flow cytometry analysis. To confirm that the measured fluorescence was not associated to adsorption at the cell surface, trypan blue was used to quench the extracellular fluorescence of life cells. Cells were treated with 1 mg/mL trypan blue for 1 min immediately before flow cytometry analysis. Flow cytometry analyses were performed on 10,000 gated cells/sample with excitation at 488 nm and emission at 530 nm with a BD FACSCalibur flow cytometer. Data were analyzed using FlowJo software package.

TLR-2 stimulation. HEK293 cells stably co-transfected with mTLR2 and SEAP (HEK-Blue mTLR2 cells, InvivoGen) were cultivated in Dulbecco's Modified Eagle's Medium supplemented with 4.5 g/l glucose, 10% (v/v) fetal bovine serum, 100 U/ml penicillin, 100 mg/ml streptomycin, 100 mg/ml Normocin™, 2 mM L-glutamine. At 50-80% confluency, cells were seeded in Hek-Blue detection medium (InvivoGen) at a density of 50,000 cells/well in a 96-well plate containing NRs and controls. After 16 h incubation at 37° C. in 5% $CO_2$, absorbance was monitored at 630 nm.

Mice Immunizations. Animal protocols were approved by the institutional committee (CIPA: Institutional Animal Care and Use Committee of Université du Quebec a Montreal) according to the regulation of the Canadian Council for Animal Care and carried as previously described.[11] Before immunizations, M2e-NRs stock solutions were diluted at the final concentration (100, 50, 10 mmol/mice) in endotoxin-free sterile PBS. Six-week-old female BALB/c mice (n=8 and 4 (PBS challenge) mice/group) were immunized subcutaneously with 100 μL and nasally with 50 μL of synthetic peptide (M2e), fibrils (M2e-NFs and M2e-NRs). Aluminium hydroxide gel (Alhydrogel adjuvant; Alum) (InvivoGen) was used as adjuvant for subcutaneous immunization and Montanide-Gel (MG) (SEPPIC) was used for nasal immunizations. Alum and MG adjuvanted groups received the same volume and peptide dose, prepared by diluting the peptide solution in Alum at a 1:1 volume ratio or MG at 5% (v/v) final concentration. Mice were anesthetized by isoflurane inhalation before each nasal immunization. Mice received two boosts at days 14 and 28 post-primary immunization with 100 μL, each containing 100, 50 or 10 mmol of peptide or fibrils. Control mice were immunized using the same volume of PBS. Blood samples were collected from the saphenous vein at days 0, 14 and 28-post primary-immunization. Mice were sacrificed two weeks after the final boost (day 42) and sera were harvested from cardiac puncture.

Experimental infection. Two weeks after the last boost, mice were moved to biosafety level 2, anesthetized by isoflurane inhalation and infected with $5\times LD_{50}$ of influenza virus A/PuertoRico/8/34 by intra-nasal instillation in endotoxin-free PBS. Clinical signs and body weight were monitored twice daily. The clinical score scale previously described was implemented (0, normal state, no symptoms; 1, slightly ruffled fur; 2, ruffled fur but active mouse; 3, ruffled fur and inactive mouse).[47] Mice that had lost 20% or more of their initial weight and/or had a clinical score of 3 were euthanized humanely. Bronchoalveolar lavage (BAL) were performed by flushing the lungs via tracheal puncture with 1 ml of $Ca^{2+}$- and $Mg^{2+}$-free PBS supplemented with 1 mM EDTA. BAL fluids (BALD were centrifuged, and supernatants were stored frozen at −80° C.

Antibody titers measurements by indirect ELISA. Plates were coated overnight at 4° C. with 2 μg/mL of M2e peptide diluted in sodium carbonate 0.05 M (pH 9.6). After washing with PBS-T, plates were blocked with 1% (w/v) Bovine serum albumin (BSA) solution for 1 h. Determination of whole IgG titers was performed using serial dilutions (1/2) of mouse sera (starting point 1:$10^2$) in PBS-T (1% BSA) while isotype IgG determination were obtained by a dilution of 1:1600 of antisera (IgG2a, IgG2b, IgG3) (Abcam) or 1:12800 (IgG1) for subcutaneous immunization. For nasal immunization, the dilutions were 1:512 of antisera (IgG2a, IgG2b, IgG3) (Abcam), 1:8192 (IgG1) (Abcam), 1:128 (IgG, BAL) and 1:256 (IgA, BAL). After 3 h incubation and 3 washes, HRP-conjugated goat anti-mouse whole IgG (1:5000), IgG1 (1:10000), IgG2a (1:5000), IgG2b (1:5000), IgG3 (1:5000) and IgA (1:10000) (Invitrogen) were added for 1 h. Plates were washed and HRP signal was detected using TMB substrate (Sigma-Aldrich) by optical density (450 nm) measurements using an Infinite M1000pro fluorescence plate reader (TECAN). The endpoint antibody titers were calculated by regression analysis, plotting serum dilution versus the absorbance with the following regression curve equation: y=(b+cx)/(1+ax). Endpoint titers were defined as the highest dilution resulting in an absorbance value twice that of blank points (points without immune serum).[47]

Statistical Data Analysis. Data were expressed as arithmetic means±standard errors of the means (SEM). The nonparametric Mann-Whitney or unpaired t test (two groups), one-way analysis of variance (ANOVA), Tukey's multiple-comparison test, or log rank Mantel-Cox test (>2 groups) was used to compare unpaired values (GraphPad software, San Diego, CA). P values of <0.05 were considered significant; levels of significance are indicated on the graphs by asterisks: *, P=0.01; , P=0.001; *, P=0.0001; and ****, P<0.0001.

Example 2: Effect of Electrostatic N-Terminal Capping of the 20-29 Fragment (SNNFGAILSS, SEQ ID NO:1) of the Islet Amyloid Polypeptide (IAPP)

The amyloid core used in this study consists of the 20-29 fragment (SNNFGAILSS, SEQ ID NO:1) of the islet amyloid polypeptide (IAPP), which includes the aggregation-prone sequence FGAIL (SEQ ID NO:7, FIG. 1). This 10-mer peptide sequence ($I_{10}$) has a high propensity to self-assemble into polymorphic twisted fibrils characterized by a cross-β-sheet quaternary structure[29A]. Charged residues were used as capping units owing to their ability of restricting amyloid nucleation, protofilament packing and/or elongation upon incorporation in the vicinity of an amyloidogenic stretch.[7A,30A] Electrostatic strength was tuned by introducing multiple amino acids and/or by acetylating the N-terminal amine. As positive and negative charges are not equally permitted within an amyloidogenic sequence,[31A] the capping unit was linked to the amyloid core via a flexible tetrapeptide spacer (GSGS, SEQ ID NO:4). A small library of C-terminally amidated I10 derivatives ($KKI_{10}$, $KI_{10}$, Ac-$KI_{10}$, $I_{10}$, $EI_{10}$, $EEI_{10}$, and Ac-$EEI_{10}$) was prepared by solid phase peptide synthesis based on Fmoc chemistry. Self-assembly was initiated by the direct dispersion of the monomerized peptides in hexafluoroisopropanol (HFIP) and subsequent dilution in Tris buffer ($50\times10^{-3}$ M pH 7.4; 1% HFIP final concentration). HFIP was used to facilitate the solubilization of $I_{10}$, Ac-$KI_{10}$, and $EI_{10}$, which could not be directly solubilized in aqueous buffer. No significant effect of 1% HFIP on the final morphology of the assemblies was observed for the peptides $KI_{10}$, $KKI_{10}$, $EEI_{10}$, and full-length IAPP. Excepting for $KKI_{10}$ ($500\times10^{-6}$M), self-assembly occurred at $150\times10^{-6}$ M (otherwise stated) under continuous rotary agitation (40 rpm) at room temperature. $KKI_{10}$ was used at a higher concentration to facilitate self-assembly since no assemblies were detected at $150\times10^{-6}$ M.

Figures 2A, 2B, 2C, 2D:
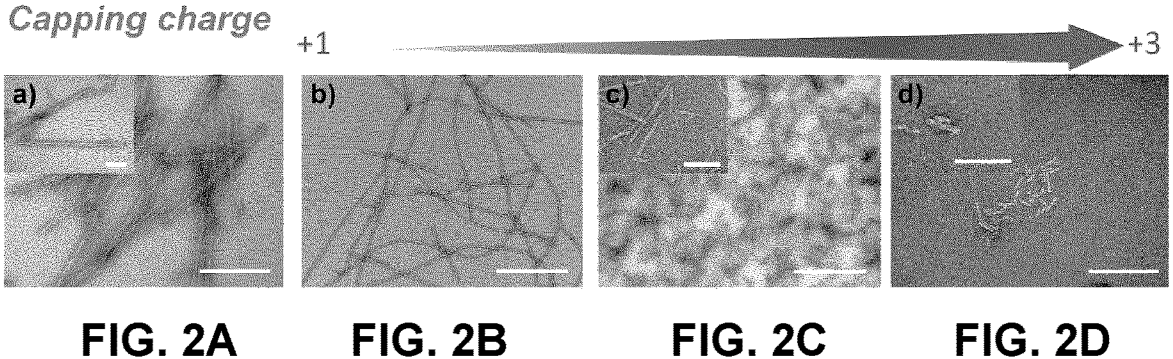

Negative-stain transmission electron microscopy (TEM) revealed that the capping unit drastically affects the supramolecular morphology (FIGS. 2A-H). At the mesoscopic scale, the resulting assemblies showed various shape, including nanorods ($KKI_{10}$, $KI_{10}$), rope-like fibrils (Ac-$KI_{10}$, $EI_{10}$), belt-like filaments ($EEI_{10}$), amorphous aggregates (Ac-$EEI_{10}$), and polymorphic twisted ribbons and fibrils ($I_{10}$, full-length IAPP). As previously reported for the 20-29 segment of IAPP, $I_{10}$ assembled into polymorphic fibrils with a coexistence of twisted and helical ribbon morphology with length from 200 nm up to 3.6 μm (FIG. 3A and Table 1).[29A,32A]. The morphology obtained for $I_{10}$, which contains the GSGS linker, is nearly identical to the morphology previously revealed for the C-terminally amidated decapeptide IAPP(20-29) under similar conditions, [33A] suggesting that the addition of a flexible tetrapeptide spacer at the N-terminus has a minimal effect on the fibril organization. In presence of a +1 capping unit, i.e., Ac-$KI_{10}$, unbranched and long rope-like fibrils with length in the order of ≈1 μm were obtained (FIG. 2B). With a capping unit charge of +2 ($KI_{10}$), the peptide self-assembled into short rod-like structures (=150 nm) (FIG. 2C, Table 1). These nanorods (NRs) were uniform, as indicated by the low polydispersity index of 0.40 obtained by dynamic light scattering (DLS). This monodispersity is unusual for amyloid-based assemblies, as amyloid fibrils are recognized for their (supra)molecular heterogeneity, exhibiting multiple distinct morphologies and a wide variety of length from a single preparation.[34A] When two Lys residues were introduced at the N-terminus ($KKI_{10}$), very short and uniform rod-like assemblies (≈50-100 nm) were obtained (FIG. 2D). This data reveals that the morphology and polymorphism can be modulated by tuning the intermolecular electrostatic repulsive forces between the positive charges at the N-terminus of a complex and highly amyloidogenic sequence.

Figures 2E, 2F, 2G, 2H:
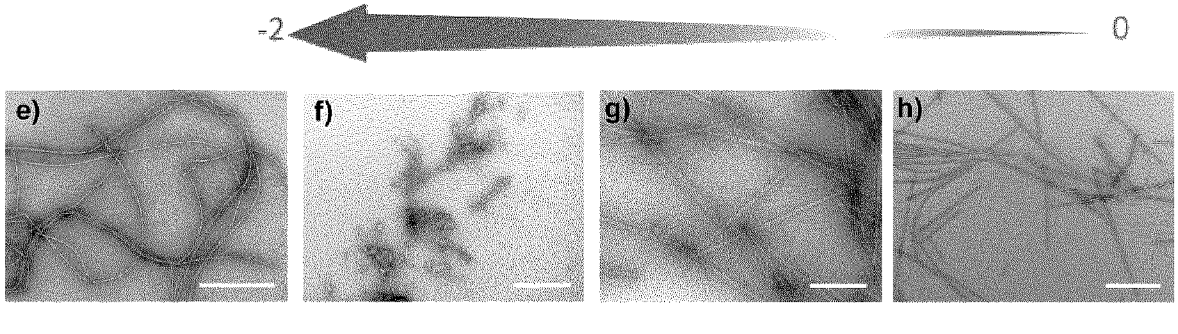
FIG. 2E: IAPP.
FIG. 2F: Ac-$EEI_{10}$.
FIG. 2G: $EEI_{10}$.
FIG. 2H: $EI_{10}$.
Figure 3A:
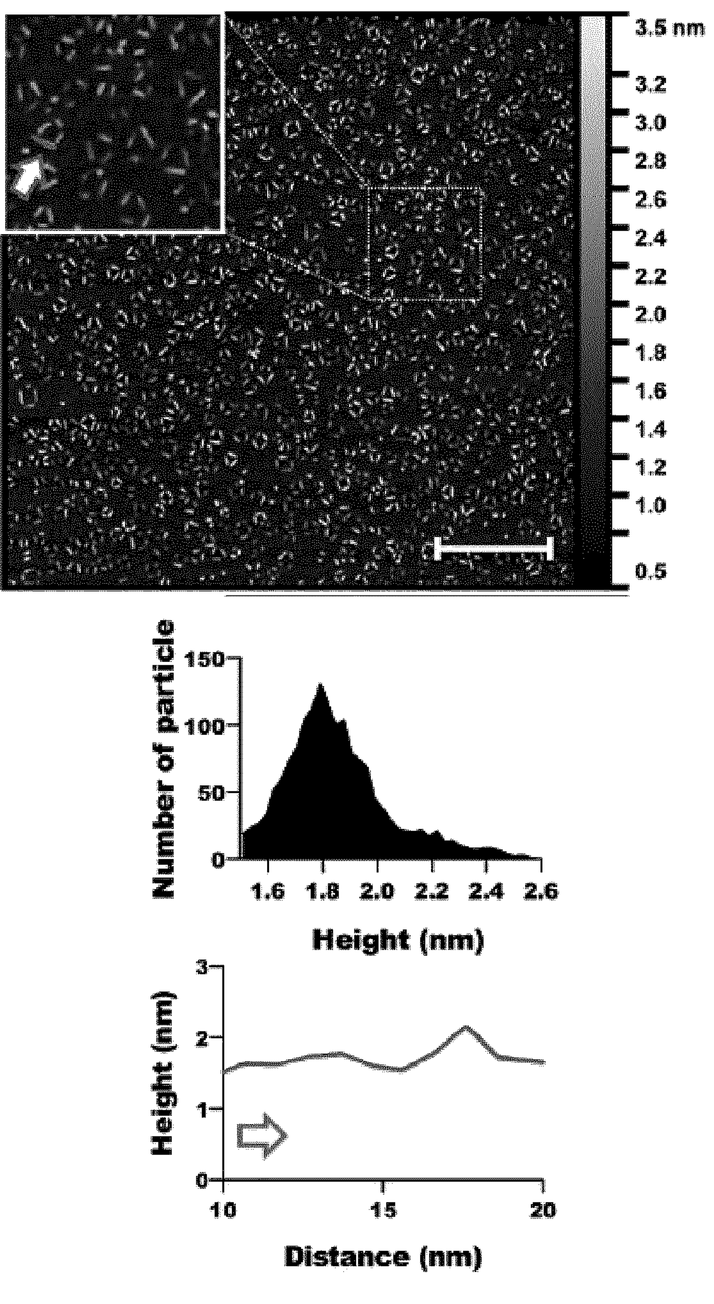

While the variations in length and morphology of the assemblies correlated with the electrostatic strength of the positive capping units, this correlation was not observed for the negatively capped peptides. Assemblies obtained after 48 h aging of $EI_{10}$ and $EEI_{10}$ were long (>1 μm) and somewhat polymorphous (FIG. 1). $EI_{10}$ assembled into rope-like fibrils whereas the EE-capped peptide formed flat belts. Addition of an acetyl group to $EEI_{10}$ (Ac-$EEI_{10}$), led to amorphous aggregation (FIG. 2F). Thus, not only the strength of the electrostatic capping unit, but also the type of charge, modulates the final supramolecular morphology. The surfaces of the amyloid-based assemblies were charged, with range between +47 and −44 mV (Table 1). Surface charge constitutes a key feature for biomedical applications, since interactions with biological membranes are known to be strongly affected by electrostatic interactions, ultimately influencing both the immunogenicity and biological fate of peptide-based nanomaterials

TABLE 1

Characterization of $I_{10}$ amyloid-like assemblies.

| Peptide | Morphology | Length[a) [nm] | Heigth[b) [nm] | Z-average[c) [nm] | Polydispersity index[d) | Surface charge[e) [mV] |
|---|---|---|---|---|---|---|
| $KKI_{10}$ | short rod-like | 66.4 ± 21.3 | 1.8 ± 0.8 | 99.8 ± 1 | 0.34 ± 0.01 | 47 ± 5 |
| $KI_{10}$ | rod-like | 149 ± 75 | 3.7 ± 0.8 | 144.5 ± 4.4 | 0.40 ± 0.01 | 45 ± 2 |
| Ac-$KI_{10}$ | thick rope-like | 1199 ± 765 | 7.0 ± 0.7 | 750.4 ± 59.3[d) | 0.99 ± 0.01 | 49 ± 5 |
| $I_{10}$ | twisted ribbon | 233-3627 | 6.3 ± 0.8 | 4027.3 ± 522.0[d) | — | 15 ± 2 |
| $EI_{10}$ | rope-like | 378-2069 | 7.9 ± 0.3 | 6290.6 ± 1434.5[d) | — | −4 ± 2 |
| $EEI_{10}$ | belt-like | 2241 ± 765 | 6.2 ± 1.0 | — | — | −44 ± 6 |
| Ac-$EEI_{10}$ | amorphous | — | — | — | — | — |

[a)]Negative stain TEM;
[b)]AFM;
[c)]DLS;
[d)]Data should be taken with precaution, as the hydrodynamic radius is less accurate when the shape of the particles diverges significantly from the spherical approximation, as for long fibrils;
[e)]Zeta potential.

Figure 2I:
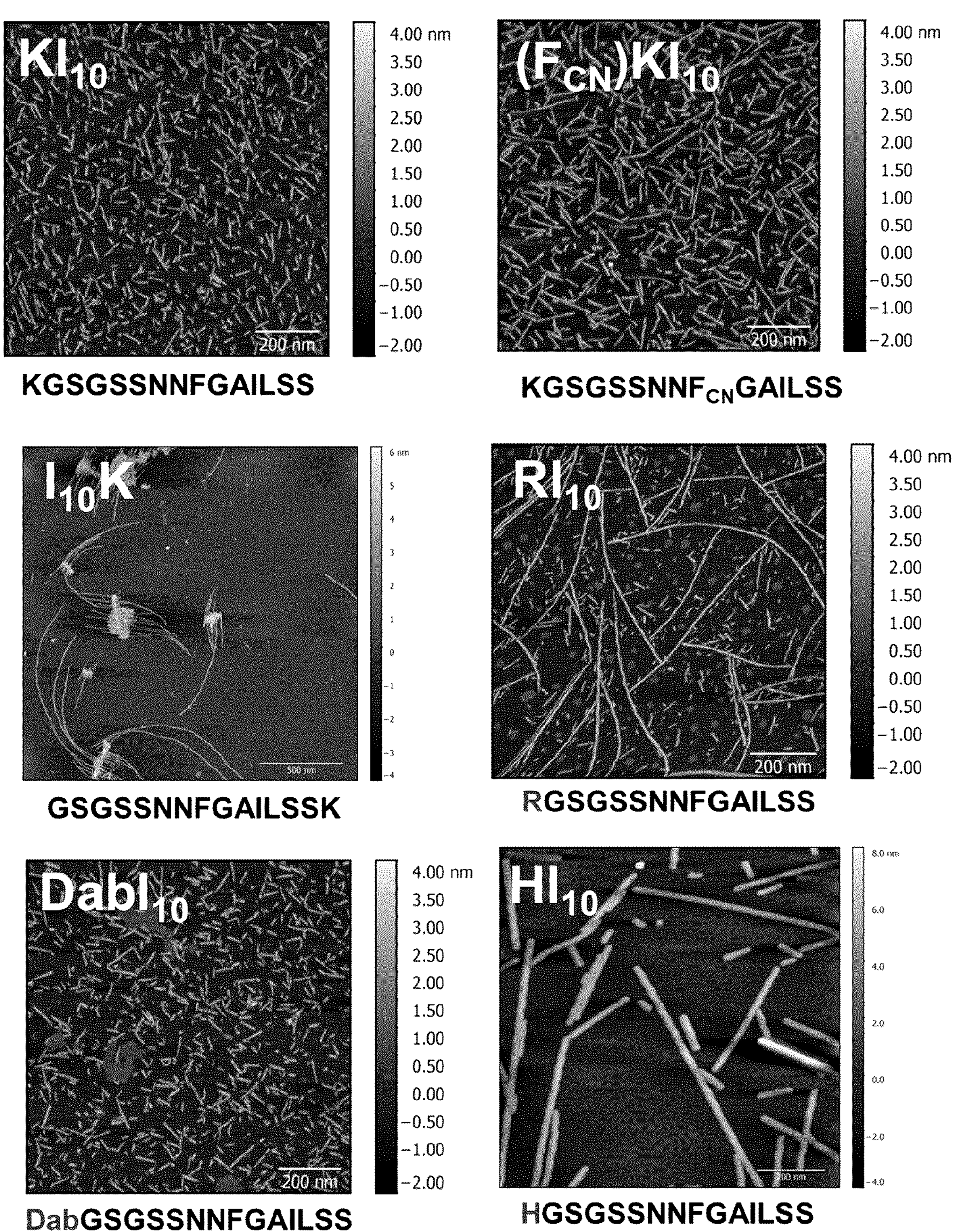
FIG. 2I: AFM images of variants of the $KI_{10}$ sequence. KGSGSSNNFGAILSS (SEQ ID NO:13), KGSGSSNNF$_{CN}$-GAILSS (SEQ ID NO:8), GSGSSNNFGAILSK (SEQ ID NO:14), RGSGSSNNFGAILSS (SEQ ID NO:9), DabGSGSSNNFGAILSS (SEQ ID NO:11), and HGSGSSNNFGAILSS (SEQ ID NO:10). Peptides were assembled in Tris buffer ($50\times10^{-3}$ m, pH 7.4) under continuous rotary agitation for 48 h at a concentration of $150\times10^{-6}$ m (FIGS. 2A-C and F-H), d) $500\times10^{-6}$ m (FIG. 2D), or $50\times10^{-6}$ m (FIG. 2E). Scale bar: 200 nm.

The results presented in FIG. 2I show that:

substituting the phenylalanine residue by a cyano-phenylalanine residue (KGSGSSNNF$_{CN}$GAILSS, (F$_{CN}$)$KI_{10}$, SEQ ID NO:8);

the presence of a primary amine ($NH_2$) in the side chain of the residue(s) forming the N-terminal capping unit is important for the morphology of the assembled nanorods, as $KI_{10}$ analogs comprising the other positively-charged amino acid arginine (RGSGSSNNFGAILSS, $RI_{10}$, SEQ ID NO:9) or histidine (HGSGSSNNFGAILSS, $HI_{10}$), which contain a secondary amine, NH) do not adopt a short-like rod confirmation like the $KI_{10}$, in contrast to a peptide capped with the lysine analog diaminobutyric acid (DabGSGSSNNFGAILSS, SEQ ID NO: 11, $DabI_{10}$) that contain a primary amine;

incorporating the positively-charged capping unit at the C-terminal end instead of the N-terminal end (I10K) does not result in assemblies with a short rod-like structure.

Example 3: Further Characterization of the Positively Capped Assemblies

Figure 3B:
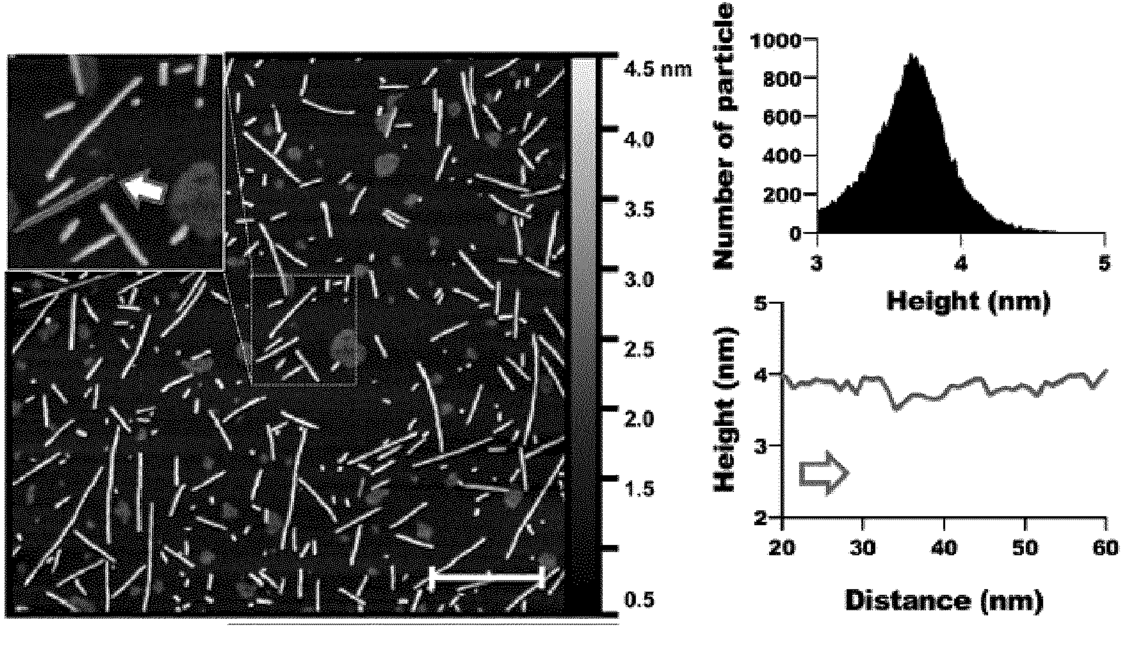
Figure 3C:
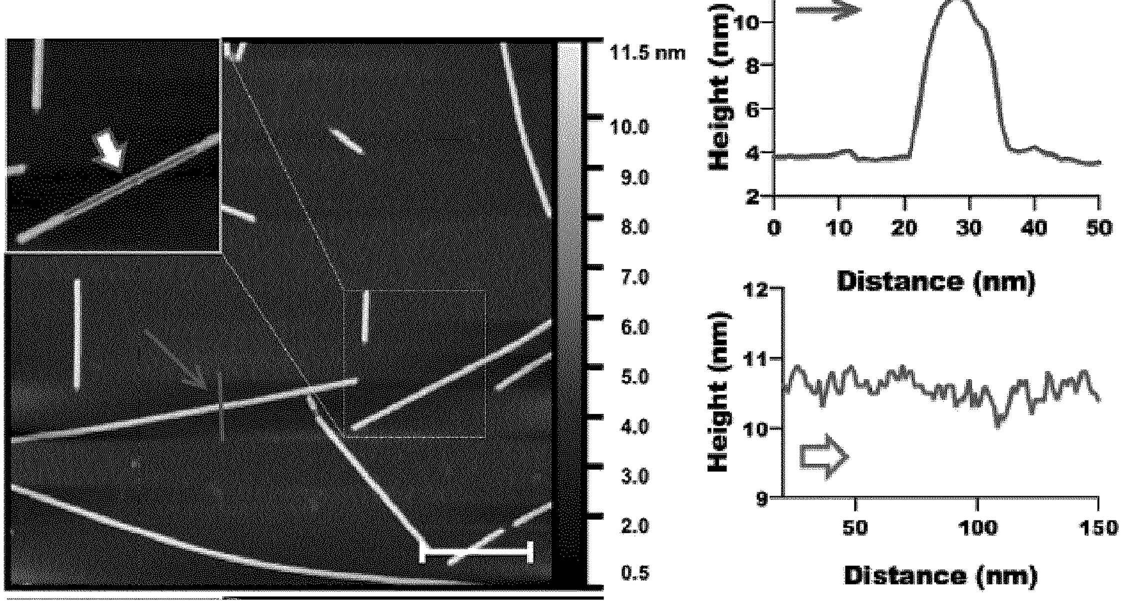

Considering the unusual morphology and exceptional uniformity for amyloid-based fibrils, the (supra)molecular characteristics of positively capped assemblies were further investigated to gain insights into their unique characteristics. Atomic force microscopy (AFM) validated the mesoscopic architecture observed by TEM, including the differences between positive and negative capping units. For positively capped assemblies, the height was also controlled by the electrostatic strength, with height ranging from 7.0 nm for Ac-$KI_{10}$ to 1.8 nm for $KKI_{10}$ (FIG. 3 and Table 1). $KI_{10}$ assemblies showed an AFM average height of 3.7±0.8 nm. Interestingly, it was observed by AFM and TEM imaging that positively capped-I10 assemblies are non-twisted and planar, while fibrils obtained from uncapped I10 are twisted with a periodical spacing (pitch) of 74 nm (FIG. 3). It has been reported using the FFFF self-assembling core that electrostatic repulsions between terminal charges reduce the twisting pitch of β-sheet tapes and guide to highly twisted fibrils.[7A] In the present study, the opposite effect is observed, most likely because the $I_{10}$ amyloid sequence is more complex, leading to a diversity of intermolecular interactions. $KI_{10}$ rod-like assemblies display an infinite number of units per turn and a very small helical rotation. Nonetheless, electrostatic interactions strongly modulate the twisting pitch of both $Phe_4$ and $I_{10}$ based-assemblies, although the amyloid core ultimately governs the final effect, i.e., increase or decrease of twisting. This observation further demonstrates the complexity of the mechanisms of amyloid formation. Interestingly, $KI_{10}$ nanorods are very rigid for biopolymer, which typically tend to be flexible. Although the conformation having the minimum energy is normally a straight rod, accumulation of thermal fluctuations leads to polymer bending.[37A] Regarding amyloids, twisting of β-sheet is associated with small rotations of the subunits along the fibril axis, which increase the length of hydrogen bonds and promote flexibility and disorder of the fibril. Electrostatic repulsions between the monomers are likely at the origin of the observed rigidity by impeding filament twisting. Accordingly, this rigidity frustrates amyloid growth, ultimately leading to a unique control over the length of the $KKI_{10}$ and $KI_{10}$ nanorods.

Fourier transform infrared spectroscopy (FTIR) spectroscopy was used to probe the secondary structure within the assemblies by recording the amide I region of the spectrum (1700-1600 $cm^{-1}$). Attenuated total reflectance (ATR) allowed us to characterize the amyloids at low concentration, i.e., at the self-assembly concentration. Spectra obtained for $KKI_{10}$, $KI_{10}$, Ac-$I_{10}$, and $I_{10}$ assemblies were characterized by two amide I'peaks at 1622 and 1658 $cm^{-1}$ (FIG. 4A). The first peak was indicative of protein aggregates rich in β-sheets and contains a shoulder at 1634 $cm^{-1}$, which could be assigned to an aperiodic structure. Interestingly, the signal at 1622 $cm^{-1}$ was more intense for $KI_{10}$ and $KKI_{10}$ relative to Ac-$KI_{10}$ and $I_{10}$. This sharp increase of absorbance is indicative of the linear geometry of $KI_{10}$ and $KKI_{10}$ assemblies, as their rigidity is associated with an absence of helical rotation. In fact, the length of intermolecular backbone hydrogen bonds in twisted β-sheets extends with the helical rotation, which leads to a decrease of intensity of the carbonyl vibration band at 1622 $cm^{-1}$,[10A] as observed for the uncapped assemblies. The peak at 1658 $cm^{-1}$ suggested a parallel β-sheet secondary structure. Second derivative and spectral deconvolution revealed a peak at 1616 $cm^{-1}$, representing two different types of β-sheet structures (staggered β-sheet). It was reported that $IAPP_{20-29}$ contains both parallel and antiparallel β-strands and this could be at the origin of the observed macroscopic polymorphism.[29A] In the present study, no band characteristic of an antiparallel β-sheet was detected for all assemblies. This parallel orientation is somewhat surprising considering the energy penalty associated with electrostatic repulsions between N-terminal charges under this configuration and this could explain the strong impact of electrostatics on the final architecture.

Powder X-ray diffraction (XRD) of $I_{10}$ assemblies and its three positively capped counterparts revealed a diffraction pattern characterized with two sharp peaks. Bragg reflections corresponding to 4.7 and 8.7 Å periodic spacing were measured (FIG. 4B).[38A] The 4.7 Å meridional reflection, a typical signature of the cross-β-sheet quaternary structure, arises from the spacing between hydrogen-bonded β-strands, while the 8.7 Å spacing corresponds to intersheet distances. This intersheet distance is somewhat short for amyloids, which is typically between 10 and 12 Å. Nonetheless, the distances between sheets in amyloids are known to be less defined.[39A] Moreover, intersheet distances may be shorter in dry interface,[40A] as for the present study. XRD diffraction patterns indicate that the charged capping unit does not modify the molecular packing at atomistic level within the $I_{10}$ assemblies. The amyloid cross-β-sheet conformation was also evaluated by measuring thioflavin T (ThT) fluorescence. ThT is a small dye whose fluorescence emission increases sharply upon its binding to cross-β-sheet quaternary structure.[41A] Surprisingly, an increase of ThT fluorescence was only observed for uncapped I10, whereas the N-capped assemblies were ThT-negative (FIG. 4C). Owing to the surface charge of the positively capped assemblies (Table 1), this negative ThT signal could be associated with the inhibition of ThT binding through electrostatic repulsion, as this probe carries a positive charge on the thiazole ring. Accordingly, it was evaluated if by screening the surface charges with salt, a ThT-positive signal for capped assemblies could be monitored. In fact, ThT fluorescence emission increased proportionally with increasing NaCl concentrations, albeit ThT signal remained very low compared to the uncapped $I_{10}$ assemblies. This observation, along with the XRD and FTIR analyses, is suggestive of a prototypical amyloid-like cross-β-sheet quaternary organization for Ac-$KI_{10}$, $KI_{10}$, and $KKI_{10}$ assemblies.

The assemblies were further characterized by far-UV circular dichroism (CD) spectroscopy. Immediately after their solubilization, the peptides $I_{10}$, Ac-$KI_{10}$, and $KI_{10}$ showed a CD spectrum characterized with a single minimum at 200 nm, representative of a random coil secondary structure (FIG. 4D). $KKI_{10}$ displayed a CD spectrum with two minima at 205 and 225 nm, indicative of an ordered secondary structure. Deconvolution of $KKI_{10}$ CD spectrum using the K2D3 method[42] revealed a high content of α-helix, showing that the incorporation of two Lys residues at the N-terminus of $I_{10}$ alters the secondary conformation in the preassembly state. Upon 48 h incubation, uncapped $I_{10}$ gave rise to a single minimum at around 225 nm, characteristic of prototypical β-sheet-rich amyloid (FIG. 4E). CD spectra of $KI_{10}$ and Ac-$KI_{10}$ assemblies were clearly distinct from $I_{10}$, with a broad and intense peak at 205 nm and a slight shoulder around 222 nm. This minimum at 205 nm could be attributed to π-π stacking of the Phe within the assemblies and/or to the distortion of supramolecular packing.[43A] For $KKI_{10}$, a drastic transition occurred during self-assembly and a weak single minimum at 210 nm was observed after 48 h incubation, suggesting of some differences between the structural organization of $KKI_{10}$ and $KI_{10}$. However, these CD spectra may not represent a specific secondary structure, but could instead be considered of an indicator of self-assembly.[44A] Irrespective of the interpretation of spectra, CD analysis revealed that electrostatic repulsions between capped monomers results in an atypical secondary structure signal. Nonetheless, ATR-FTIR indicated the presence of parallel β-sheets, XRD exposed the typical amyloid 4.7 Å distance and ThT binding revealed a cross-β-sheet organization.

Figure 5B:
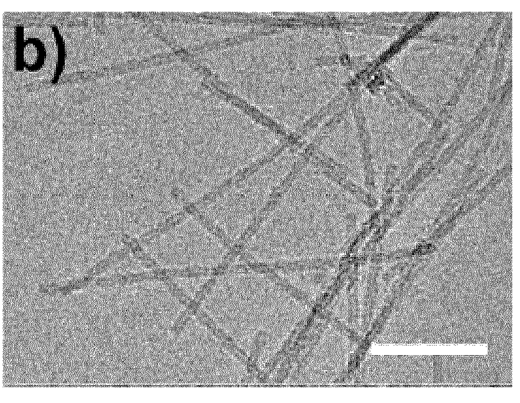
Figure 5C:
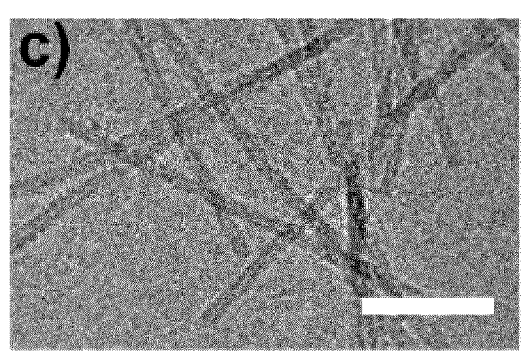
Figure 5D:
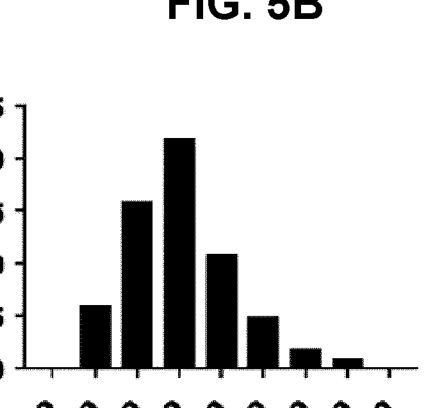
Figure 5D:
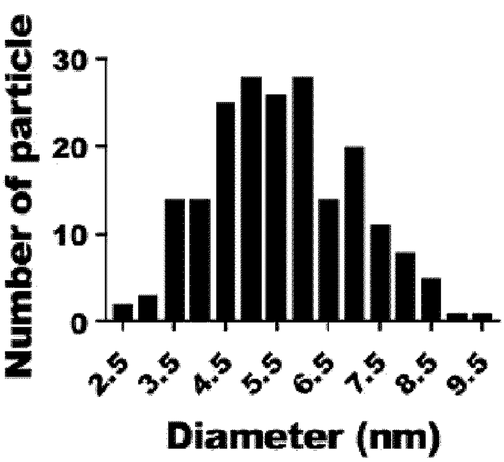
Figure 5E:
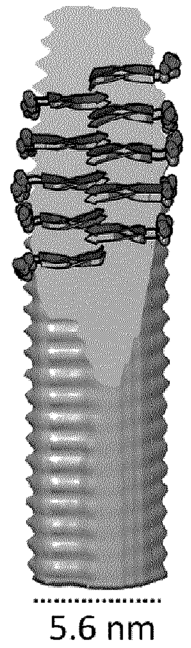
Figure 5F:
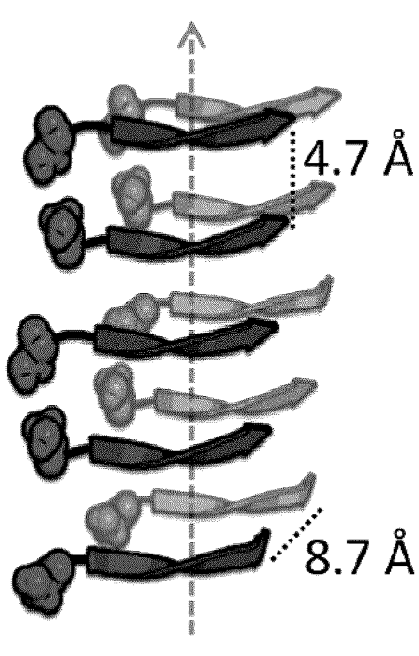

$KI_{10}$ nanorods were analyzed by cryo-TEM to obtain details about their molecular architecture and to validate "in solution" their unique morphology and low polydispersity. It was observed an identical morphology as "dried samples," although the freeze nanorods were slightly longer (≈200 nm) (FIG. 5). This increase in length likely reflects the higher concentration of monomers used to prepare cryo-TEM samples ($400\times10^{-6}$ m). Nonetheless, the untwisted and rigid rod-like morphology was conserved and an average diameter of 5.6 nm was measured. Considering that $KI_{10}$ assemblies are straight rods, it was challenging to assign a helical screw and point group symmetry.[45A] Thus, running iterative helical real space reconstruction was problematic and $KI_{10}$ nanorods structural organization could not be determined unambiguously by cryo-TEM. Nonetheless, keeping in mind all biophysical data, i.e., XRD, Zeta potential, and ATR-FTIR, a structural model of $KI_{10}$ nanorods supported by the theoretical backbone length and the distances obtained by cryo-TEM was constructed. Accordingly, it is proposed that individual filaments are composed of parallel β-sheets and that the inner hydrophobic surfaces are tightly packed against each other whereas the charged capping units are facing outward (FIGS. 5E and 6F). This model of $KI_{10}$ nanorods depicts two staggered protofilaments, consistent with ATR-FTIR.

Figures 6A, 6B, 6C, 6D:
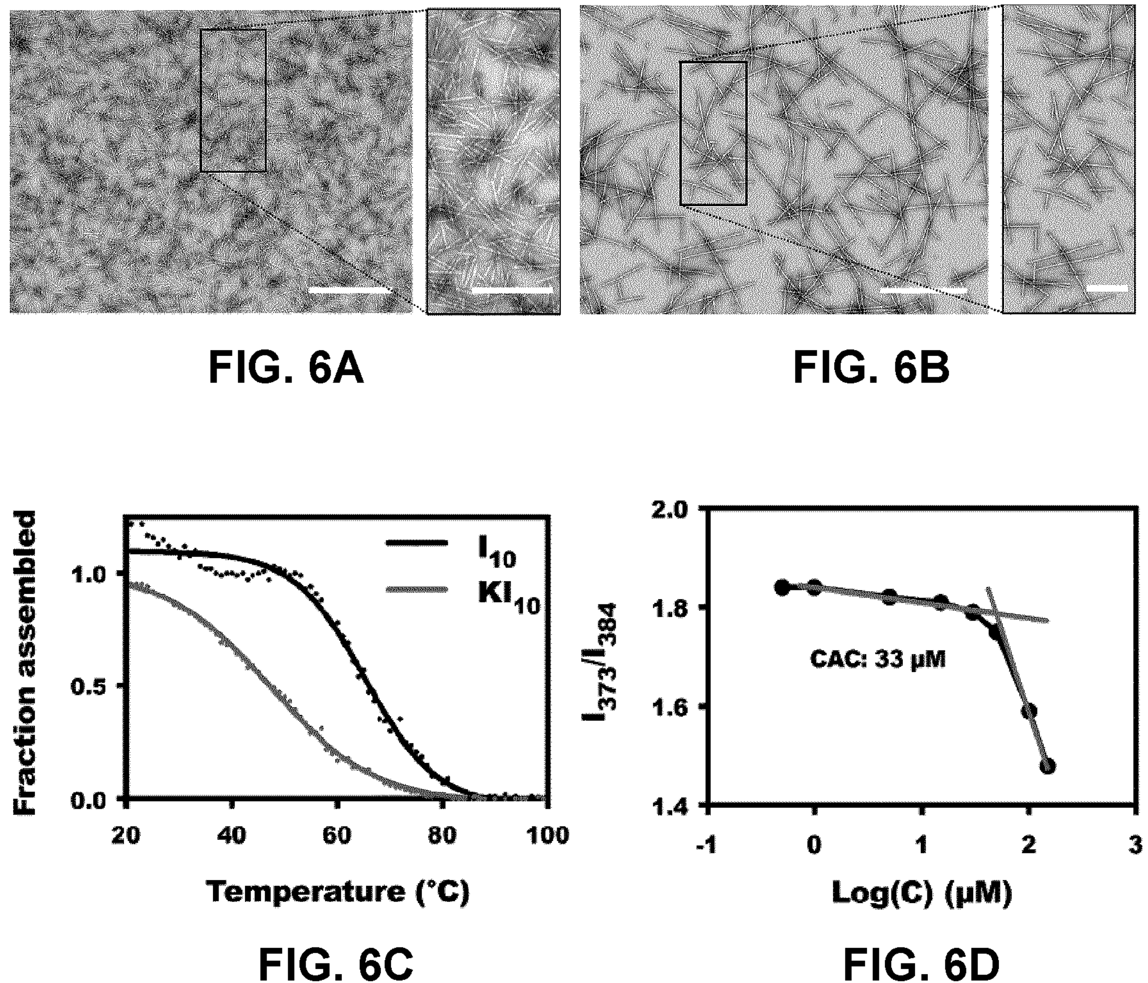
FIGS. 6A-D show the stability and critical aggregation concentration of $KI_{10}$ nanorods.

Structural transitions and modulation of morphology under kinetics control have been described for amphiphilic[46A] and β-sheet[23A,47A] self-assembling peptides. Accordingly, the uniformity of $KI_{10}$ nanorods could be the result of a kinetically trapped constrained conformation. These assemblies could ultimately evolve into typical long and polydisperse amyloid fibrils, as those observed for uncapped $I_{10}$. Accordingly, the macroscopic stability of $KI_{10}$ nanorods was evaluated by incubating the peptide under continuous circular agitation for up to 10 days. Strikingly, TEM analysis revealed no significant growth and macroscopic rearrangement over time (FIG. 6A). After 10 days, KI10 nanorods were almost identical to the assemblies obtained after 48 h, with an average length of 142.5±29.2 nm and diameter of 6.2±2.0. These assemblies also remained ThT-negative. Next, it was tested whether the morphological uniformity of $KI_{10}$ assemblies could be concentration dependent, i.e., that a mesoscopic transition from a rod-like morphology into polymorphic fibrils could be triggered at high concentrations. $KI_{10}$ was incubated at $1.5\times10^{-3}$ m and the morphology of the assemblies was analyzed by TEM. Uniform, untwisted, and straight nanorods were obtained, albeit these assemblies were significantly longer, with an average length of 209.6±153.1 nm (FIG. 6B). $KI_{10}$ assemblies also tend to clump together and align themselves over time at this high concentration. Overall, these observations suggest that $KI_{10}$ nanorods represent an actual free energy minimum. In particular, the macroscopic stability over time is interesting for amyloid-based assemblies and constitutes an important feature for future applications in nanomedicine.

Figures 7A, 7B:
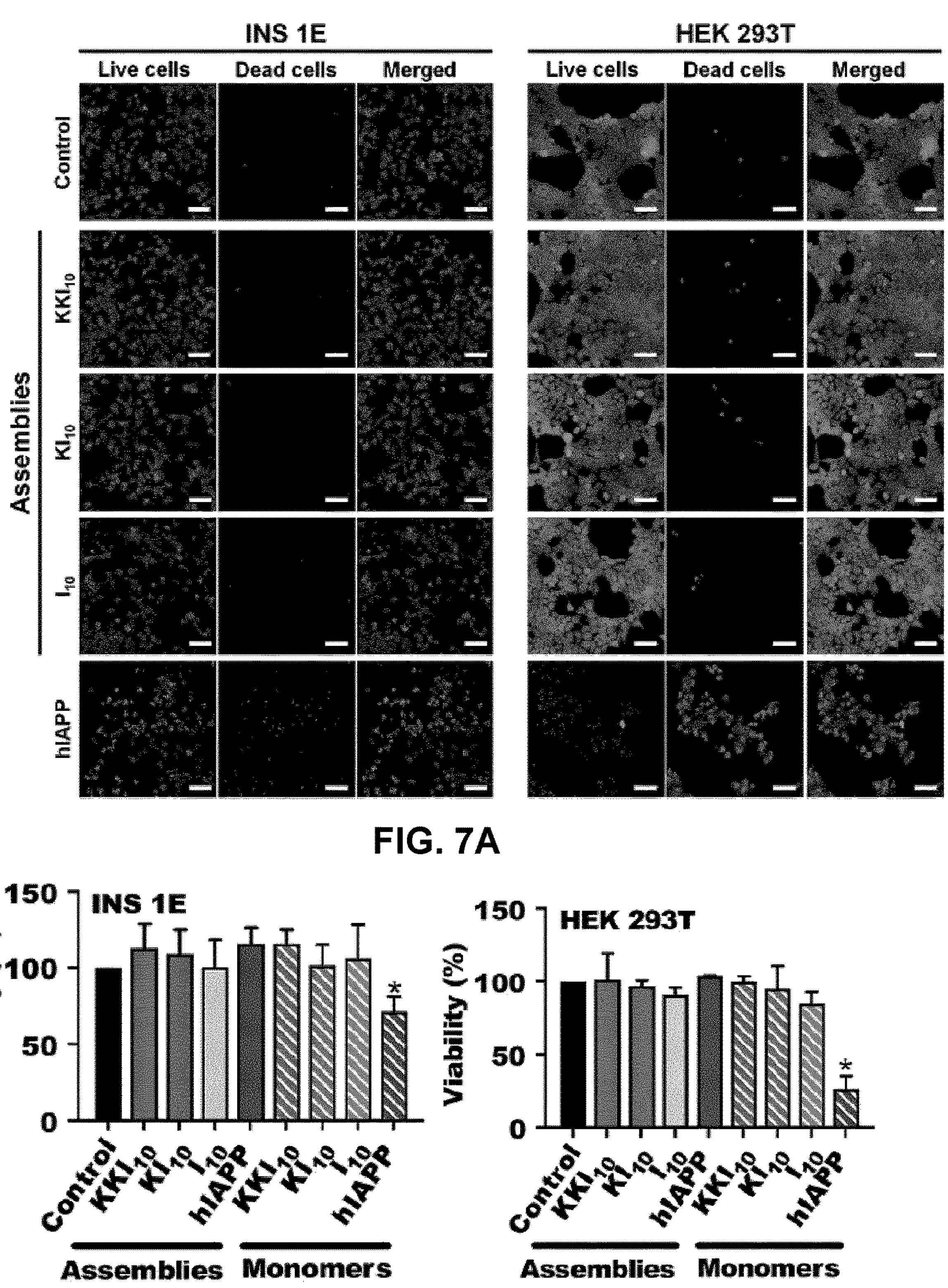
FIGS. 7A-B show the cytocompatibility of positively capped amyloid assemblies.

Prototypical amyloid fibrils are known to be thermodynamically stable, maintaining their secondary structure and quaternary organization under harsh denaturing conditions. The stability of $KI_{10}$ nanorods was investigated by thermal denaturation to gain additional information on the amyloid-like properties. Thermal denaturation was evaluated by measuring conformational changes with CD spectroscopy at three different wavelengths (222, 212, and 205 nm). Typical amyloid fibrils assembled from full-length IAPP were very stable with no melt observed, even in presence of 2.5 m urea. Uncapped $I_{10}$ amyloid assemblies exhibited a thermal unfolding midpoint (Tm) of 62° C. at 205 nm (FIG. 6C). The addition of a Lys capping unit led to a decrease in thermodynamic stability, with a Tm of 42.6° C. for $KI_{10}$ nanorods (0205 nm). This result indicates that the neighboring sequence of an amyloid-core affects the thermodynamic stability of the resulting assemblies. The critical aggregation concentration (CAC) of $KI_{10}$ was also evaluated using pyrene, a probe that is sensitive to the polarity of the local environment.[49A] A sharp transition from monomers to assemblies was observed when the concentration exceeded $33\times10^{-6}$ m (FIG. 6D). The fact that $KI_{10}$ self-assembly followed a classical model of surfactant association is suggestive of a micelle-like cooperative behavior.[50A] Amyloid fibrils have been historically associated with different pathological states.[51A] However, the discovery of functional amyloid structures in almost all species[52A] and the compelling biochemical evidence indicating that oligomers are the main toxic proteospecies[53A] have emphasized the intrinsic low cytotoxicity of well-ordered amyloids. Nonetheless, cytocompatibility of the representative $I_{10}$ assemblies was assessed using HEK293T and INS-1E cell lines. Rat β-pancreatic INS-1E cells are commonly used to evaluate the toxicity of IAPP soluble prefibrillar species.[54A] As observed by fluorescence microscopy, HEK293T and INS-1E cells treated with nanorods ($KKI_{10}$, $KI_{10}$), and polymorphic twisted fibrils (I10) showed a similar calcein-AM/ethidium homodimer-1 ratio to the vehicle control (FIG. 7A). The ethidium homodimer-1 staining is associated with the loss of plasma membrane integrity whereas the calcein-AM staining correlates with intracellular esterase activity of metabolically active cells. In contrast, treatment with soluble human IAPP (hIAPP), used as a positive control of cytotoxicity,[54A] led to an increase of ethidium homodimer-1 and a decrease of calcein-AM staining. Metabolic activity of cells after 24 h treatment with these different assemblies confirmed the live/dead qualitative results (FIG. 7B). Moreover, all $I_{10}$ monomeric building blocks were also fully cytocompatible, including the uncapped $I_{10}$ monomers. Overall, cell-based assays indicated that positively capped assemblies are noncytotoxic, highlighting their possible usage as nanoparticles for biomedical applications, such as vaccines.

Overall, these results provide a novel approach to modulate the inherent polymorphism of amyloids and to obtain homogenous preparation of proteinaceous amyloid-like assemblies.

Figure 8A:
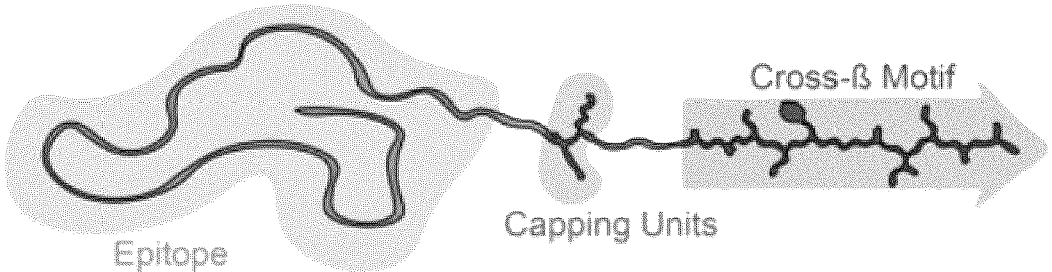
FIGS. 8A-C show the rational design of an epitope-functionalized self-assembling peptide results in uniform nanorods. Structural schematic representation of M2e-KKI10 peptide (FIG. 8A) and M2e-NRs (FIG. 8B).
Figure 8B:
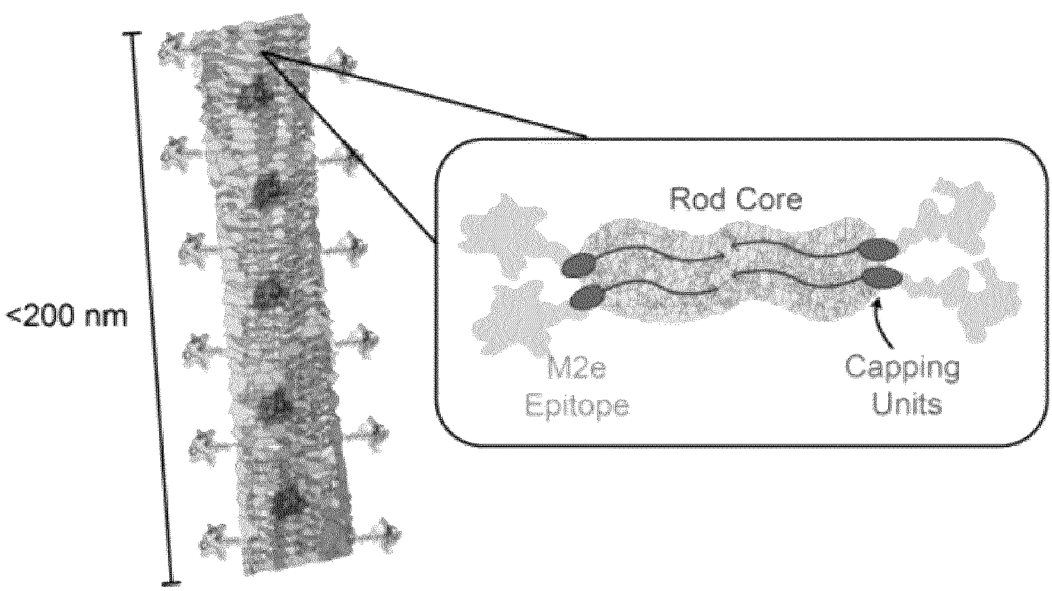

Example 4: Conserving the Nanorod Mesoscopic Architecture Upon Conjugation of a Peptide Epitope It was next tested whether the above-described approach based on the N-terminal introduction of electrostatic capping units to obtain highly uniform and small (~150 nm) rods was suitable to guide the morphology of cross-R assemblies into highly uniform epitope-functionalized NRs (FIGS. 8A-D). The M2e epitope of the influenza A virus, with sequence derived from the H1N1 strain, was conjugated to the N-terminus of the self-assembling peptide by a tripeptide spacer (GSG) (FIG. 8A). The two Cys residues of M2e were mutated to Ser (positions 17 and 19) to avoid undesired oxidation without affecting the immunogenicity of the epitope. The M2e sequence, residues 2 to 24 of virus M protein, presents the advantages of being remarkably conserved among various strains of influenza A virus of and is considered as a promising candidate for the development of a universal vaccine against influenza.[22] Moreover, it has been shown that M2e-based influenza vaccines induced a long-lasting M2e-specific antibody response.[23-24] Even though these antibodies are not neutralizing per se, they confer significant protective immunity by activating antibody-dependent cell-mediated cytotoxicity (ADCC), resulting in the elimination of infected cells.[25-26]

Figures 8C, 9A, 9B:
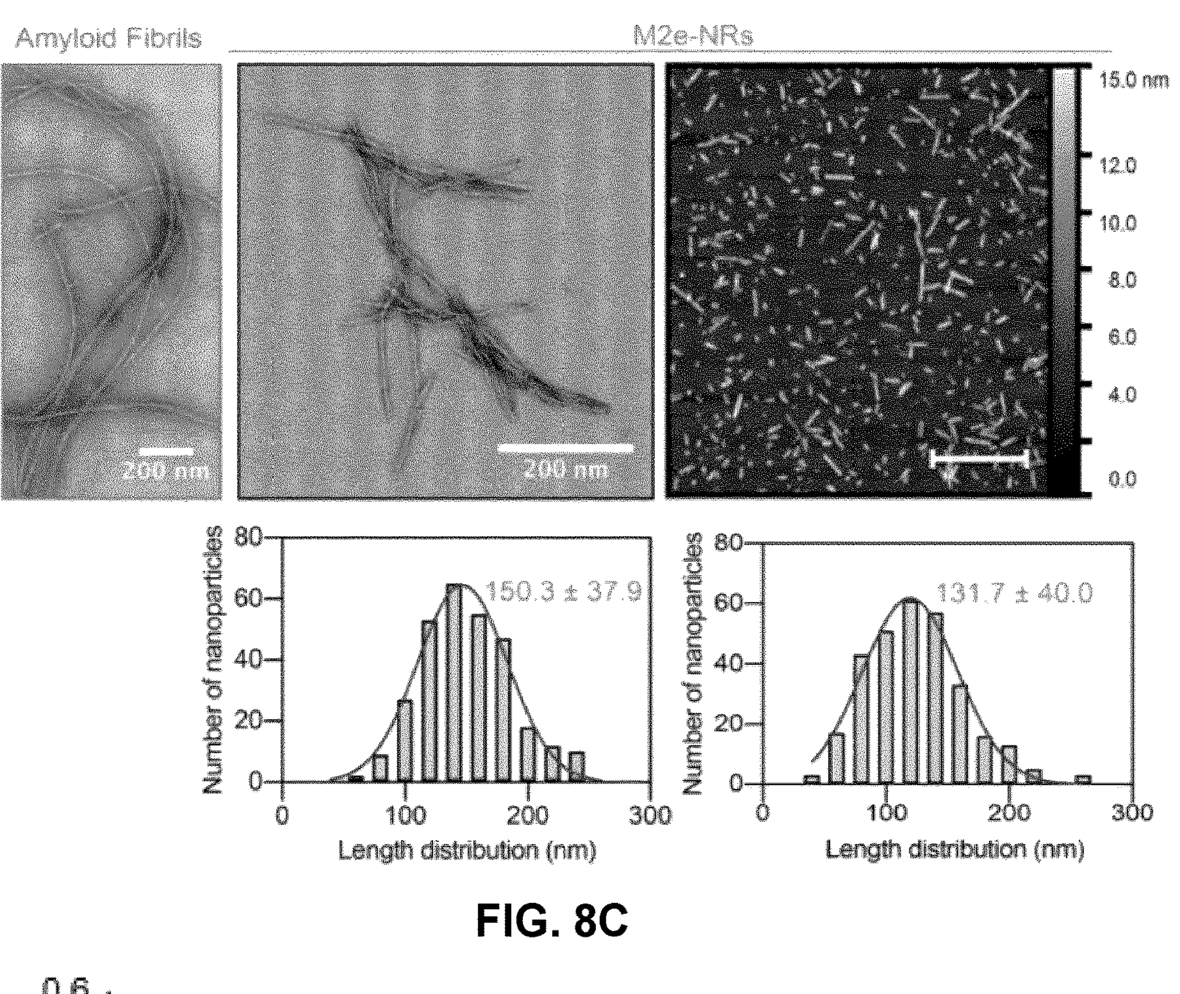
FIGS. 9A-H show that M2e-NRs present an atypical amyloid structure. Self-assembly evaluation by turbidimetry measurements (FIG. 9A) and critical aggregation concentration (CAC) measurement (FIG. 9B) using pyrene fluorescent probe. Structural characterization by far-UV circular dichroism (CD) (FIG. 9C), powder x-ray diffraction (PXRD) (FIG. 9D), 8-anilino-1-naphthalenesulfonic acid (ANS) fluorescence (FIG. 9E) and ThT fluorescence (FIG. 9F). Epitope availability determination by zeta potential (FIG. 9G) and anti-M2e indirect ELISA (FIG. 9H). Rods were assembled in LPS-free Tris buffer (50 mM, pH 7.4) under continuous rotary agitation for 72 hours at a concentration of $1.5\times10^{-3}$ M. Amyloid fibrils (IAPP) were assembled under quiescent conditions in Tris buffer (20 mM, pH 7.4) for 48 h at $50\times10^{-6}$ M.

Self-assembly was performed by incubating the chimeric M2e-functionalized $KKI_{10}$ peptides (M2e-$KKI_{10}$) at a 1.5 mM concentration in endotoxin-free Tris-HCl (50 mM, pH 7.4) for 72 h at RT under continuous rotary agitation at 40 rpm. The morphology of the resulting assemblies was initially characterized by transmission electron microscopy (TEM) (FIG. 8C). In contrast to long and polymorphic prototypical amyloid fibrils assembled from the amyloidogenic peptide IAPP, M2e-$KKI_{10}$ self-assembled into uniform nanorods (M2e-NRs) with an average length of 150.3±37.9. Atomic force microscopy (AFM) validated the mesoscopic architecture observed by TEM, with an average length of 131.7±40.0. The short and uniform length of the nanorods was also confirmed by dynamic light scattering, which indicated a Z-average of 134 nm with a polydispersity index of 0.4. Accordingly, in contrast to prototypical amyloid-like filaments previously evaluated as nanovaccine, M2e-NRs presents two morphological characteristics suitable for vaccination; (1) short length that should allow a greater draining to the lymph nodes as particles with diameter below 200 nm are known to diffuse passively in the lymph[3]; (2) high morphological uniformity that should facilitate biological and immunological characterizations. Besides, the decrease in surface charge of M2e-NRs (−12.5±5.4), in opposition to what is observed for the naked $KI_{10}$ and $KKI_{10}$ nanorods, respectively 44.5±1.9 and 47±4.8, gives an clear indication of the presence of the epitope at the surface of the rods (FIG. 9). Repetitive antigen display on the surface of the nanorods was further validated by ELISA analysis (FIG. 9) and high antigen density at the surface of the assemblies was clearly observed. Appropriate controls validated that the results obtained are attributed to specific M2e antibody binding. Thus, these results demonstrate that attaching an antigen to the N-terminal end of the self-assembling peptide does not affect the ability of the peptide to self-assemble into nanorod-like structures, and permits to expose the antigen at the surface of the nanorods.

Example 5: Cross-β Nanorods Differ from Prototypical Amyloid Assemblies

Figures 9C, 9D, 9E, 9F, 9G, 9H:
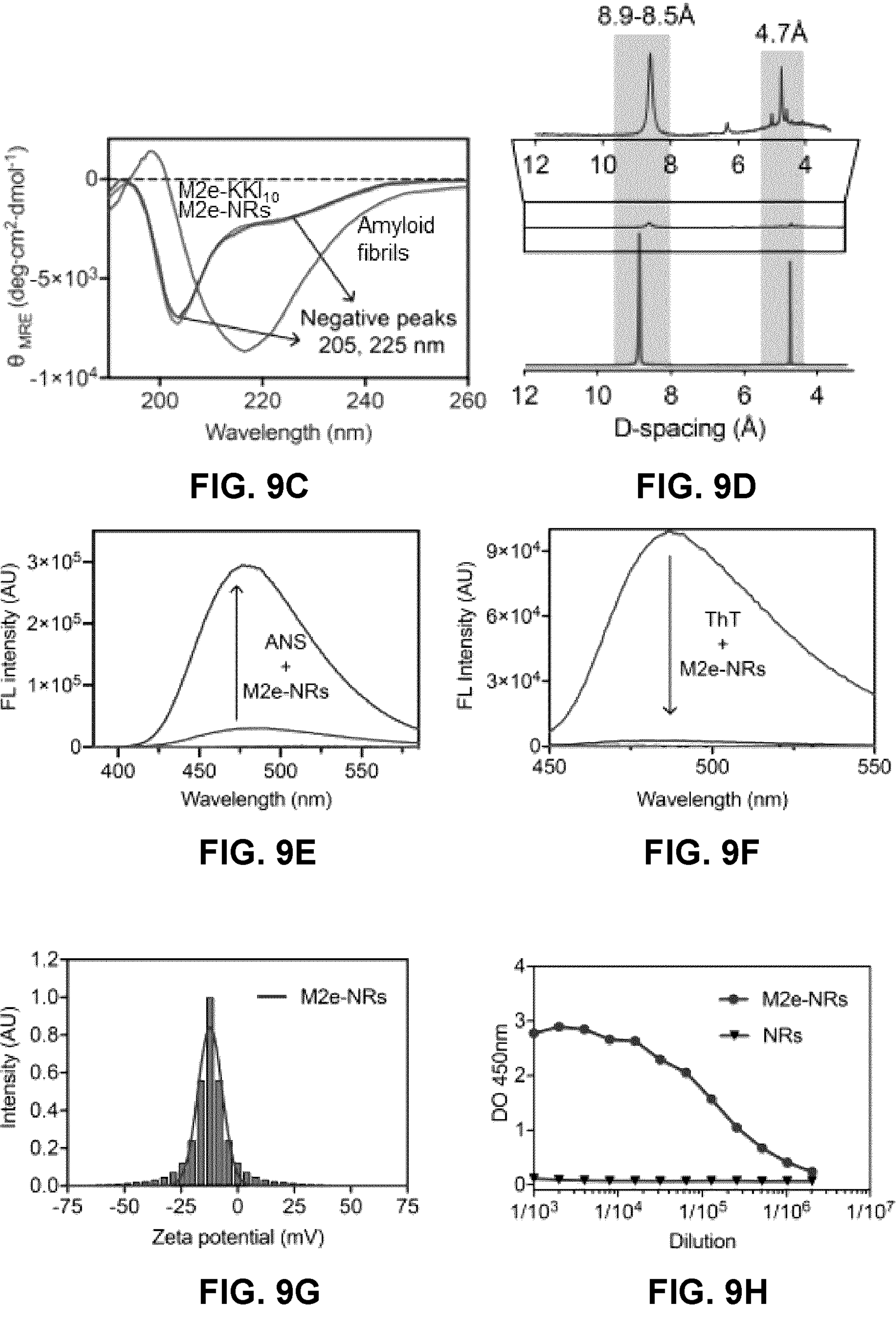

The self-assembly of the M2e-$KKI_{10}$ peptide was first monitored by turbidity measurements at 400 and 600 nm along with the observation of the apparent cloudiness and viscosity of the solutions (FIG. 9A). Then, it was assessed whether the unique biophysical characteristics previously reported for amyloid-like nanorods were preserved upon N-terminal conjugation of the M2e epitope. The critical aggregation concentration (CAC) was determined using pyrene, a probe that is sensitive to the polarity of the local environment.[27] A classical model of surfactant association was observed, suggestive of a micelle-like cooperative behavior, as observed above for $KI_{10}$ and $KKI_{10}$ nanorods. However, the CAC was notably high, 350 μM, indicating that the M2e epitope slightly hinders self-assembly. Indeed, this CAC is 10-times higher than the one observed for $KI_{10}$ nanorods (33 μM) and around 100-times higher than what has been reported for $I_{10}$ (3.5 μM). In comparison to IAPP and other amyloidogenic polypeptides, the CAC observed is even 200- to 3000-times smaller.[27-28] In addition, 8-anilino-1-naphthalenesulfonic acid (ANS) fluorescence was used to evaluate the self-assembly of monomeric M2e-$KKI_{10}$ into M2e-NRs. This fluorescent dye reported the formation of exposed hydrophobicity clusters by a sharp increase in its fluorescence emission intensity and a blue shift of the emission peak (FIG. 9E). However, since ANS fluorescence is dependent of other parameters than simple hydrophobic character, such as cationic charge, the greater increase of ANS fluorescence for M2e-NRs relative to the increase for M2e-NFs was expected.[29] Characteristics of atypical cross-β (supra)molecular structure were investigated by monitoring conformational conversion by circular dichroism (CD) spectroscopy. An identical far-UV CD spectra was observed for monomeric M2e-$KKI_{10}$ and assembled M2e-NRs (FIG. 9C). This distinctive CD signature, with two minima at 205 and 225 nm, was also identified for $KKI_{10}$ monomers as indicative of an ordered secondary structure. M2e-NRs CD spectrum clearly differs from classical amyloid, which are characterized by a single minimum at 218 nm, corresponding to a secondary structure rich in β-sheets (FIG. 9C). Furthermore, thermal denaturation of M2e-NRs was evaluated by measuring conformational changes by CD spectroscopy at three different wavelengths (222, 212, and 205 nm). Strikingly, almost no difference between the spectra were observed, indicating no apparent thermal denaturation, which is consistent with the absence of conformational change between M2e-$KKI_{10}$ monomers and M2e-NRs assemblies, and must not be attributed to amyloid properties, which are very stable with no observed melting. Powder X-ray diffraction (PXRD) of M2e-NRs revealed a diffraction pattern characterized by two sharp peaks. Bragg reflections corresponding to 4.7 Å and 8.7 Å periodic spacings were measured (FIG. 9D). The 4.7 Å meridional reflection, which arises from the spacing between hydrogen-bonded β-strands, corresponds to the prototypical cross-R signature. The 8.7 Å spacing observed, which is correlated with the inter-sheet distance, is short for cross-R assembles, but expected for dry interfaces.[30-31] Furthermore, the divergence with prototypical cross-β amyloid quaternary organization was probed by measuring thioflavin T (ThT) fluorescence and green birefringence of Congo Red (CR), two cross-β-sheet specific dye commonly used for the detection of amyloid fibrils.[32] In sharp contrast to amyloid fibrils assembled from IAPP, M2e-NRs led to negative ThT signal and CR birefringence was very weak (FIGS. 9E-F). Therefore, M2e-NRs assemblies seem to differ structurally from prototypical amyloid fibrillary assemblies.

Figure 10A:
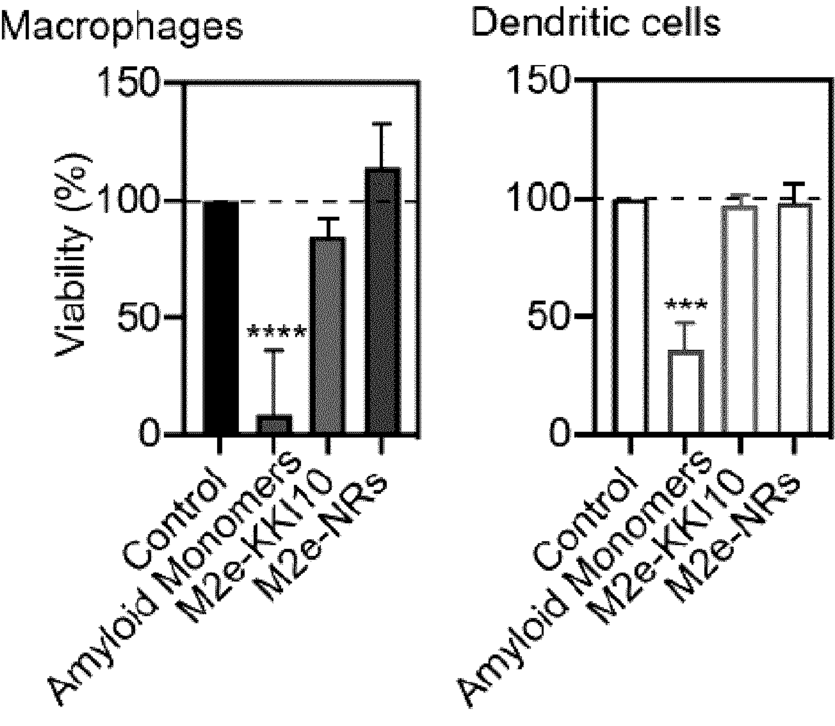
FIGS. 10A-B show that M2e-NRs overcome classical amyloid safety concerns.
Figure 10B:
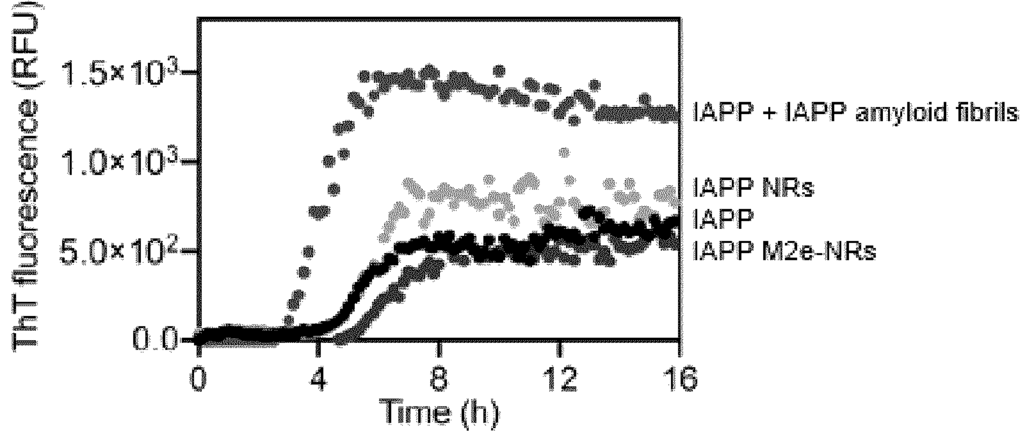

Example 6: Cross-β Nanorods are Cytocompatible and do not Cross-Seed Amyloid Formation Misfolding and aggregation of proteins into highly ordered cross-β-sheet amyloid fibrils have been historically associated with several human diseases.[33] It is increasingly accepted that the pathogenic species are both the extracellular amyloid deposits, which affect the organ integrity, and oligomers that emerge during the process of amyloid self-assembly and/or are released by mature deposits, causing direct cell death.[34-35] Accordingly, the cytocompatibility of M2e-$KKI_{10}$ monomers, i.e. before self-assembly, and M2e-NRs, i.e. after self-assembly, was initially assessed using macrophage cells (J774A.1) and dendritic-like cells (DC2.4), two cell lines commonly used as model of APCs, which play a key role for bridging the innate and adaptive immune systems. Both M2e-NRs and soluble M2e-$KKI_{10}$ monomers showed no apparent cytotoxicity, even at high concentration (150 μM). In sharp contrast, treatment with soluble amyloidogenic IAPP led to high decrease of viability of both APCs (FIG. 10A). The cross-seeding of amyloid formation, i.e. the capacity of cross-β-sheet assemblies to induce the aggregation of sequence-related proteins, constitutes a primary concern for the biomedical usage of novel nanomaterials inspired on cross-β assemblies.[19] This "infectious" effect of amyloid, similar as the prion-like effect, was evaluated by cross-seeding soluble IAPP monomers with M2e-NRs. The experiments revealed a typical IAPP nucleation-dependent polymerization kinetic without any propagation effect at 12.5 μM from 5% (mol %) of M2e-NR and NR seeds (FIG. 10B). In sharp contrast, 5% of IAPP amyloid fibrillar seeds, used as a positive control, induced a propagation effect on IAPP (FIG. 10B). As amyloid cross-seeding involve competing folding and binding events between the different species, amyloid propagation requires some compatibility between the seeds, which serves as a template for protein aggregation, and the different oligomers species promoting amyloid formation. Seeds can be homologous or heterologous, but great structural difference between the dominant species can act as physical barrier and impede the cross-seeding.[36-37] This might be the case for M2e-NRs, having a supramolecular structure that clearly differs from that of IAPP fibril, despite the similarity in the cross-β core, strongly suggesting that NRs cannot induce a amyloid prion-like effect upon injection to host.

Example 7: Cellular Uptake and Stimulation of APCs by Nanorods

Figure 11A:
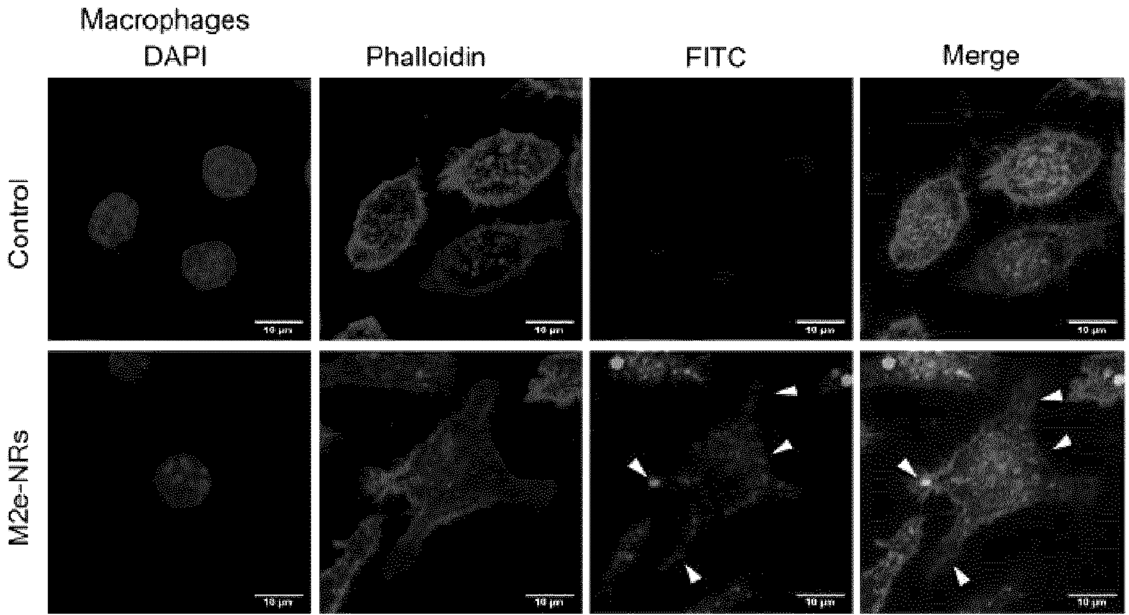
Figure 11B:
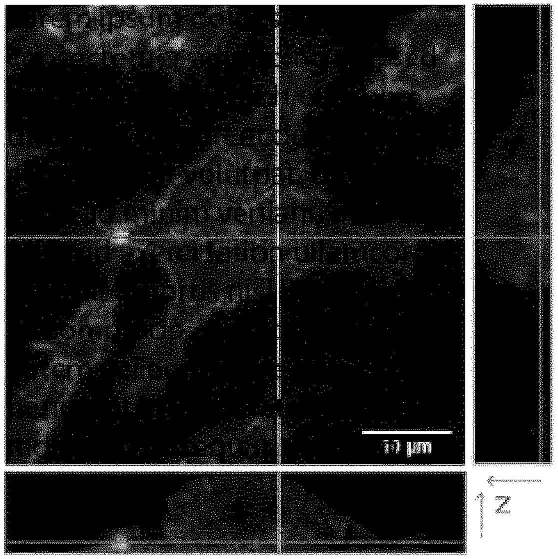
Figure 11C:
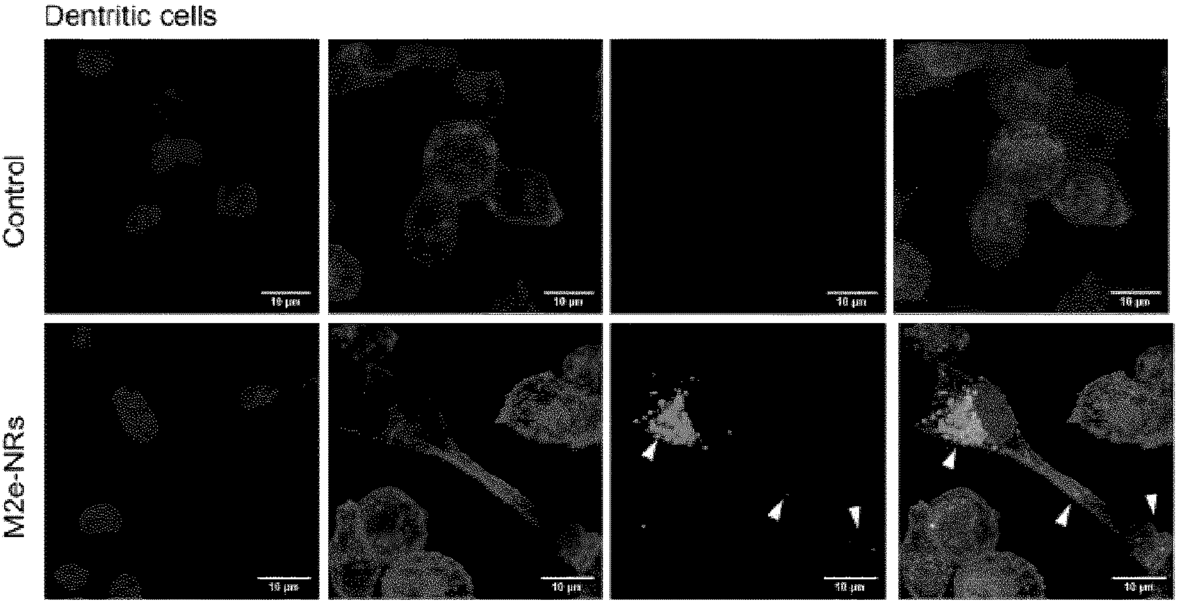
Figure 11D:
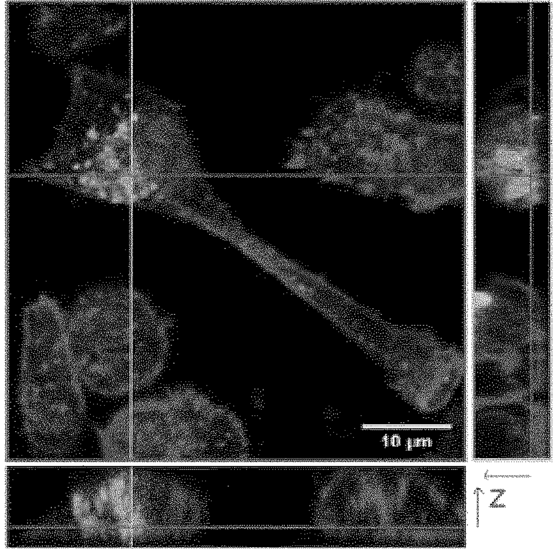

Internalization and processing of antigens by APCs, which include dendritic cells (DC), macrophages and naïve B-cells, are prerequisites for the initiation of the adaptative immune response and the induction of immunological memory.[38] This ability of APCs to uptake and process the antigens ultimately results in T cells priming and differentiation into effector subtypes (FIG. 11A). Particularly, upon activation and maturation, DCs presenting antigen through the major histocompatibility complex (MHC) class I or II, induce the activation of cytotoxic or helper T cells. The differentiation of T helper (Th) into subclass 1 and 2 can induce respectively cytotoxic and humoral response, which are critical for protective immunity. Accordingly, the internalization of fluorescently-labeled M2e-NRs (FITC-M2e-NRs) by J774A.1 and DC2.4 cells was evaluated using confocal microscopy and flow cytometry. Fluorescent M2e-NRs were morphologically identical to unlabeled M2e-NRs previously characterized. Confocal microscopy revealed that the labeled nanoparticles were efficiently uptaken by the MCs and DCs (FIG. 11B). Z-stack projections and orthogonal views revealed that the FITC fluorescence was located inside the cells, confirming that the nanorods were internalized (FIGS. 11A-D). Nevertheless, some fluorescent aggregates were also visible at the cell surface, indicating that assemblies could gathered at the cell membrane. A change in DCs and MCs morphology was also observed, suggesting APC activation and maturation. The internalization was then quantified by flow cytometry, which showed high levels of M2e-NRs uptake by DCs and MCs at 50 and 100 μM. Indeed, in both cases, after 30 min and 1 h of incubation, over 65% of the cells were FITC-positive. A slight decrease in FITC fluorescence was observed after 3 h incubation, indicative of FITC-M2e-NRs degradation in phagolysosomes and/or antigen processing. The extent of nanorods uptake by APCs was concentration-dependent, being higher at 100 μM (right bars in FIGS. 11E and H) than at 50 μM (middle bars in FIGS. 11E and H) of M2e-NRs (FIGS. 11E-J). Trypan blue was used to quench the extracellular fluorescence and discriminate internalized fibrils from membrane-bound assemblies. This confirmed that the fluorescence emitted from the fibrils was indeed intracellular.

Moreover, APCs also benefit from a broad specificity to detect pathogen-associated molecular patterns (PAMP) and danger-associated molecular patterns (DAMP) via pattern recognition receptors (PRRs). The binding of ligands to PRRs, such as Toll-like receptors (TLRs) results in the activation of a number of signaling pathways, including the nuclear factor kappa B (NF-κB) signaling pathway, and the upregulation of cytokines, chemokines and co-stimulatory molecules. Ultimately, the engagement of TLRs lead to activation and maturation of APCs, particularly DC.[39] Moreover, TLRs activation, which transcriptionally induce pro-IL-18 and pro-IL-1β, also cooperate with the inflammasome to IL-18 and IL-1 β secretion.[40] Accordingly, the capacity of the cross-R nanorods to activate the innate immune response through TLR2, using HEK-Blue mTLR2 cells that overexpress TLR2 and a NF-κB-inducible reporter gene SEAP (secreted embryonic alkaline phosphatase), was evaluated. Cells were exposed to increasing concentrations of M2e-NRs for 16 h and a concentration-dependent SEAP activity, associated with NF-κB activation, was measured upon treatment with CsgA fibrils (FIG. 11I). SEAP activity was measured for cells treated with the TLR2 agonist Pam2CSK4 (positive control) whereas no activity was measured for cell treated with the soluble monomeric epitope M2e (negative control). Moreover, the activation of dendritic-like cells DC2.4 by the nanorods was assessed by measuring the upregulation of MHCII by flow cytometry and concentration-dependent increase of cell-surface MHCII was observed (FIG. 11J).

Example 8: Evaluation of the Adjuvant Capacity of the Nanorods in Mice

Figure 12D:
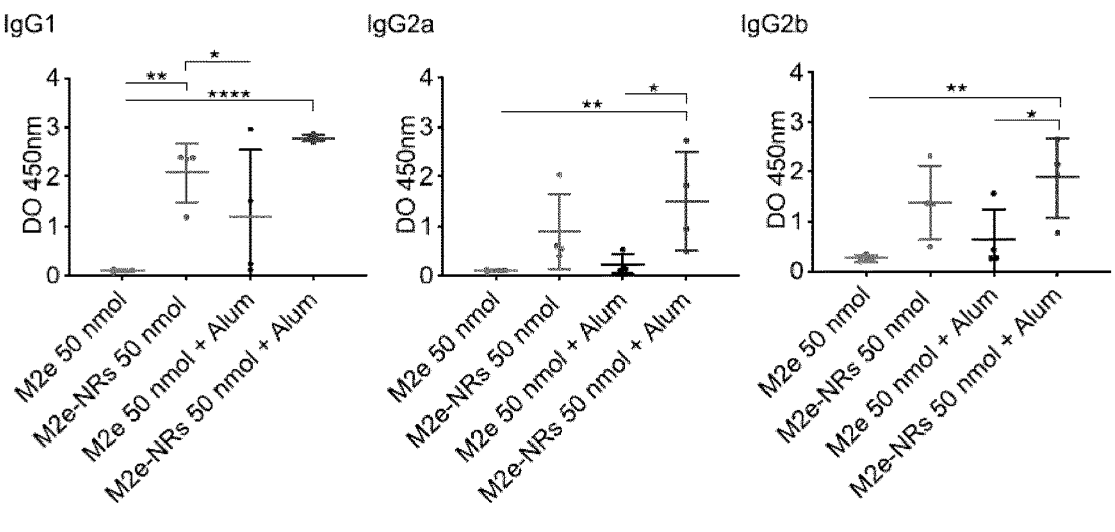

Results of cell-based assays revealed that M2e-$KKI_{10}$-NRs deliver efficiently the immunogenic antigen into macrophages and DCs, are fully cytocompatible and readily activate the TLR2. Accordingly, the potential of NR-based influenza nanovaccine was next evaluated by immunizing BALB/c mice subcutaneously (SC) with M2e-NRs in the presence or absence of Alum adjuvant. Mice were immunized (10, 50 and 100 nmol/dose) three times (every 14 days) with a volume of 100 μl per injection. The kinetics of M2e-specific antibody response (IgG) over time was evaluated using blood samples collected from the saphenous vein at day 0, 14, 28 and 42 post-primary immunization (PPI) by ELISA. In absence of Alum, the monomeric M2e epitope (50 nmol/dose) did not raise any significant level of epitope-specific IgG, even after two boosts (FIG. 12). When co-injected with Alum, the monomeric M2e peptide raised a very low antibody response at day 28 PPI, while a significant antibody titer was observed after two boosts. In sharp contrast, when the M2e epitope was conjugated to the assembled NR scaffold, a strong increase of antibody titers was observed after a single boost, i.e. at day 28 PPI. Notably, results showed that injection of 10 nmol M2e-$KKI_{10}$ NRs elicited a similar kinetics of IgG response to the 100 nmol dose (FIG. 12B). Interestingly, while the Alum-adjuvanted M2e-$KKI_{10}$ NRs showed a somewhat robust anti-M2e response at day 14 PPI, i.e. only with the primary immunization, this vaccine preparation led to a similar antibody response to M2e-$KKI_{10}$ NRs alone (at 50 nmol) at day 28 and 42 PPI, suggesting that the NR-scaffold acts as a self-adjuvanted nanovaccine on its own. Finally, there was no significant level of IgG raised against the $KKI_{10}$ scaffold peptide in mice immunized with all the different assemblies, indicating that the NR platform is not immunogenic on its own. The isotypes of IgG were determined to evaluate the predominant antibodies produced in mice in response to NR-based vaccine. IgG1, typical of a Th2 antibody response[53], was the predominant IgG subclasses induced by the nanovaccine (FIG. 12D). IgG2a and IgG2b, prototypical of Th1 cellular response, were also produced for the NRs in absence of Alum, but at lower level. A more robust mixed Th1/Th2 M2e-specific response was observed for the vaccine preparation supplemented with Alum. Overall, these results highlight the potential of cross-R self-assembling peptide as immunogenic carrier by triggering an immunological response against a highly conserved antigenic determinant derived from the influenza A virus.

Figure 13A:
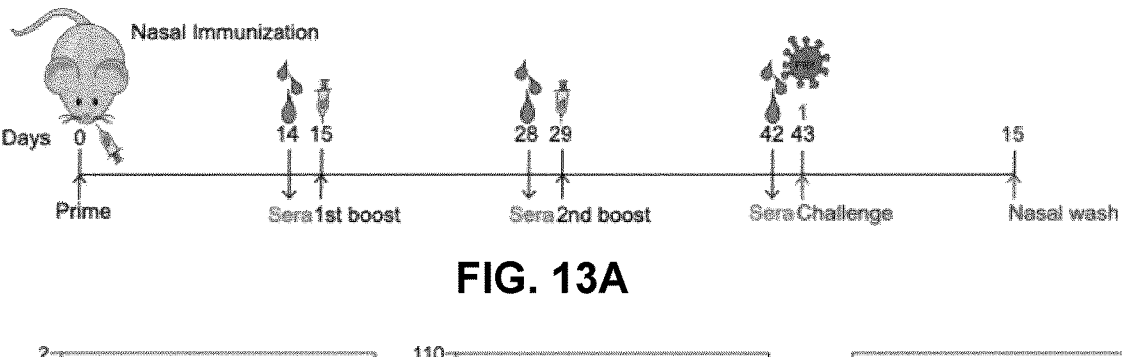
FIGS. 13A-D show that nasal immunization with M2e-NRs protected against a homologous virus challenge.
Figure 13B:
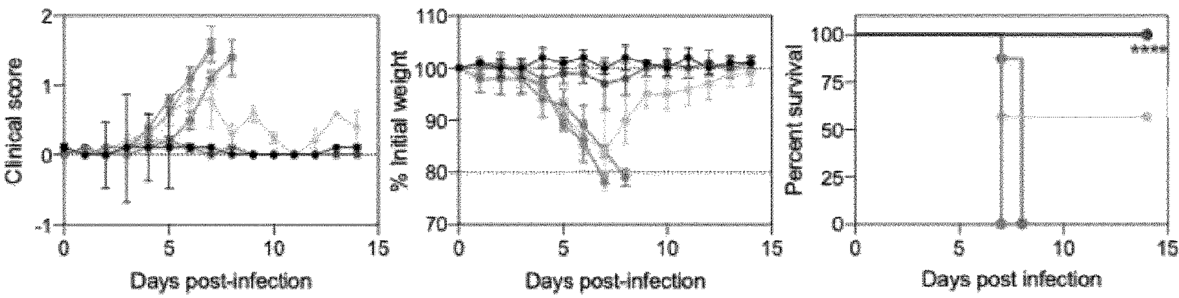
Figure 13C:
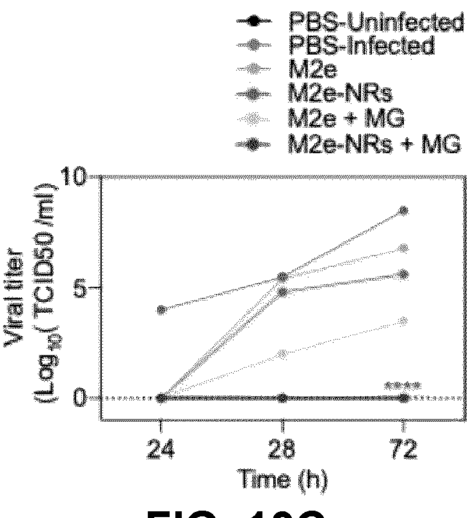
Figure 13D:
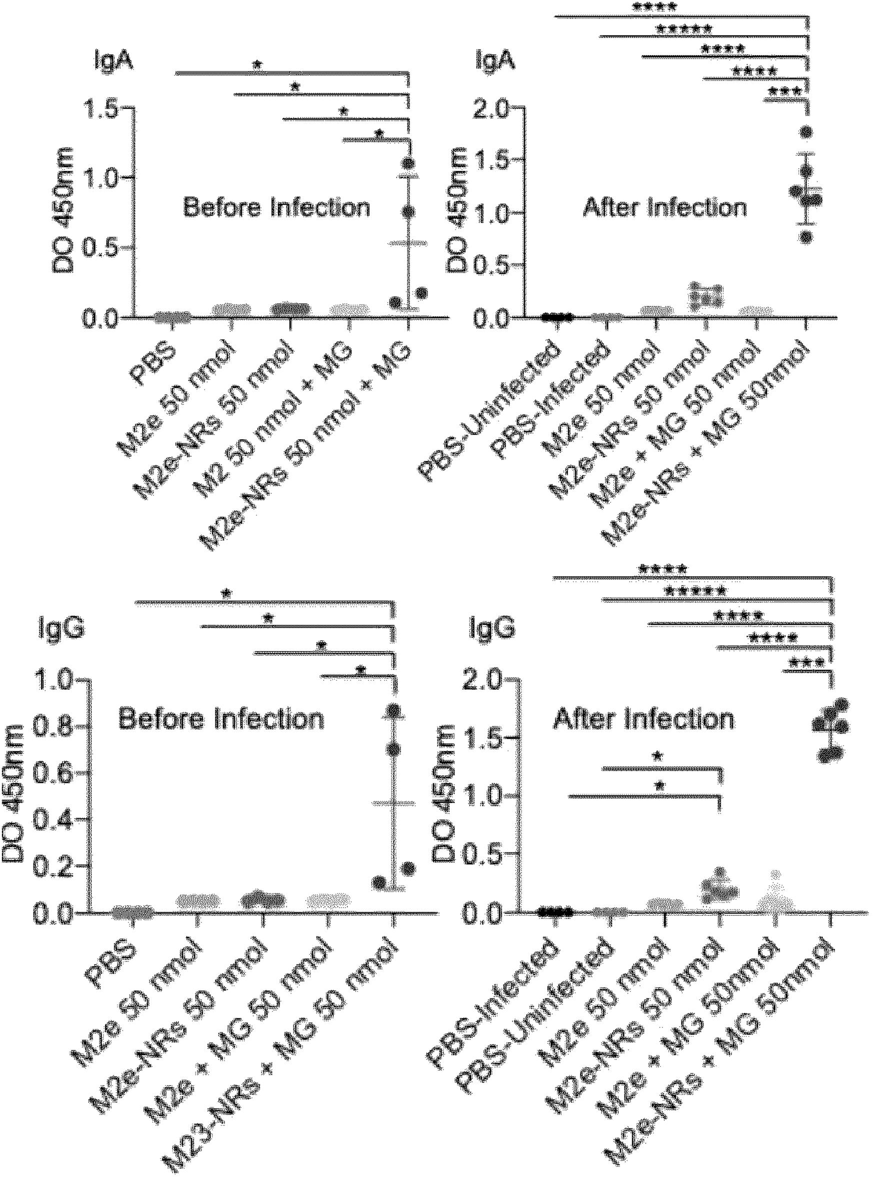
Figure 14A:
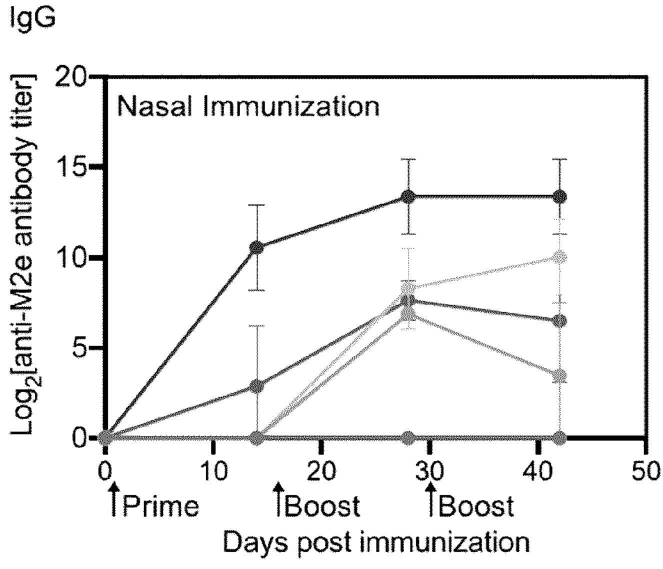
FIGS. 14A-C show that M2e-NRs nasal vaccination induced a specific IgG immune response against M2e. M2e-specific serum IgG antibody kinetics (FIG. 14A) and final titers (FIG. 14B).
Figure 14B:
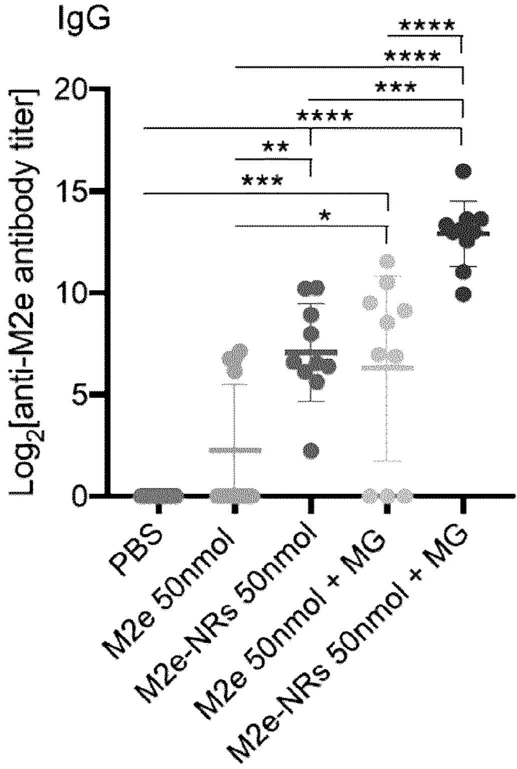
Figure 14C:
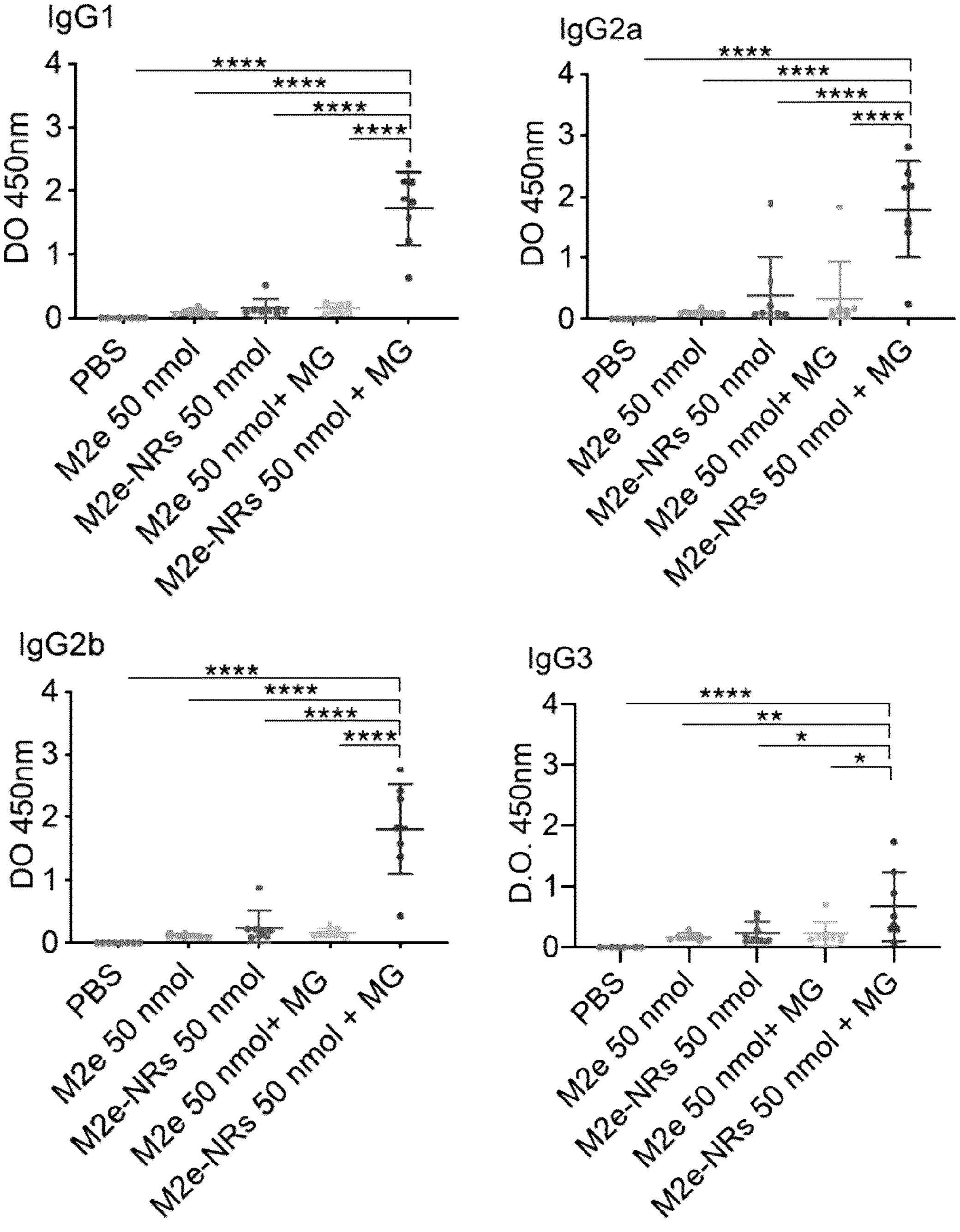

Example 9: Synthetic M2e-NR Nanovaccine Protects Mice Against a Lethal Experimental Challenge with the H1N1 Influenza a Virus The respiratory mucosa is the primary portal of entry of the influenza virus and upon initially infection of the upper respiratory tract, the virus reaches the lower respiratory tract, leading to flu progression. Accordingly, the nasal-associated lymphoid tissue is considered as an inductive site for humoral and cellular immune responses and represents a promising target for vaccines against the influenza A virus. Particularly, the nanoscale size and the shape of the NRs are particularly well suited for intranasal immunization, a very attracting vaccination approach against flu. In this context, mice were immunized by intranasal (in) instillation with the nanovaccine using the immunization scheme described above (1× primary immunization followed by two boosts every 14 days) before being experimentally challenged with $5\times LD_{50}$ of influenza A/PR8/1934 H1N1 by in instillation. Weight loss and clinical signs were monitored daily after infection and a weight loss of 20% or more of initial weight and/or any clinical signs of an intensity of three were considered critical and mice were euthanized. Challenged mice who received the M2e alone and M2e$KKI_{10}$ NRs, in absence of the adjuvant Montanide gel (MG), showed 100% mortality with progression of weight loss and clinical symptoms similar to mice immunized with the negative PBS control (FIGS. 13A-B). In sharp contrast, when the M2e-NRs were co-instilled with MG, the vaccine preparation led a quasi-absence of weight loss and clinical signs, which led to 100% survival for the immunized mice. Bronchoalveolar lavage (BAL) fluid was harvested for each mice (before (4 mice were sacrificed) or after infection) to determine secretory IgG and IgA antibody. Strikingly and in agreement with the 100% survival, mice immunized with the M2e-NRs+MG vaccine preparation showed a robust production of M2e-specific IgG and IgA antibody, while for the other vaccine formulations, no antibodies were detected in BAL (FIG. 13D). Finally, the M2e-specific IgG antibody response in sera was evaluated by ELISA at day 14, 28 and 42 PPI of mice immunized IN. As expected, the M2e-NRs+MG vaccine formulations led to robust sera anti-M2e immune responses, with the production IgG1, IgG2a, IgG2b and IgG3, indicative of a mixed Th1/Th2 immune response (FIG. 14).

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Wei, C.-J.; Crank, M. C.; Shiver, J.; Graham, B. S.; Mascola, J. R.; Nabel, G. J., Next-generation influenza vaccines: opportunities and challenges. Nature Reviews Drug Discovery 2020, 19 (4), 239-252.
2. Levine, M. M.; Sztein, M. B., Vaccine development strategies for improving immunization: the role of modern immunology. Nat Immunol 2004, 5 (5), 460-4.
3. Al-Halifa, S.; Gauthier, L.; Arpin, D.; Bourgault, S.; Archambault, D., Nanoparticle-Based Vaccines Against Respiratory Viruses. Frontiers in immunology 2019, 10, 22.
4. Irvine, D. J.; Swartz, M. A.; Szeto, G. L., Engineering synthetic vaccines using cues from natural immunity. Nat Mater 2013, 12 (11), 978-990.
5. Pruksakorn, S.; Currie, B.; Brandt, E.; Phornphutkul, C.; Hunsakunachai, S.; Manmontri, A.; Robinson, J. H.; Kehoe, M. A.; Galbraith, A.; Good, M. F., Identification of T cell autoepitopes that cross-react with the C-terminal segment of the M protein of group A streptococci. Int Immunol 1994, 6 (8), 1235-44.
6. Azmi, F.; Ahmad Fuaad, A. A. H.; Skwarczynski, M.; Toth, I., Recent progress in adjuvant discovery for peptide-based subunit vaccines. Hum Vaccin Immunother 2014, 10 (3), 778-796.
7. Pati, R.; Shevtsov, M.; Sonawane, A., Nanoparticle Vaccines Against Infectious Diseases. Front Immunol 2018, 9, 2224-2224.
8. Eskandari, S.; Guerin, T.; Toth, I.; Stephenson, R. J., Recent advances in self-assembled peptides: Implications for targeted drug delivery and vaccine engineering. Adv Drug Deliv Rev 2017, 110-111, 169-187.
9. Al-Halifa, S.; Babych, M.; Zottig, X.; Archambault, D.; Bourgault, S., Amyloid self-assembling peptides: Potential applications in nanovaccine engineering and biosensing. Peptide Science 2019, 111 (1), e24095.
10. Rudra, J. S.; Mishra, S.; Chong, A. S.; Mitchell, R. A.; Nardin, E. H.; Nussenzweig, V.; Collier, J. H., Self-assembled peptide nanofibers raising durable antibody responses against a malaria epitope. Biomaterials 2012, 33 (27), 6476-6484.
11. Babych, M.; Bertheau-Mailhot, G.; Zottig, X.; Dion, J.; Gauthier, L.; Archambault, D.; Bourgault, S., Engineering and evaluation of amyloid assemblies as a nanovaccine against the Chikungunya virus. Nanoscale 2018, 10 (41), 19547-19556.
14. Tywoniuk, B.; Yuan, Y.; McCartan, S.; Szydfowska, B. M.; Tofoleanu, F.; Brooks, B. R.; Buchete, N.-V., Amyloid Fibril Design: Limiting Structural Polymorphism in Alzheimer's Aβ Protofilaments. The Journal of Physical Chemistry B 2018, 122 (49), 11535-11545.
15. Wen, Y.; Collier, J. H., Supramolecular peptide vaccines: tuning adaptive immunity. Curr Opin Immunol 2015, 35, 73-9.
16. Bachmann, M. F.; Jennings, G. T., Vaccine delivery: a matter of size, geometry, kinetics and molecular patterns. Nature reviews. Immunology 2010, 10 (11), 787-96.
17. Luo, Q.; Hou, C.; Bai, Y.; Wang, R.; Liu, J., Protein Assembly: Versatile Approaches to Construct Highly Ordered Nanostructures. Chemical Reviews 2016, 116 (22), 13571-13632.
18. Stefani, M.; Dobson, C. M., Protein aggregation and aggregate toxicity: new insights into protein folding, misfolding diseases and biological evolution. J Mol Med (Berl) 2003, 81 (11), 678-99.
19. Ren, B.; Zhang, Y.; Zhang, M.; Liu, Y.; Zhang, D.; Gong, X.; Feng, Z.; Tang, J.; Chang, Y.; Zheng, J., Fundamentals of cross-seeding of amyloid proteins: an introduction. Journal of Materials Chemistry B 2019, 7 (46), 7267-7282.
20. Honda, R., Amyloid-beta Peptide Induces Prion Protein Amyloid Formation: Evidence for Its Widespread Amyloidogenic Effect. Angew Chem Int Ed Engl 2018, 57 (21), 6086-6089.
21. Zottig, X.; Al-Halifa, S.; Babych, M.; Quittot, N.; Archambault, D.; Bourgault, S., Guiding the Morphology of Amyloid Assemblies by Electrostatic Capping: from Polymorphic Twisted Fibrils to Uniform Nanorods. Small 2019, 15 (33), 1901806.
22. Mezhenskaya, D.; Isakova-Sivak, I.; Rudenko, L., M2e-based universal influenza vaccines: a historical overview and new approaches to development. J Biomed Sci 2019, 26 (1), 76.
23. Kim, M. C.; Lee, J. S.; Kwon, Y. M.; O, E.; Lee, Y. J.; Choi, J. G.; Wang, B. Z.; Compans, R. W.; Kang, S. M., Multiple heterologous M2 extracellular domains presented on virus-like particles confer broader and stronger M2 immunity than live influenza A virus infection. Antiviral Res 2013, 99 (3), 328-35.
24. Schotsaert, M.; Ysenbaert, T.; Smet, A.; Schepens, B.; Vanderschaeghe, D.; Stegalkina, S.; Vogel, T. U.; Callewaert, N.; Fiers, W.; Saelens, X., Long-Lasting Cross-Protection Against Influenza A by Neuraminidase and M2e-based immunization strategies. Sci Rep 2016, 6, 24402.
25. Jegerlehner, A.; Schmitz, N.; Storni, T.; Bachmann, M. F., Influenza A vaccine based on the extracellular domain of M2: weak protection mediated via antibody-dependent NK cell activity. J Immunol 2004, 172 (9), 5598-605.
26. Simhadri, V. R.; Dimitrova, M.; Mariano, J. L.; Zenarruzabeitia, O.; Zhong, W.; Ozawa, T.; Muraguchi, A.; Kishi, H.; Eichelberger, M. C.; Borrego, F., A Human Anti-M2 Antibody Mediates Antibody-Dependent Cell-Mediated Cytotoxicity (ADCC) and Cytokine Secretion by Resting and Cytokine-Preactivated Natural Killer (NK) Cells. PLoS One 2015, 10 (4), e0124677.
27. Novo, M.; Freire, S.; Al-Soufi, W., Critical aggregation concentration for the formation of early Amyloid-beta (1-42) oligomers. Sci Rep 2018, 8 (1), 1783.
28. Brender, J. R.; Krishnamoorthy, J.; Sciacca, M. F. M.; Vivekanandan, S.; D'Urso, L.; Chen, J.; La Rosa, C.; Ramamoorthy, A., Probing the Sources of the Apparent Irreproducibility of Amyloid Formation: Drastic Changes in Kinetics and a Switch in Mechanism Due to Micellelike Oligomer Formation at Critical Concentrations of IAPP. The Journal of Physical Chemistry B 2015, 119 (7), 2886-2896.
29. Matulis, D.; Lovrien, R., 1-Anilino-8-Naphthalene Sulfonate Anion-Protein Binding Depends Primarily on Ion Pair Formation. Biophysical Journal 1998, 74 (1), 422-429.

30. Margittai, M.; Langen, R., Fibrils with parallel in-register structure constitute a major class of amyloid fibrils: molecular insights from electron paramagnetic resonance spectroscopy. Q Rev Biophys 2008, 41 (3-4), 265-97.

31. Nelson, R.; Sawaya, M. R.; Balbirnie, M.; Madsen, A. Ø; Riekel, C.; Grothe, R.; Eisenberg, D., Structure of the cross-β spine of amyloid-like fibrils. Nature 2005, 435, 773.

32. Girych, M.; Gorbenko, G.; Maliyov, I.; Trusova, V.; Mizuguchi, C.; Saito, H.; Kinnunen, P., Combined thioflavin T-Congo red fluorescence assay for amyloid fibril detection. Methods Appl Fluoresc 2016, 4 (3), 034010.

33. Chiti, F.; Dobson, C. M., Protein Misfolding, Amyloid Formation, and Human Disease: A Summary of Progress Over the Last Decade. Annual review of biochemistry 2017, 86, 27-68.

34. Zraika, S.; Hull, R. L.; Verchere, C. B.; Clark, A.; Potter, K. J.; Fraser, P. E.; Raleigh, D. P.; Kahn, S. E., Toxic oligomers and islet beta cell death: guilty by association or convicted by circumstantial evidence-?Diabetologia 2010, 53 (6), 1046-1056.

35. Roberts, H. L.; Brown, D. R., Seeking a mechanism for the toxicity of oligomeric alpha-synuclein. Biomolecules 2015, 5 (2), 282-305.

36. Cheng, P.-N.; Liu, C.; Zhao, M.; Eisenberg, D.; Nowick, J. S., Amyloid β-sheet mimics that antagonize protein aggregation and reduce amyloid toxicity. Nature Chemistry 2012, 4 (11), 927-933.

37. Hard, T.; Lendel, C., Inhibition of amyloid formation. J Mol Biol 2012, 421 (4-5), 441-65.

38. Black, M.; Trent, A.; Tirrell, M.; Olive, C., Advances in the design and delivery of peptide subunit vaccines with a focus on toll-like receptor agonists. Expert Rev Vaccines 2010, 9 (2), 157-73.

39. Dowling, J. K.; Mansell, A., Toll-like receptors: the swiss army knife of immunity and vaccine development. Clin Transl Immunology 2016, 5 (5), e85-e85.

40. Schroder, K.; Tschopp, J., The inflammasomes. Cell 2010, 140 (6), 821-32.

41. Carufel, C. A.; Nguyen, P. T.; Sahnouni, S.; Bourgault, S., New insights into the roles of sulfated glycosaminoglycans in islet amyloid polypeptide amyloidogenesis and cytotoxicity. Peptide Science 2013, 100 (6), 645-655.

42. Abedini, A.; Raleigh, D. P., Incorporation of Pseudoproline Derivatives Allows the Facile Synthesis of Human IAPP, a Highly Amyloidogenic and Aggregation-Prone Polypeptide. Organic Letters 2005, 7 (4), 693-696.

43. Nguyen, P. T.; Zottig, X.; Sebastiao, M.; Bourgault, S., Role of Site-Specific Asparagine Deamidation in Islet Amyloid Polypeptide Amyloidogenesis: Key Contributions of Residues 14 and 21. Biochemistry 2017, 56 (29), 3808-3817.

44. He, Y.; Barker, S. J.; MacDonald, A. J.; Yu, Y.; Cao, L.; Li, J.; Parhar, R.; Heck, S.; Hartmann, S.; Golenbock, D. T.; Jiang, S.; Libri, N. A.; Semper, A. E.; Rosenberg, W. M.; Lustigman, S., Recombinant Ov-ASP-1, a Th1-biased protein adjuvant derived from the helminth Onchocerca volvulus, can directly bind and activate antigen-presenting cells. J Immunol 2009, 182 (7), 4005-16.

45. Cao, M.; Lu, S.; Zhao, W.; Deng, L.; Wang, M.; Wang, J.; Zhou, P.; Wang, D.; Xu, H.; Lu, J. R., Peptide Self-Assembled Nanostructures with Distinct Morphologies and Properties Fabricated by Molecular Design. ACS Applied Materials & Interfaces 2017, 9 (45), 39174-39184.

46. Becktel, W. J.; Schellman, J. A., Protein stability curves. Biopolymers 1987, 26 (11), 1859-77.

47. Hervé, P.-L.; Raliou, M.; Bourdieu, C.; Dubuquoy, C.; Petit-Camurdan, A.; Bertho, N.; Eléouët, J.-F.; Chevalier, C.; Riffault, S., A novel subnucleocapsid nanoplatform for mucosal vaccination against influenza virus that targets the ectodomain of matrix protein 2. J Virol 2014, 88 (1), 325-338.

48. De Filette, M.; Min Jou, W.; Birkett, A.; Lyons, K.; Schultz, B.; Tonkyro, A.; Resch, S.; Fiers, W., Universal influenza A vaccine: optimization of M2-based constructs. Virology 2005, 337 (1), 149-61.

49. Reed, L. J.; Muench, H., A SIMPLE METHOD OF ESTIMATING FIFTY PERCENT ENDPOINTS12. American Journal of Epidemiology 1938, 27 (3), 493-497.

1A. a) G. Wei, Z. Su, N. P. Reynolds, P. Arosio, I. W. Hamley, E. Gazit, R. Mezzenga, Chem. Soc. Rev. 2017, 46, 4661; b) T. P. J. Knowles, R. Mezzenga, Adv. Mater. 2016, 28, 6546.

2A. M. Yolamanova, C. Meier, A. K. Shaytan, V. Vas, C. W. Bertoncini, F. Arnold, O. Zirafi, S. M. Usmani, J. A. Muller, D. Sauter, C. Goffinet, D. Palesch, P. Walther, N. R. Roan, H. Geiger, O. Lunov, T. Simmet, J. Bohne, H. Schrezenmeier, K. Schwarz, L. Standker, W.-G. Forssmann, X. Salvatella, P. G. Khalatur, A. R. Khokhlov, T. P. J. Knowles, T. Weil, F. Kirchhoff, J. Munch, Nat. Nanotechnol. 2013, 8, 130.

3A. a) M. Babych, G. Bertheau-Mailhot, X. Zottig, J. Dion, L. Gauthier, D. Archambault, S. Bourgault, Nanoscale 2018, 10, 19547; b) J. S. Rudra, Y. F. Tian, J. P. Jung, J. H. Collier, Proc. Natl. Acad. Sci. USA 2010, 107, 622; c) S. Al-Halifa, L. Gauthier, D. Arpin, S. Bourgault, D. Archambault, Front. Immunol. 2019, 10, 22.

4A. E. Genové, C. Shen, S. Zhang, C. E. Semino, Biomaterials 2005, 26, 3341.

5A. X.-M. Zhou, A. Entwistle, H. Zhang, A. P. Jackson, T. O. Mason, U. Shimanovich, T. P. J. Knowles, A. T. Smith, E. B. Sawyer, S. Perrett, ChemCatChem 2014, 6, 1961.

6A. D. Men, Y.-C. Guo, Z.-P. Zhang, H.-P. Wei, Y.-F. Zhou, Z.-Q. Cui, X.-S. Liang, K. Li, Y. Leng, X.-Y. You, X.-E. Zhang, Nano Lett. 2009, 9, 2246.

7A. Y. Hu, R. Lin, P. Zhang, J. Fern, A. G. Cheetham, K. Patel, R. Schulman, C. Kan, H. Cui, ACS Nano 2016, 10, 880.

8A. A. Trent, R. Marullo, B. Lin, M. Black, M. Tirrell, Soft Matter 2011, 7, 9572.

9A. S. Zhang, Nat. Biotechnol. 2003, 21, 1171.

10A. E. T. Pashuck, S. I. Stupp, J. Am. Chem. Soc. 2010, 132, 8819.

11A. H. Cui, T. Muraoka, A. G. Cheetham, S. I. Stupp, Nano Lett. 2009, 9, 945.

12A. J. P. Jung, J. Z. Gasiorowski, J. H. Collier, Biopolymers 2010, 94, 49.

13A. a) T. P. Knowles, A. W. Fitzpatrick, S. Meehan, H. R. Mott, M. Vendruscolo, C. M. Dobson, M. E. Welland, Science 2007, 318, 1900; b) Q. Luo, C. Hou, Y. Bai, R. Wang, J. Liu, Chem. Rev. 2016, 116, 13571.

14A. R. Nelson, M. R. Sawaya, M. Balbirnie, A. Ø. Madsen, C. Riekel, R. Grothe, D. Eisenberg, *Nature* 2005, 435, 773.

15A. G. A. Hudalla, T. Sun, J. Z. Gasiorowski, H. Han, Y. F. Tian, A. S. Chong, J. H. Collier, *Nat. Mater.* 2014, 13, 829.

16A. a) C. Valéry, S. Deville-Foillard, C. Lefebvre, N. Taberner, P. Legrand, F. Meneau, C. Meriadec, C. Delvaux, T. Bizien, E. Kasotakis, C. Lopez-Iglesias, A. Gall, S. Bressanelli, M.-H. Le Du, M. Paternostre, F. Artzner, *Nat. Commun.* 2015, 6, 7771; b) D. J. Glover, L. Giger, S. S. Kim, R. R. Naik, D. S. Clark, Nat. Commun. 2016, 7, 11771.

17A. M. Diaz-Caballero, S. Navarro, I. Fuentes, F. Teixidor, S. Ventura, *ACS Nano* 2018, 12, 5394.

18A. E. E. Meyer, K. J. Rosenberg, J. Israelachvili, *Proc. Natl. Acad. Sci. USA* 2006, 103, 15739.

19A. S. E. Paramonov, H.-W. Jun, J. D. Hartgerink, *J. Am. Chem. Soc.* 2006, 128, 7291.

20A. a) J. Shi, Y. Gao, Z. Yang, B. Xu, Beilstein J. Org. Chem. 2011, 7, 167; b) J. Zhou, X. Du, Y. Gao, J. Shi, B. Xu, J. Am. Chem. Soc. 2014, 136, 2970; c) M. Ma, Y. Kuang, Y. Gao, Y. Zhang, P. Gao, B. Xu, *J. Am. Chem. Soc.* 2010, 132, 2719.

21A. S.-T. Wang, Y. Lin, R. K. Spencer, M. R. Thomas, A. I. Nguyen, N. Amdursky, E. T. Pashuck, S. C. Skaalure, C. Y. Song, P. A. Parmar, R. M. Morgan, P. Ercius, S. Aloni, R. N. Zuckermann, M. M. Stevens, *ACS Nano* 2017, 11, 8579.

22A. E. Gazit, *Angew. Chem., Int. Ed.* 2002, 41, 257.

23A. R. Pellarin, P. Schuetz, E. Guarnera, A. Caflisch, *J. Am. Chem. Soc.* 2010, 132, 14960.

24A. W. Close, M. Neumann, A. Schmidt, M. Hora, K. Annamalai, M. Schmidt, B. Reif, V. Schmidt, N. Grigorieff, M. Fandrich, *Nat. Commun.* 2018, 9, 699.

25A. J. J. Balbach, Y. Ishii, O. N. Antzutkin, R. D. Leapman, N. W. Rizzo, F. Dyda, J. Reed, R. Tycko, *Biochemistry* 2000, 39, 13748.

26A. H. A. Lashuel, S. R. Labrenz, L. Woo, L. C. Serpell, J. W. Kelly, *J. Am. Chem. Soc.* 2000, 122, 5262.

27A. J. Adamcik, R. Mezzenga, *Soft Matter* 2011, 7, 5437.

28A. A. Pizzi, C. Pigliacelli, A. Gori, Nonappa, O. Ikkala, N. Demitri, G. Terraneo, V. Castelletto, I. W. Hamley, F. Baldelli Bombelli, P. Metrangolo, *Nanoscale* 2017, 9, 9805.

29A. a) J. Madine, E. Jack, P. G. Stockley, S. E. Radford, L. C. Serpell, D. A. Middleton, *J. Am. Chem. Soc.* 2008, 130, 14990; b) P. Westermark, U. Engström, K. H. Johnson, G. T. Westermark, C. Betsholtz, *Proc. Natl. Acad. Sci. USA* 1990, 87, 5036.

30A. A. B. Ahmed, A. V. Kajava, *FEBS Lett.* 2013, 587, 1089.

31A. M. López de la Paz, L. Serrano, *Proc. Natl. Acad. Sci. USA* 2004, 101, 87.

32A. S. Zhang, M. Andreasen, J. T. Nielsen, L. Liu, E. H. Nielsen, J. Song, G. Ji, F. Sun, T. Skrydstrup, F. Besenbacher, N. C. Nielsen, D. E. Otzen, M. Dong, *Proc. Natl. Acad. Sci. USA* 2013, 110, 2798.

33A. M. Andreasen, K. K. Skeby, S. Zhang, E. H. Nielsen, L. H. Klausen, H. Frahm, G. Christiansen, T. Skrydstrup, M. Dong, B. Schiott, D. Otzen, *Biochemistry* 2014, 53, 6968.

34A. M. P. López Deber, D. T. Hickman, D. Nand, M. Baldus, A. Pfeifer, A. Muhs, *PLoS One* 2014, 9, e105641.

35A. H. Cui, A. G. Cheetham, E. T. Pashuck, S. I. Stupp, *J. Am. Chem. Soc.* 2014, 136, 12461.

36A. Y. Wen, A. Waltman, H. Han, J. H. Collier, *ACS Nano* 2016, 10, 9274.

37A. E. H. Egelman, *Biophys. J.* 2016, 110, 1008.

38A. R. Diaz-Avalos, C. Long, E. Fontano, M. Balbirnie, R. Grothe, D. Eisenberg, D. L. Caspar, *J. Mol. Biol.* 2003, 330, 1165.

39A. M. Margittai, R. Langen, Q. *Rev. Biophys.* 2008, 41, 265.

40A. a) R. Nelson, M. R. Sawaya, M. Balbirnie, A. O. Madsen, C. Riekel, R. Grothe, D. Eisenberg, *Nature* 2005, 435, 773; b) H. Inouye, D. A. Kirschner, *Adv. Protein Chem.* 2006, 73, 181.

41A. a) M. Sebastiao, N. Quittot, S. Bourgault, *Anal. Biochem.* 2017, 532, 83; b) H. Naiki, K. Higuchi, M. Hosokawa, T. Takeda, *Anal. Biochem.* 1989, 177, 244.

42A. C. Louis-Jeune, M. A. Andrade-Navarro, C. Perez-Iratxeta, *Proteins: Struct., Funct., Bioinf.* 2012, 80, 374.

43A. a) H. Sakai, K. Watanabe, F. Kudoh, R. Kamada, Y. Chuman, K. Sakaguchi, *Sci. Rep.* 2016, 6, 31993; b) E. Gazit, *FASEB J.* 2002, 16, 77.

44A. M. R. Hilaire, B. Ding, D. Mukherjee, J. Chen, F. Gai, *J. Am. Chem. Soc.* 2018, 140, 629.

45A. a) E. H. Egelman, *Methods Enzymol.* 2010, 482, 167; b) E. H. Egelman, *eLife* 2014, 3, e04969.

46A. a) X. Zheng, L. Zhu, X. Zeng, L. Meng, L. Zhang, D. Wang, X. Huang, J. Phys. Chem. Lett. 2017, 8, 1798; b) A. Dehsorkhi, V. Castelletto, I. W. Hamley, *J. Pept. Sci.* 2014, 20, 453.

47A. J. Adamcik, V. Castelletto, S. Bolisetty, I. W. Hamley, R. Mezzenga, *Angew. Chem.*, Int. Ed. 2011, 50, 5495.

48A. M. Saiki, K. Shiba, M. Okumura, *FEBS Lett.* 2015, 589, 3541.

49A. M. Cao, S. Lu, W. Zhao, L. Deng, M. Wang, J. Wang, P. Zhou, D. Wang, H. Xu, J. R. Lu, *ACS Appl. Mater. Interfaces* 2017, 9, 39174.

50A. M. Novo, S. Freire, W. Al-Soufi, *Sci. Rep.* 2018, 8, 1783.

51A. F. Chiti, C. M. Dobson, *Annu. Rev. Biochem.* 2017, 86, 27.

52A. D. M. Fowler, A. V. Koulov, W. E. Balch, J. W. Kelly, *Trends Biochem. Sci.* 2007, 32, 217.

53A. a) I. Benilova, E. Karran, B. De Strooper, Nat. Neurosci. 2012, 15, 349; b) S. Bourgault, S. Choi, J. N. Buxbaum, J. W. Kelly, J. L. Price, N. Reixach, Biochem. Biophys. *Res. Commun.* 2011, 410, 707; c) R. Kayed, E. Head, J. L. Thompson, T. M. McIntire, S. C. Milton, C. W. Cotman, C. G. Glabe, *Science* 2003, 300, 486.

54A. a) A. Abedini, A. Plesner, P. Cao, Z. Ridgway, J. Zhang, L. H. Tu, C. T. Middleton, B. Chao, D. J. Sartori, F. Meng, H. Wang, A. G. Wong, M. T. Zanni, C. B. Verchere, D. P. Raleigh, A. M. Schmidt, *eLife* 2016, 5, e12977; b) P. T. Nguyen, X. Zottig, M. Sebastiao, S. Bourgault, *Biochemistry* 2017, 56, 3808.

55A. C. Cabaleiro-Lago, I. Lynch, K. A. Dawson, S. Linse, *Langmuir* 2010, 26, 3453.

56A. C. A. Carufel, P. T. Nguyen, S. Sahnouni, S. Bourgault, *Biopolymers* 2013, 100, 645.

57A. W. J. Becktel, J. A. Schellman, *Biopolymers* 1987, 26, 1859.

58A. T. Lefèvre, M. Subirade, M. Pézolet, *Biomacromolecules* 2005, 6, 3209.

59A. C. A. De Carufel, N. Quittot, P. T. Nguyen, S. Bourgault, *Angew. Chem., Int. Ed.* 2015, 54, 14383.

What is claimed is:

1. A construct comprising:

i) a self-assembling domain of the formula: $X^1$-$X^2$-$L^1$-Z wherein $X^1$ is a lysine residue or an analog thereof comprising a primary amine in its side chain, or is absent;

$X^2$ is a lysine residue or an analog thereof comprising a primary amine in its side chain;

$L^1$ is a peptide linker of 2 to 8 amino acids;

Z is a self-assembling amyloid peptide; and ii) a molecule conjugated to the self-assembling domain.

2. The construct of claim 1, wherein Z is a peptide of 15 amino acids or less comprising a sequence having at least 80% identity with the sequence SNNFGAIL (SEQ ID NO:2).

3. The construct of claim 1, wherein Z is a peptide of 15 amino acids or less comprising a sequence having at least 80% identity with the sequence SNNFGAILSS (SEQ ID NO:1).

4. The construct of claim 3, wherein Z is a peptide of the sequence SNNFGAILSS (SEQ ID NO:1).

5. The construct of claim 1, wherein $X^2$ and/or $X^1$ is a lysine residue.

6. The construct of claim 5, wherein $X^1$ and $X^2$ are lysine residues.

7. The construct of claim 1, wherein peptide linker $L^1$ comprises glycine residues, serine residues, or a mixture thereof.

8. The construct of claim 7, wherein peptide linker $L^1$ comprises or consists of the sequence GSGS (SEQ ID NO:4).

9. The construct of claim 1, wherein the self-assembling domain comprises or consists of the sequence KKGSGSSNNFGAILSS (SEQ ID NO: 5).

10. The construct of claim 1, wherein the molecule is conjugated to the self-assembling domain through a peptide linker $L^2$.

11. The construct of claim 1, wherein the molecule is an antigen.

12. The construct of claim 11, wherein the antigen is (i) a viral protein, a bacterial protein or a fungal protein, or a peptide fragment thereof; or (ii) a tumor-specific antigen.

13. The construct of claim 12, wherein the antigen is a peptide fragment derived from the extracellular domain of the influenza M2 protein (M2e).

14. The construct of claim 11, wherein the antigen is a peptide fragment of 10 to 50 amino acids.

15. A nanorod comprising the construct of claim 1, wherein the nanorod has a length of between about 100 to about 200 nm.

16. A composition comprising a plurality of nanorods according to claim 15, wherein the plurality of nanorods have an average length of about 100 to about 200 nm±30-50 nm.

17. A vaccine comprising (i) the construct of claim 1, and (ii) a vaccine adjuvant.

18. The vaccine of claim 17, further comprising a pharmaceutically acceptable excipient.

19. A method for inducing an immune response against an antigen in a subject comprising administering to the subject an effective amount of the construct of claim 11, or of a vaccine comprising the construct of claim 11 and a vaccine adjuvant.

20. A method for preventing and/or treating a microbial infection or treating a cancer in a subject comprising administering to the subject an effective amount of the construct of claim 12, or of a vaccine comprising the construct of claim 12 and a vaccine adjuvant.

* * * * *

SEQUENCE LISTING

```
<160> NUMBER OF SEQ ID NOS: 14

<210> SEQ ID NO 1
<211> LENGTH: 10
<212> TYPE: PRT
<213> ORGANISM: Homo sapiens

<400> SEQUENCE: 1

Ser Asn Asn Phe Gly Ala Ile Leu Ser Ser
1               5                   10


<210> SEQ ID NO 2
<211> LENGTH: 8
<212> TYPE: PRT
<213> ORGANISM: Homo sapiens

<400> SEQUENCE: 2

Ser Asn Asn Phe Gly Ala Ile Leu
1               5


<210> SEQ ID NO 3
<211> LENGTH: 9
<212> TYPE: PRT
<213> ORGANISM: Homo sapiens

<400> SEQUENCE: 3

Ser Asn Asn Phe Gly Ala Ile Leu Ser
1               5


<210> SEQ ID NO 4
<211> LENGTH: 4
<212> TYPE: PRT
<213> ORGANISM: Artificial Sequence
<220> FEATURE:
<223> OTHER INFORMATION: peptide linker

<400> SEQUENCE: 4

Gly Ser Gly Ser
1


<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Lys Lys Gly Ser Gly Ser Ser Asn Asn Phe Gly Ala Ile Leu Ser Ser
1               5                   10                  15


<210> SEQ ID NO 6
<211> LENGTH: 23
<212> TYPE: PRT
<213> ORGANISM: Influenza A virus

<400> SEQUENCE: 6

Ser Leu Leu Thr Glu Val Glu Thr Pro Ile Arg Asn Glu Trp Gly Ser
1               5                   10                  15

Arg Ser Asn Gly Ser Ser Asp
            20


<210> SEQ ID NO 7
<211> LENGTH: 5
<212> TYPE: PRT
```

```
<213> ORGANISM: Homo sapiens

<400> SEQUENCE: 7

Phe Gly Ala Ile Leu
1               5


<210> SEQ ID NO 8
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: Cyano-phenylalanine residue

<400> SEQUENCE: 8

Lys Gly Ser Gly Ser Ser Asn Asn Xaa Gly Ala Ile Leu Ser Ser
1               5                   10                  15


<210> SEQ ID NO 9
<211> LENGTH: 15
<212> TYPE: PRT
<213> ORGANISM: Artificial Sequence
<220> FEATURE:
<223> OTHER INFORMATION: synthetic peptide

<400> SEQUENCE: 9

Arg Gly Ser Gly Ser Ser Asn Asn Phe Gly Ala Ile Leu Ser Ser
1               5                   10                  15


<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

His Gly Ser Gly Ser Ser Asn Asn Phe Gly Ala Ile Leu Ser Ser
1               5                   10                  15


<210> SEQ ID NO 11
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Dbu

<400> SEQUENCE: 11

Xaa Gly Ser Gly Ser Ser Asn Asn Phe Gly Ala Ile Leu Ser Ser
1               5                   10                  15


<210> SEQ ID NO 12
<211> LENGTH: 14
<212> TYPE: PRT
<213> ORGANISM: Artificial Sequence
<220> FEATURE:
<223> OTHER INFORMATION: Synthetic construct

<400> SEQUENCE: 12

Gly Ser Gly Ser Ser Asn Asn Phe Gly Ala Ile Leu Ser Ser
1               5                   10
```

-continued

```
<210> SEQ ID NO 13
<211> LENGTH: 15
<212> TYPE: PRT
<213> ORGANISM: Artificial Sequence
<220> FEATURE:
<223> OTHER INFORMATION: Synthetic construct

<400> SEQUENCE: 13

Lys Gly Ser Gly Ser Ser Asn Asn Phe Gly Ala Ile Leu Ser Ser
1               5                   10                  15


<210> SEQ ID NO 14
<211> LENGTH: 14
<212> TYPE: PRT
<213> ORGANISM: Artificial Sequence
<220> FEATURE:
<223> OTHER INFORMATION: GSGSSNNFGAILSK

<400> SEQUENCE: 14

Gly Ser Gly Ser Ser Asn Asn Phe Gly Ala Ile Leu Ser Lys
1               5                   10
```